US008536328B2

(12) United States Patent
Remenar et al.

(10) Patent No.: US 8,536,328 B2
(45) Date of Patent: Sep. 17, 2013

(54) PROCESS FOR SYNTHESIZING OXIDIZED LACTAM COMPOUNDS

(75) Inventors: Julius F. Remenar, Framingham, MA (US); Laura Cook Blumberg, Lincoln, MA (US); Tarek A. Zeidan, Watertown, MA (US)

(73) Assignee: Alkermes Pharma Ireland Limited, Dublin (IE)

( * ) Notice: Subject to any disclaimer, the term of this patent is extended or adjusted under 35 U.S.C. 154(b) by 0 days.

(21) Appl. No.: 13/100,515

(22) Filed: May 4, 2011

(65) Prior Publication Data

US 2011/0275803 A1 Nov. 10, 2011

Related U.S. Application Data

(60) Provisional application No. 61/331,128, filed on May 4, 2010.

(51) Int. Cl.
*C07D 265/00* (2006.01)

(52) U.S. Cl.
USPC .......................................................... 544/63

(58) Field of Classification Search
USPC .......................................................... 544/63
See application file for complete search history.

(56) References Cited

PUBLICATIONS

Williams, J. M., et al. "Sequential Dehydrogenation of 3-Keto-4-azasteroids. The Reaction of Ene-Lactams with 2,3-Dichloro-5,6-dicyano-1,4-benzoquinone (DDQ)," *J. Org. Chem.*, 60(16): pp. 5337-5340 (1995).
Chander, T.P., et al., "Synthesis and Characterization of Related Compounds of Aripiprazole, an Antipsychotic Drug Substance," *Synthetic Communications 37*: pp. 4337-4341 (2007).
Simplicio, A.L., et al., "Prodrugs for Amines," *Molecules 13*: pp. 519-547 (2008).

*Primary Examiner* — Paul V. Ward
(74) *Attorney, Agent, or Firm* — Roy P. Issac; Carolyn S. Elmore; Elmore Patent Law Group, P.C.

(57) ABSTRACT

The invention provides a method for the synthesis of dehydrogenated lactam drugs of Formula I:

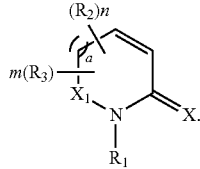

Formula I

7 Claims, No Drawings

PROCESS FOR SYNTHESIZING OXIDIZED LACTAM COMPOUNDS

RELATED APPLICATION(S)

This application claims the benefit of U.S. Provisional Application No. 61/331,128, filed on May 4, 2010. The entire teachings of the above application(s) are incorporated herein by reference.

BACKGROUND OF THE INVENTION (i) Field of the Invention

The present invention relates to preparation of dehydrogenated lactam drugs including synthesis of dehydrogenated aripiprazole and cilostazol.

(ii) Background of the Invention

Many of the lactam containing drugs are metabolized to their dehydrogenated form and are often biologically active. For example, carbostyril derivatives can be metabolized to form dehydrogenated carbostyril derivatives. An example of such a drug is aripiprazole which is metabolized by Cytochrome P450 2D6 (CYP2D6) and CYP3A4 to give the active metabolite dehydro aripiprazole (7-[4-[4-(2,3-dichlorophenyl)-1-piperazinyl]butoxy]-3,4-dehydro-2-(1H) quinolinone). (Kirschbaum et al., *The World Journal of Biological Chemistry*, 2008 9(3), 212-8). Satyanarayana et al. recently reported a method for synthesizing dehydro aripiprazole using dichlorodicyanoquinone. (*Heterocyclic Communications*, 2005, 11(6), 485-490). However, the procedure reported results in moderate yield (42.5%). While dehydro aripiprazole is commercially available it is exorbitantly expensive. For example, it costs more than $13/mg from SynFine Research Inc. As such, a more efficient less expensive methodology is needed to produce dehydro aripiprazole and other oxidized lactam and carbostyril derivative drugs.

SUMMARY OF THE INVENTION

In part, the invention provides for the synthesis of a compound of Formula I by the oxidation of Formula IA.

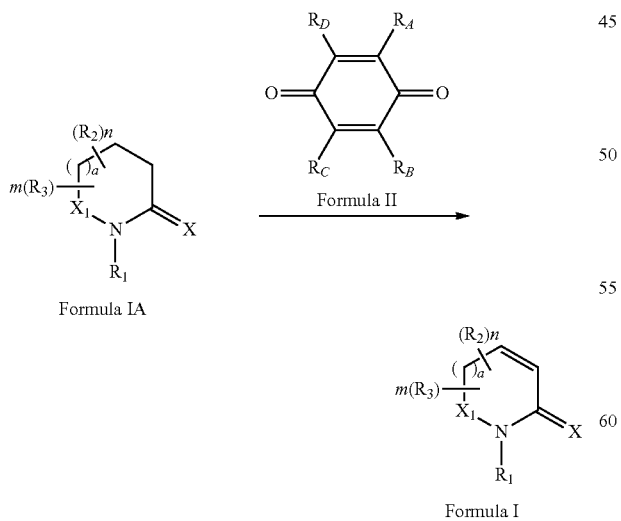

wherein X is —S— or —O—;
Each n, m and a is independently selected from 0, 1, 2 or 3;
$X_1$ is selected from absent, —S—, —O—, —S(O)—, —S(O)$_2$—, —N(R$_{10}$)—, —C(O)—, —C(OR$_{10}$)(R$_{11}$)—, —[C(R$_{10}$)(R$_{11}$)]$_v$—, —C(R$_{10}$)(R$_{11}$)=C(R$_{10}$)(R$_{11}$)—;
wherein v is 0, 1, 2, 3, 4, 5;
wherein each $R_{10}$ and $R_{11}$ is independently absent, hydrogen, halogen, aliphatic, substituted aliphatic, aryl or substituted aryl; alternatively two $R_{10}$ and $R_{11}$ together with the atoms to which they are attached may form an additional optionally substituted, 3, 4, 5, 6 or 7 membered ring; and Each $R_1$, $R_2$ and $R_3$ is independently absent, hydrogen, halogen, aliphatic, substituted aliphatic, aryl or substituted aryl; alternatively two or more $R_1$, $R_2$ and $R_3$ together with the atoms to which they are attached may form one or two additional optionally substituted, 3, 4, 5, 6 or 7 membered ring; and Each $R_A$, $R_B$, $R_C$, and $R_D$ is independently selected from hydrogen, halogen, —CN, NR$_{100}$R$_{101}$, wherein said compound of Formula IA contain a secondary or tertiary amine having a pKa of about 6 to about 45.

In part, a process for synthesizing oxidized lactam and carbostyril derivatives is provided. In particular, an efficient method for oxidizing aripiprazole, cilastozol and PF-00217830 to produce their corresponding dehydrogenated compounds. The dehydrogenation reaction is conducted by the addition of a compound of Formula II to a compound of Formula IA in the presence of an acid.

DETAILED DESCRIPTION OF THE INVENTION

In part, the invention provides a method for the synthesis of a compound of Formula I by the oxidation of a compound of Formula IA:

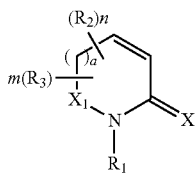

Formula I

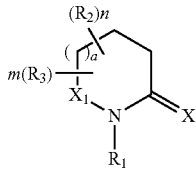

Formula IA wherein X is —S— or —O—;
Each n, m and a is independently selected from 0, 1, 2 or 3;
$X_1$ is selected from absent, —S—, —O—, —S(O)—, —S(O)$_2$—, —N(R$_{10}$)—, —C(O)—, —C(OR$_{10}$)(R$_{11}$)—, —C(R$_{10}$)(R$_{11}$)$_v$—, —C(R$_{10}$)(R$_{11}$)=C(R$_{10}$)(R$_{11}$)—;
wherein v is 0, 1, 2, 3, 4, 5;
wherein each $R_{10}$ and $R_{11}$ is independently absent, hydrogen, halogen, aliphatic, substituted aliphatic, aryl or substituted aryl; alternatively two $R_{10}$ and $R_{11}$ together with the atoms to which they are attached may form an additional optionally substituted, 3, 4, 5, 6 or 7 membered ring; and each $R_1$, $R_2$ and $R_3$ is independently absent, hydrogen, halogen, aliphatic, substituted aliphatic, aryl or substituted aryl; alternatively two or more $R_1$, $R_2$ and $R_3$ together with the atoms to which they are attached may form one or two additional optionally substituted, 3, 4, 5, 6 or 7 membered ring; wherein the step of oxidation is comprises the addition of a compound of Formula II:

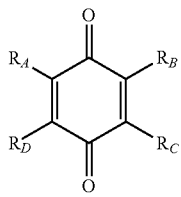

Formula II wherein each $R_A$, $R_B$, $R_C$, and $R_D$ is independently selected from hydrogen, halogen, —CN, $NR_{100}R_{101}$ aliphatic, substituted aliphatic, aryl and substituted aryl; and
an acid;
wherein said compound of Formula IA contain a primary, secondary or tertiary amine having a pKa of about 6 to about 45.

In another embodiment, the process involves the synthesis of a compound of Formula III by the oxidation of a compound of Formula IIIA.

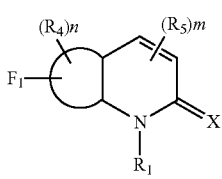

Formula III

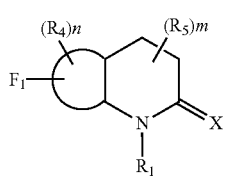

Formula IIIA wherein, X, $R_1$, m and n are as defined above;
Said compound of Formula IIIA contain a primary, secondary or tertiary amine having a pKa of about 6 to about 45;
The semicircle represents a cyclic moiety containing one, two or three rings;
Each $R_4$ and $R_5$ is independently absent, hydrogen, halogen, aliphatic, substituted aliphatic, aryl or substituted aryl; alternatively two or more $R_4$ and $R_5$ together with the atoms to which they are attached may form one or two additional optionally substituted, 3, 4, 5, 6 or 7 membered ring;
$F_1$ is selected from absent and $R_6$-A-$Cy_1$-B-D-;
  wherein, A is selected from absent, optionally substituted alkyl, optionally substituted alkenyl, optionally substituted alkynyl, —S—, —O—, —S(O)—, —S(O)$_2$—, —S[C(R$_{12}$)(R$_{13}$)]$_u$—, —S(O)[C(R$_{12}$)(R$_{13}$)]$_u$—, —S(O)$_2$[C(R$_{12}$)(R$_{13}$)]$_u$—, —O[C(R$_{12}$)(R$_{13}$)]$_u$—, —N(R$_{12}$)—, —N(R$_{12}$)[C(R$_{13}$)(R$_{14}$)]$_u$—, —[C(R$_{12}$)(R$_{13}$)]$_u$—, —C(O)[C(R$_{12}$)(R$_{13}$)]$_u$—; wherein each $R_{12}$, $R_{13}$ and $R_{14}$ is independently absent, hydrogen, halogen, aliphatic, substituted aliphatic, aryl or substituted aryl; wherein each u is independently 1, 2, 3, 4, 5, 6 or 7;
  $Cy_1$ is absent or an optionally substituted cycloalkyl, optionally substituted cycloalkenyl, optionally substituted heterocyclyl, optionally substituted aryl or optionally substituted heteroaryl;
  B is absent, or a linker;
  D is selected from absent, —O—, —NR$_{15}$, —C(R$_{15}$)(R$_{16}$)—, —S—, —S(O)—, —S(O)$_2$—, —C(O)—;
    wherein $R_{15}$, and $R_{16}$ is independently selected from absent, hydrogen, halogen, optionally substituted aliphatic, optionally substituted aryl or optionally substituted heterocyclyl; and
  $R_6$ is independently absent, hydrogen, halogen, aliphatic, substituted aliphatic, aryl, substituted aryl, heteroaryl, substituted heteroaryl, heterocyclyl or substituted heterocyclyl.

In a preferred embodiment, a method for the synthesis of a compound of Formula IV is provided:

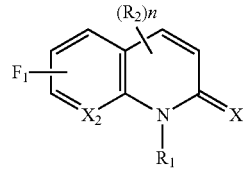

Formula IV

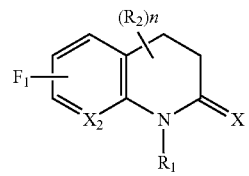

Formula IVA wherein, n, X, $F_1$, $R_1$, and $R_2$ are as defined above;
Said compound of Formula IVA contain a primary, secondary or tertiary amine having a pKa of about 6 to about 45; and
$X_2$ is selected from CH and N.

In a preferred embodiment a method for the synthesis of a compound of Formula V is provided:

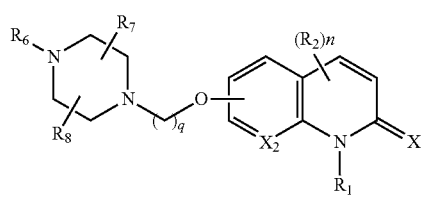

Formula V

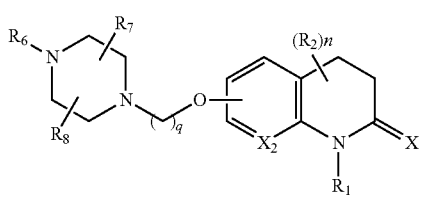

Formula VA wherein n, X, $X_2$, $R_1$, $R_2$, and $R_6$ are as defined above;
Said compound of Formula VA contain a primary, secondary or tertiary amine having a pKa of about 6 to about 45; and
q is 0, 1, 2, 3, 4, 5, 6, 7, 8, or 9;
$R_7$ and $R_8$ are independently selected from absent, hydrogen, halogen, aliphatic, substituted aliphatic, aryl or substituted aryl.

In a preferred embodiment a method for the synthesis of compounds of Formula VI-XI, is provided where a corresponding compound of Formula VIA-XIA is oxidized by reacting with a compound of Formula II in the presence of an acid: In a preferred embodiment, the compound of Formula II is DDQ and the acid is trifluoroacetic acid.

Formula VI

Formula VIA

Formula VII

Formula VIIA

Formula VIII

Formula VIIIA

Formula IX

Formula IXA

Formula X

Formula XA

Formula XI

Formula XIA

In a preferred embodiment, the $R_6$ moiety is an aryl or heteroaryl group selected from:

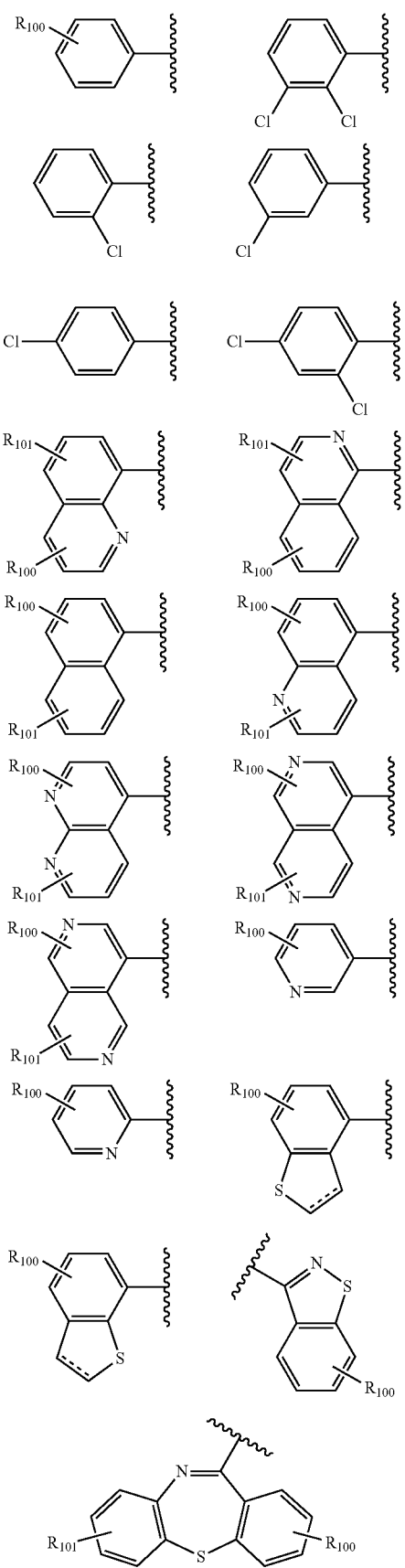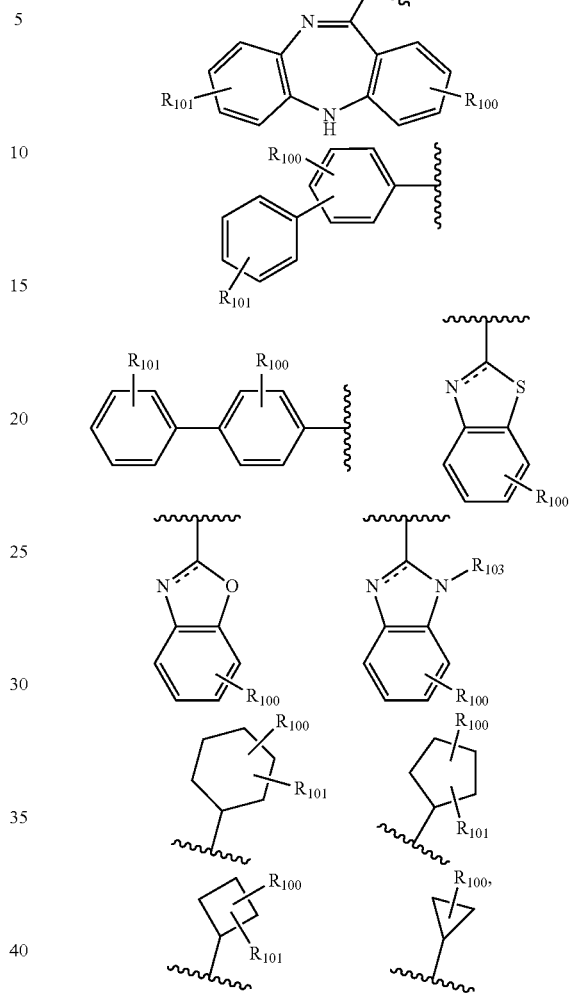

wherein $R_{100}$, $R_{101}$, and $R_{103}$ are independently selected from hydrogen, halogen, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ alkylamino and optionally substituted $C_1$-$C_8$ aryl.

In a preferred embodiment, $R_6$ is selected from:

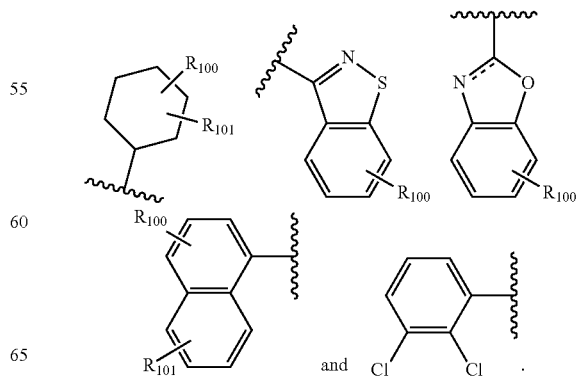

In a preferred embodiment, Cy1 is selected from:

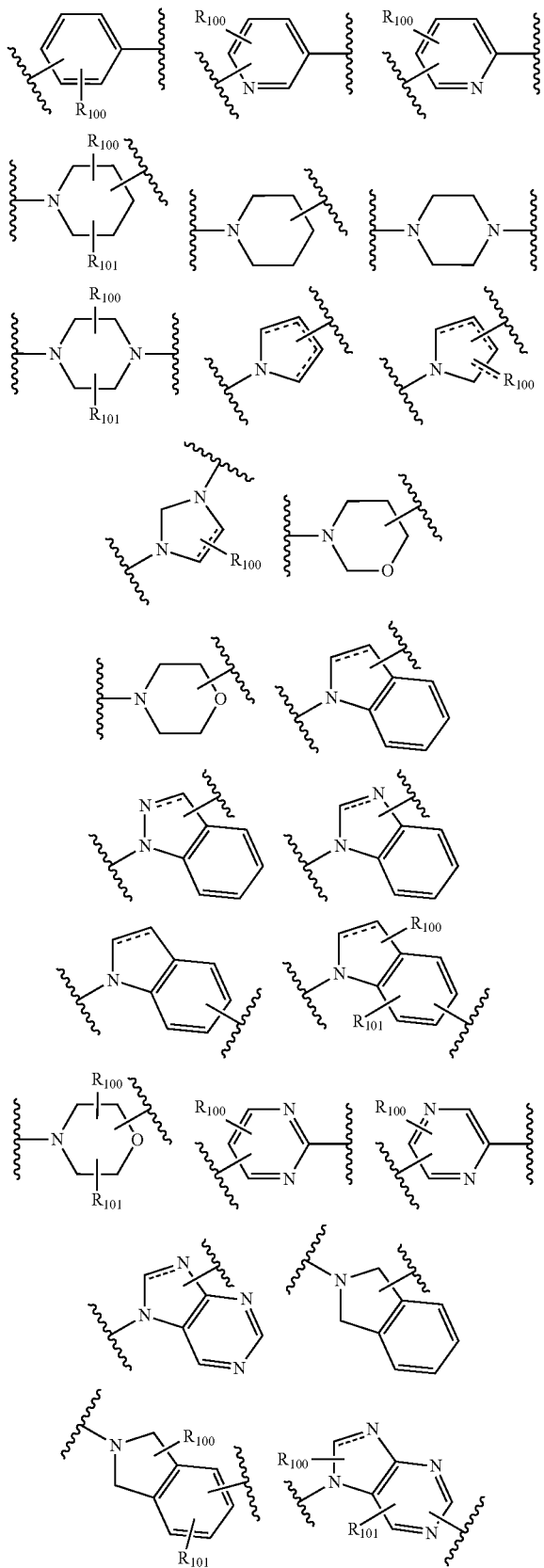

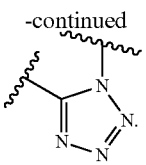

In a preferred embodiment, Cy1 is selected from:

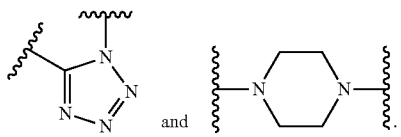 [SMILES: *c1nnnn1* ; *N1CCN(*)CC1]

and

In a preferred embodiment, the bivalent B is a direct bond, a straight chain $C_1$-$C_{10}$ alkyl, $C_1$-$C_{10}$ alkenyl, $C_1$-$C_{10}$ alkynyl, $C_1$-$C_{10}$ alkoxy, alkoxy $C_1$-$C_{10}$alkoxy, $C_1$-$C_{10}$ alkylamino, alkoxy$C_1$-$C_{10}$alkylamino, $C_1$-$C_{10}$ alkylcarbonylamino, $C_1$-$C_{10}$ alkylaminocarbonyl, aryloxy$C_1$-$C_{10}$alkoxy, aryloxy$C_1$-$C_{10}$alkylamino, aryloxy$C_1$-$C_{10}$alkylamino carbonyl, $C_1$-$C_{10}$-alkylaminoalkylaminocarbonyl, $C_1$-$C_{10}$ alkyl(N-alkyl)aminoalkyl-aminocarbonyl, alkylaminoalkylamino, alkylcarbonylaminoalkylamino, alkyl(N-alkyl)aminoalkylamino, (N-alkyl)alkylcarbonylaminoalkylamino, alkylaminoalkyl, alkylaminoalkylaminoalkyl, alkylpiperazinoalkyl, piperazinoalkyl, alkylpiperazino, alkenylaryloxyC1-C10alkoxy, alkenylarylamino$C_1$-$C_{10}$alkoxy, alkenylarylalkylamino$C_1$-$C_{10}$alkoxy, alkenylaryloxy$C_1$-$C_{10}$alkylamino, alkenylaryloxy$C_1$-$C_{10}$alkylaminocarbonyl, piperazinoalkylaryl, heteroaryl$C_1$-$C_{10}$alkyl, heteroaryl$C_2$-$C_{10}$alkenyl, heteroaryl$C_2$-$C_{10}$alkynyl, heteroaryl$C_1$-$C_{10}$alkylamino, heteroaryl$C_1$-$C_{10}$alkoxy, heteroaryloxy$C_1$-$C_{10}$alkyl, heteroaryloxy$C_2$-$C_{10}$alkenyl, heteroaryloxy$C_2$-$C_{10}$alkynyl, heteroaryloxy$C_1$-$C_{10}$alkylamino and heteroaryloxy$C_1$-$C_{10}$alkoxy.

In a preferred embodiment one of $R_A$, $R_B$, $R_C$, and $R_D$ is selected from an electron withdrawing group.

In a preferred embodiment, the quinone of Formula II is selected from 3,4-dichloro-5,6-dicyano-1,4-benzoquinone (DDQ), 3,4,5,6-tetrachloro-1,2-benzoquinone, ortho-benzoquinone and para-benzoquinone.

In some embodiments, the acid used in the reaction can be a halogenated organic acid. In some embodiments, the halogenated organic acid is a fluorinated carboxylic acid. In some embodiments, the acid is selected from trifluoroacetic acid, p-toluenesulfonic acid, trifluoromethanesulfonic acid, chlorosulfonic acid, dichloroacetic acid, trichloroacetic acid, acetic acid, propionic acid, sulfuric acid, phosphoric acid, nitric acid, camphorsulfonic acid, hydrochloric acid, oxalic acid, formic acid, propanoic acid, butanoic acid, pentanoic acid, benzoic acid, pyruvic acid, malonic acid, succinic acid, glutaric acid, fumaric acid, citric acid, ascorbic acid, tartaric acid, maleic acid, hydrobromic acid, galuturonic acid, embonic acid, glutamic acid and aspartic acid, glyconic acid, succinic acid and mixtures thereof.

In some embodiments, said compounds of Formula IA, IIIA, IVA and VA contain a primary, secondary or tertiary amine moiety having a pKa of about 6 to about 45, preferably about 6 to about 30, and preferably about 7 to about 20. In some embodiments, the semicircle from Formula III and IIIA can be an optionally substituted heterocyclyl, aryl or heteroaryl containing one, two or three rings.

In some embodiments, the reaction is conducted in a solvent selected from tetrahydrofuran, tert-butylmethylether, dimethoxy-ethane, dioxane, benzene, toluene, xylene, dimethylformamide, acetone, acetonitrile, chloroform, dichloromethane, 1,2-dichloroethane, ethyl acetate, n-propyl acetate, isopropyl acetate, methyl-t-butyl ether, methyl butyl ketone and combinations thereof.

In a preferred embodiment, $R_1$ is selected from H, —C($R_J$)($R_K$)—O$R_{20}$, —C($R_J$)($R_K$)—OC(O)O$R_{20}$, —C($R_J$)($R_K$)—OC(O)$R_{20}$, —($R_J$)($R_K$)—OC(O)N$R_{20}R_{21}$, —C($R_J$)($R_K$))—OPO$_3$MY, —(C($R_J$)($R_K$))—OP(O)(O$R_{20}$)(O$R_{21}$), —[C($R_J$)($R_K$)O]$_z$—$R_{20}$, —[C($R_J$)($R_K$)O]$_z$—C(O)O$R_{20}$, —[C($R_J$)($R_K$)O]$_z$—C(O)$R_{20}$, —[C($R_J$)($R_K$)O]$_z$—C(O)N$R_{20}R_{21}$, —[C($R_J$)($R_K$)O]$_z$—OPO$_3$MY, —[C($R_J$)($R_K$)O]$_z$—P(O)$_2$(O$R_{20}$)M and —[C($R_J$)($R_K$)O]$_z$—P(O)(O$R_{20}$)(O$R_{21}$);

wherein each $R_J$ and $R_K$ is independently selected from hydrogen, halogen, aliphatic, substituted aliphatic, aryl or substituted aryl;

each $R_{20}$ and $R_{21}$ is independently selected from hydrogen, aliphatic, substituted aliphatic, aryl or substituted aryl;

Y and M are the same or different and each is a monovalent cation; or M and Y together is a divalent cation; and z is 0, 1, 2, 3, 4, 5, 6, 7, 8, 9 or 10.

In a preferred embodiment, $R_1$ is selected from Table-1.

TABLE 1

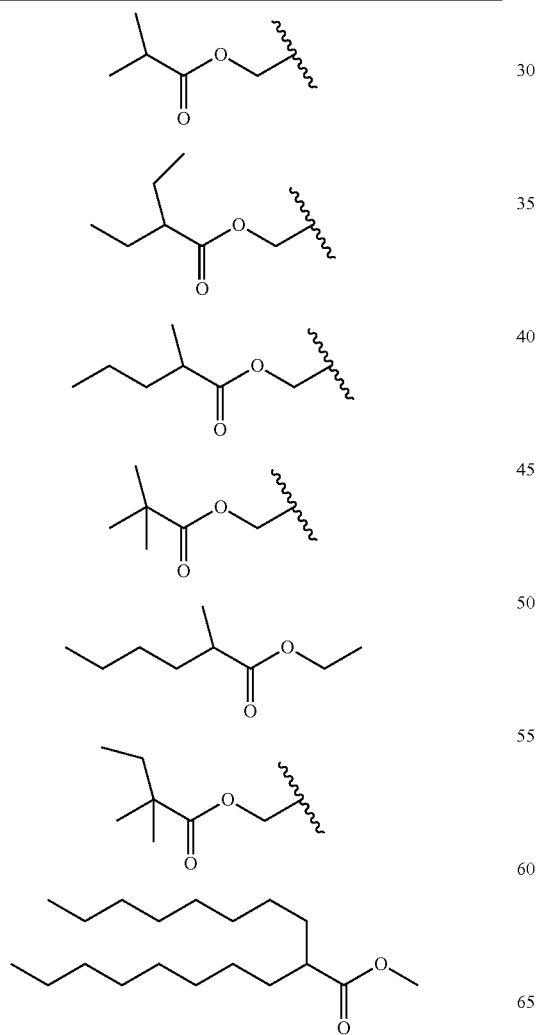

TABLE 1-continued

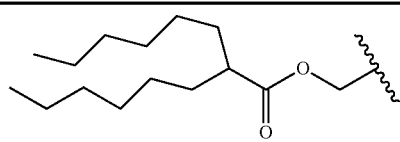
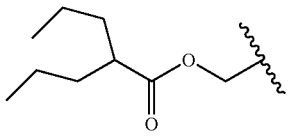
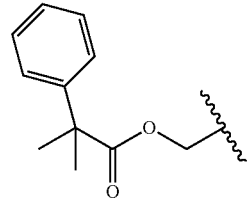 [SMILES: *COC(=O)C(C)(C)c1ccccc1]
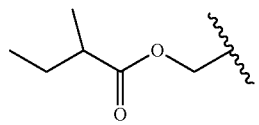 [SMILES: *COC(=O)C(C)CC]
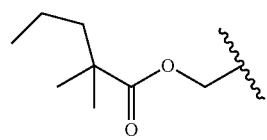 [SMILES: *COC(=O)C(C)(C)CCC]
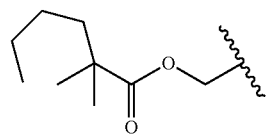 [SMILES: *COC(=O)C(C)(C)CCCC]
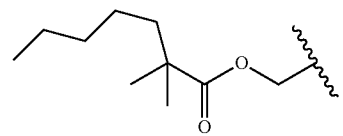 [SMILES: *COC(=O)C(C)(C)CCCCC]
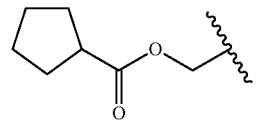 [SMILES: *COC(=O)C1CCCC1]
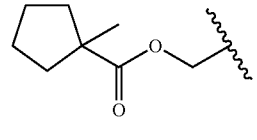 [SMILES: *COC(=O)C1(C)CCCC1]
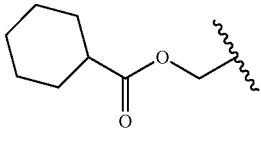 [SMILES: *COC(=O)C1CCCCC1]
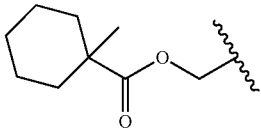 [SMILES: *COC(=O)C1(C)CCCCC1]

TABLE 1-continued
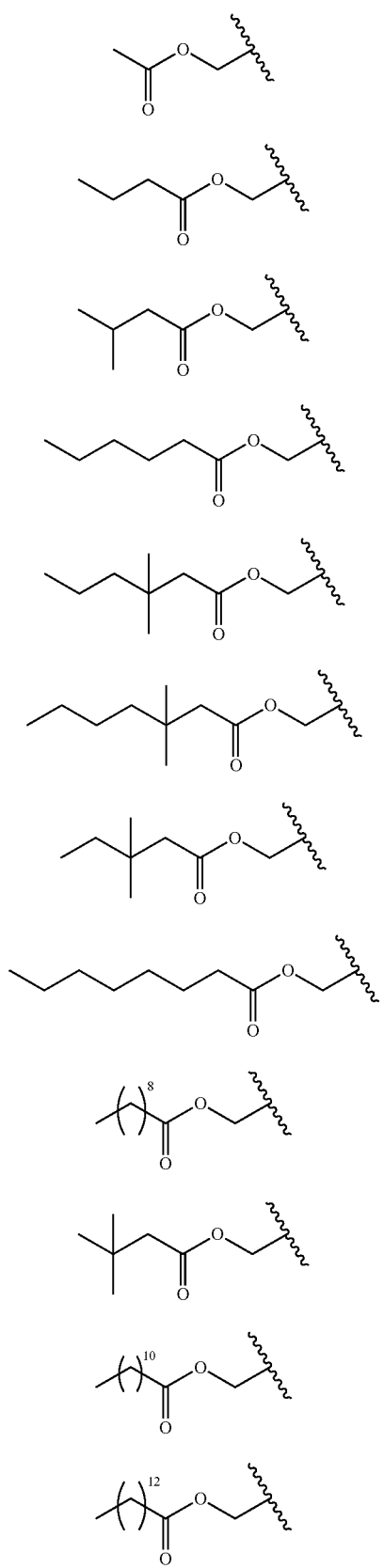
TABLE 1-continued
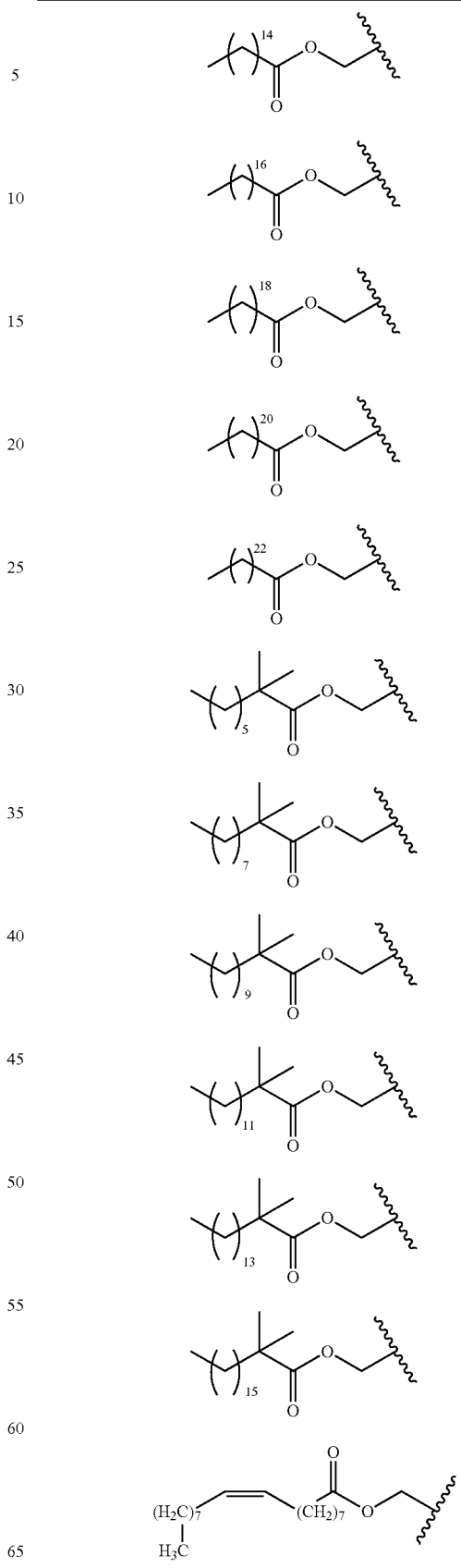

TABLE 1-continued
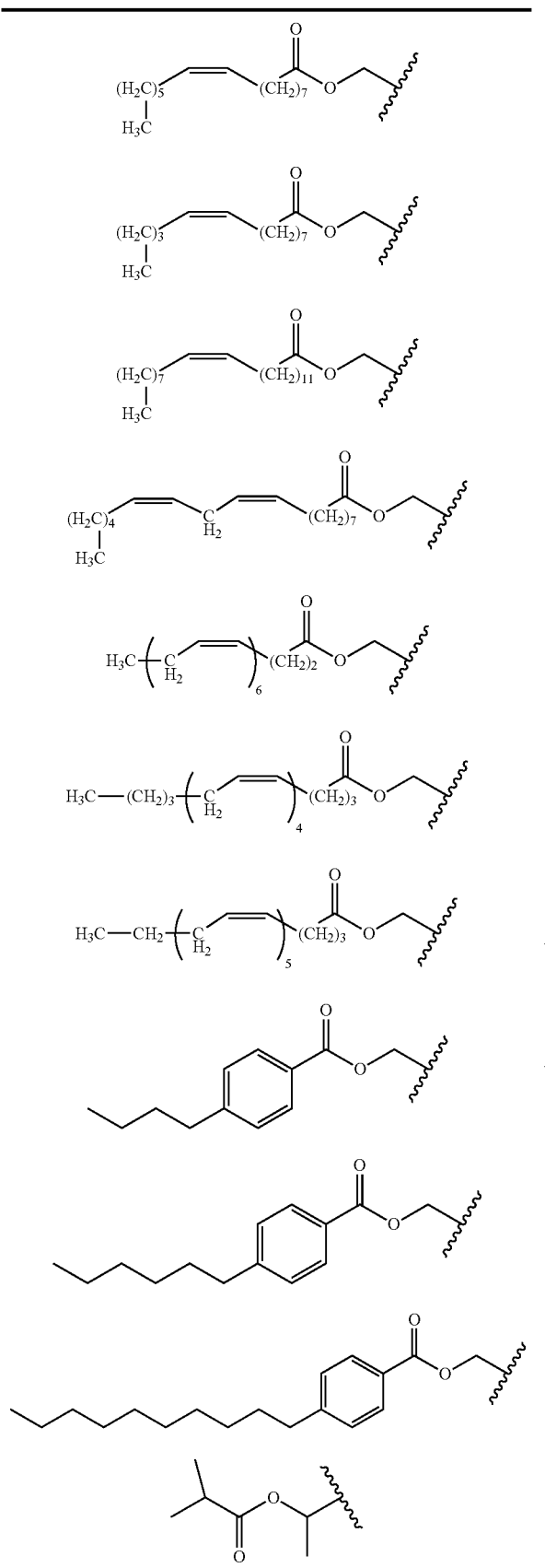
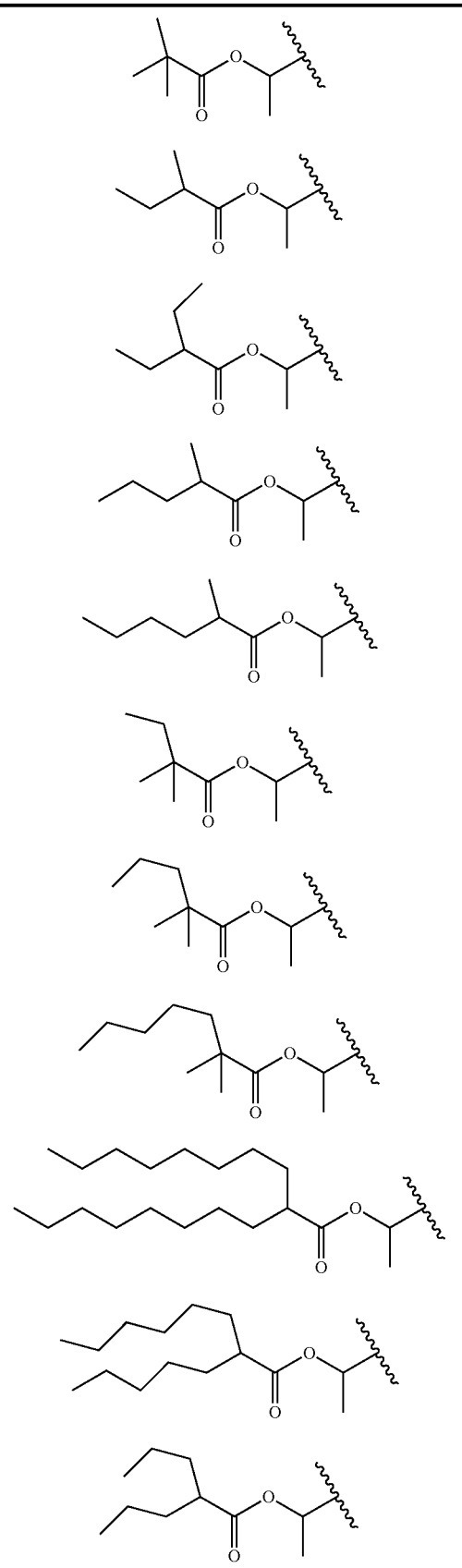

TABLE 1-continued
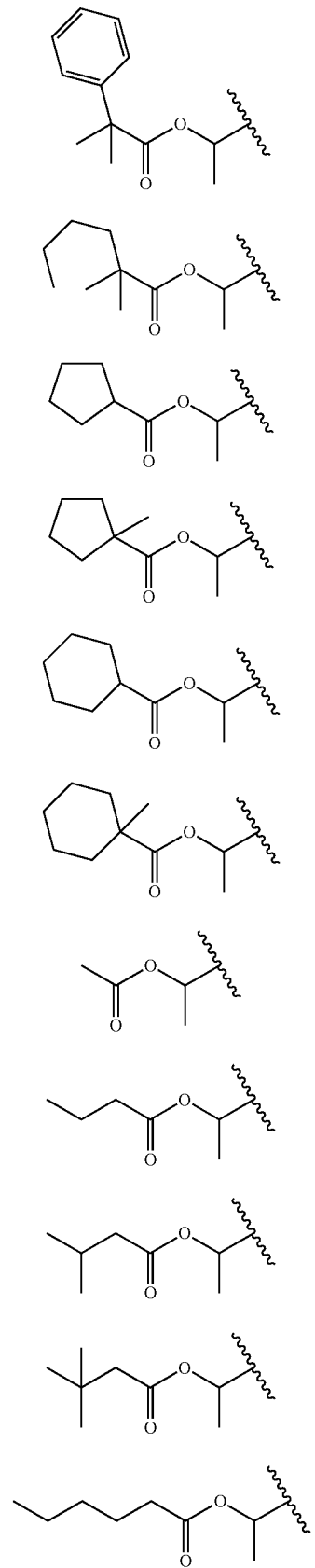
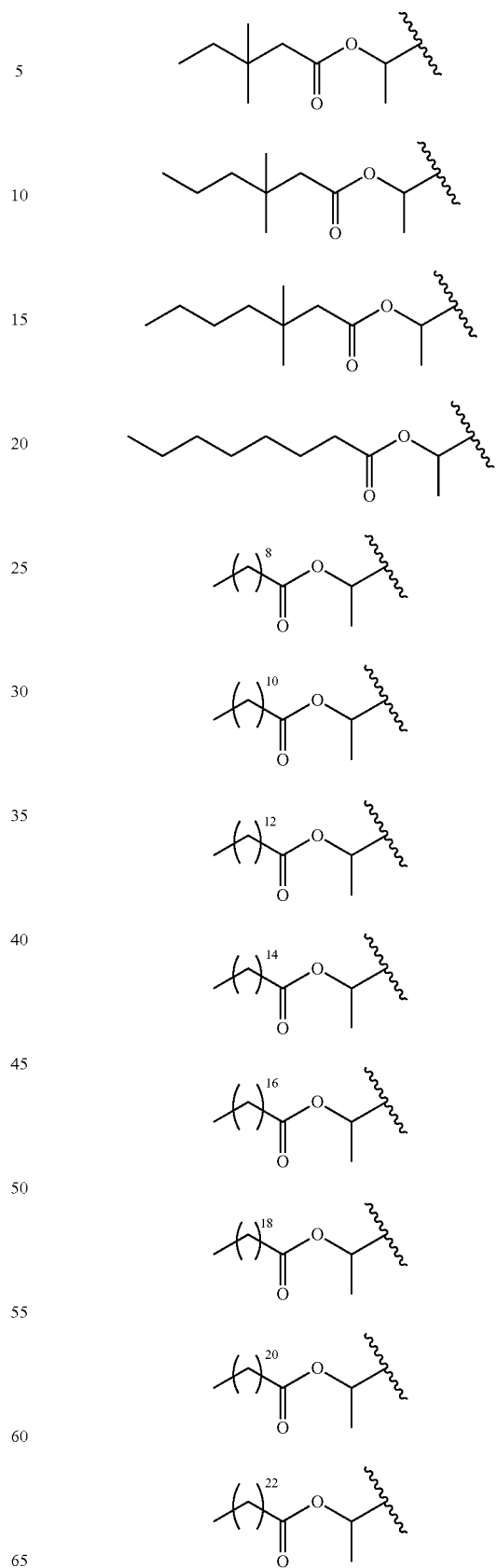

TABLE 1-continued
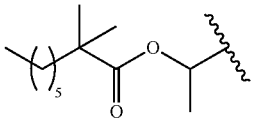
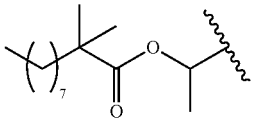
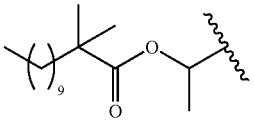
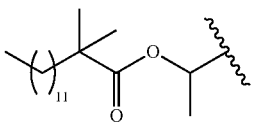
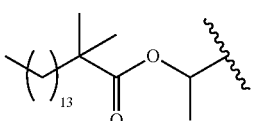
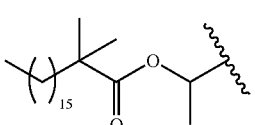
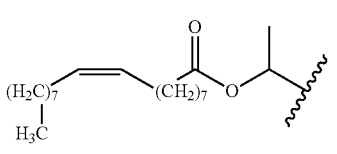
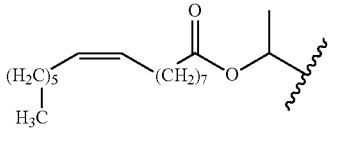
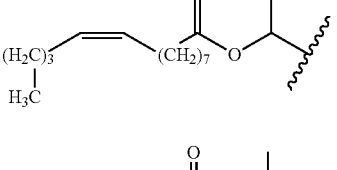
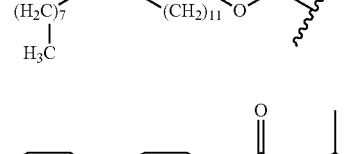
TABLE 1-continued
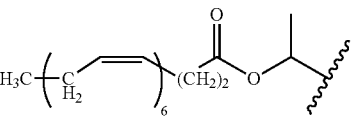
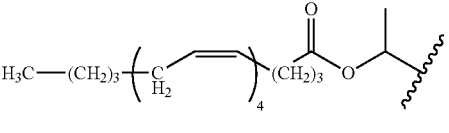
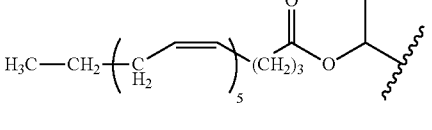
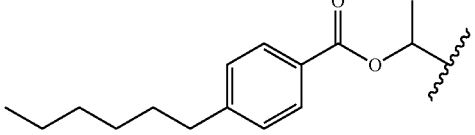
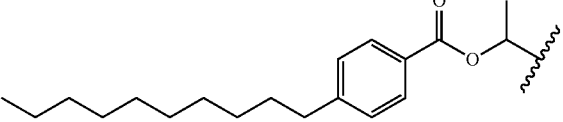
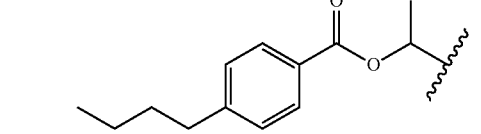
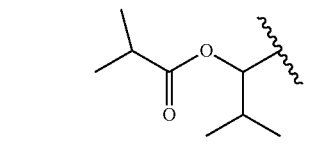 [SMILES: *C(OC(=O)C(C)C)C(C)C]
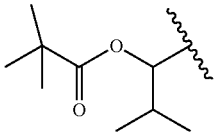 [SMILES: *C(OC(=O)C(C)(C)C)C(C)C]
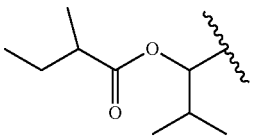 [SMILES: *C(OC(=O)C(C)CC)C(C)C]
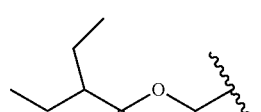
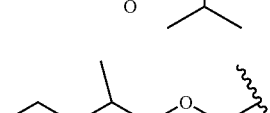

TABLE 1-continued
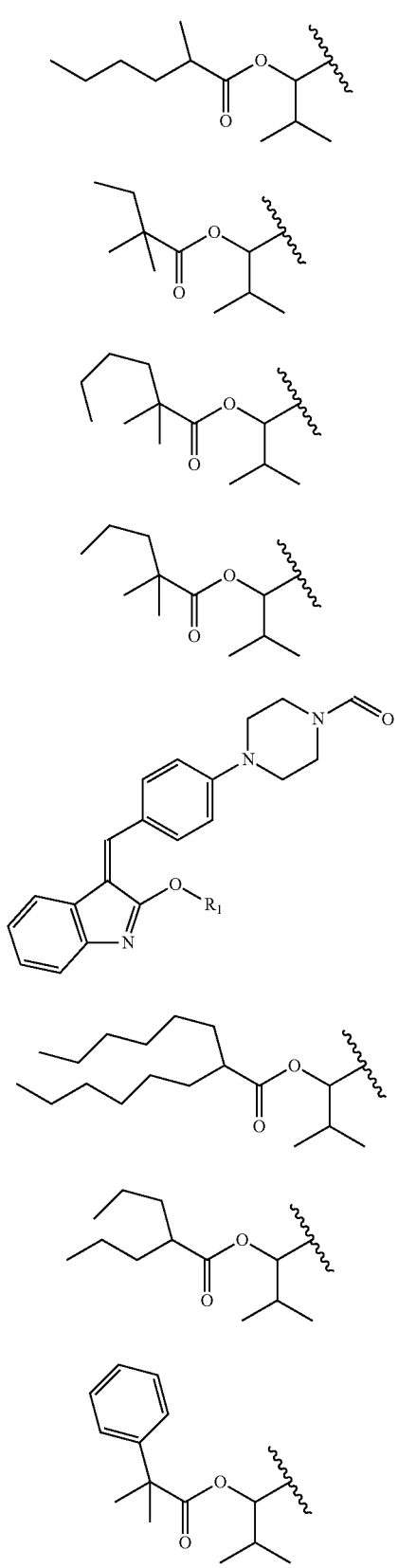
TABLE 1-continued
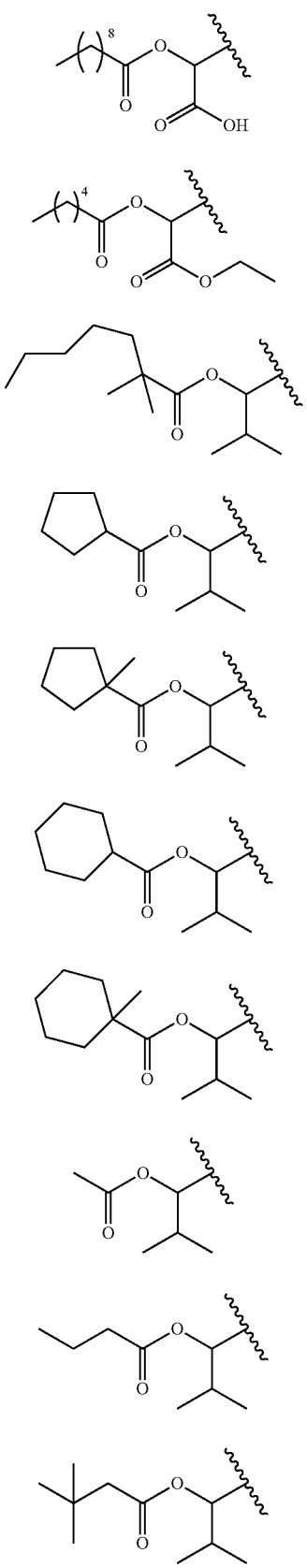

TABLE 1-continued
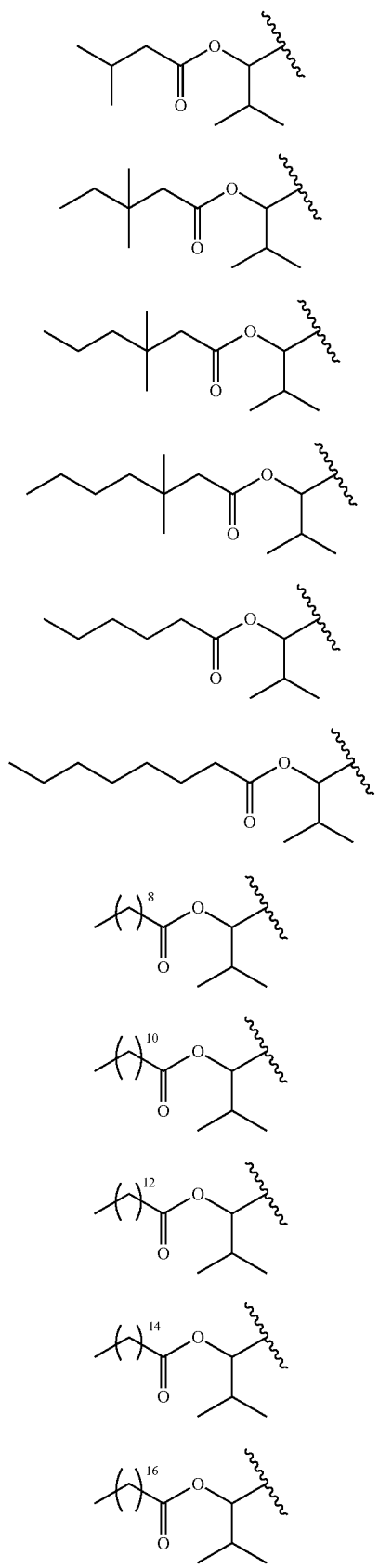
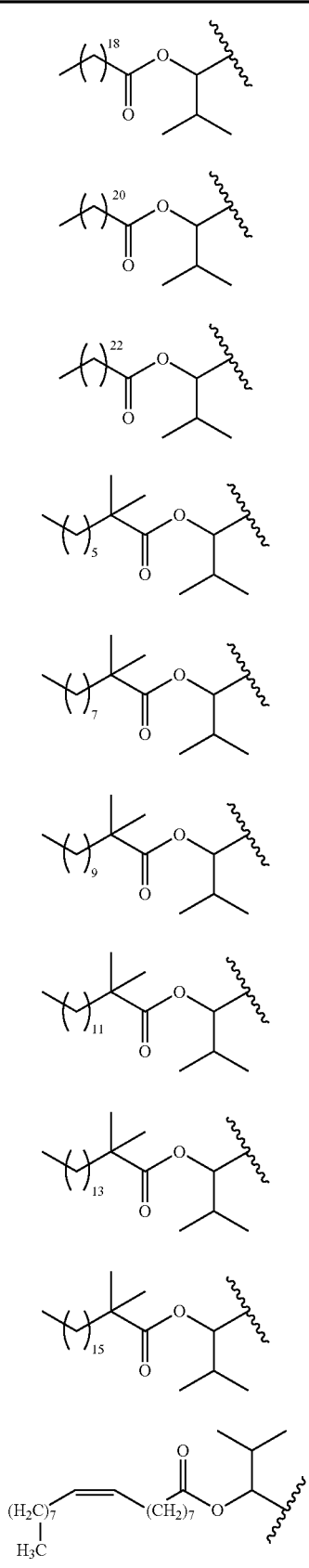

TABLE 1-continued
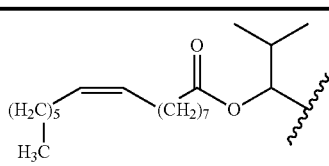
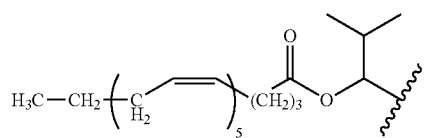
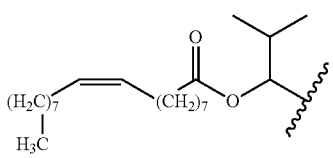
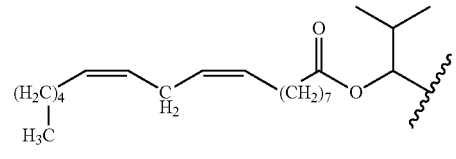
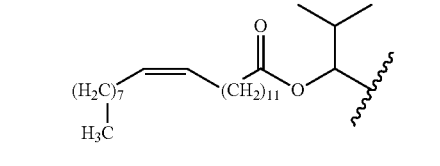
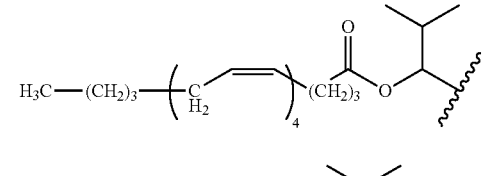
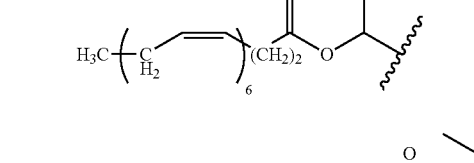
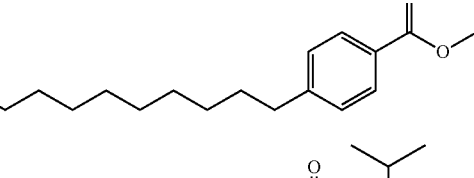
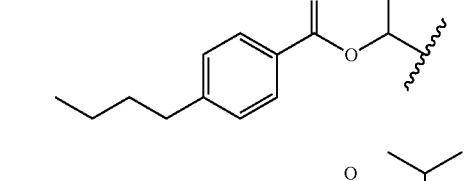
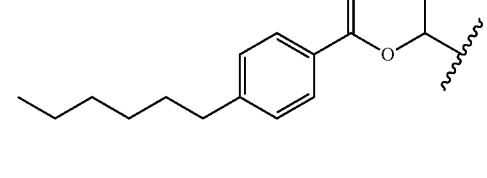
TABLE 1-continued
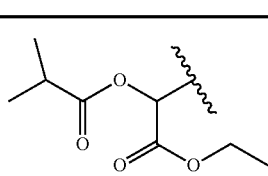
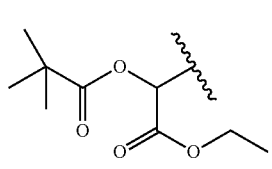 [SMILES: *C(OC(=O)C(C)(C)C)C(=O)OCC]
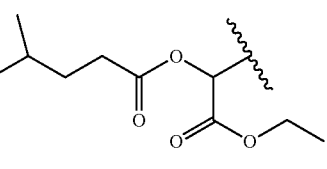
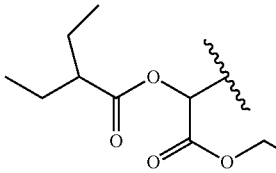
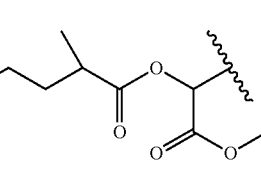
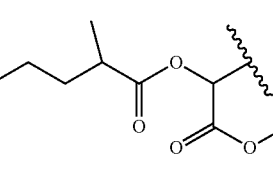
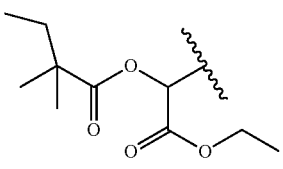 [SMILES: *C(OC(=O)C(C)(C)CC)C(=O)OCC]
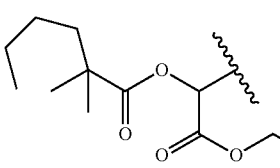
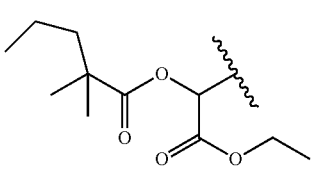 [SMILES: *C(OC(=O)C(C)(C)CCC)C(=O)OCC]

TABLE 1-continued
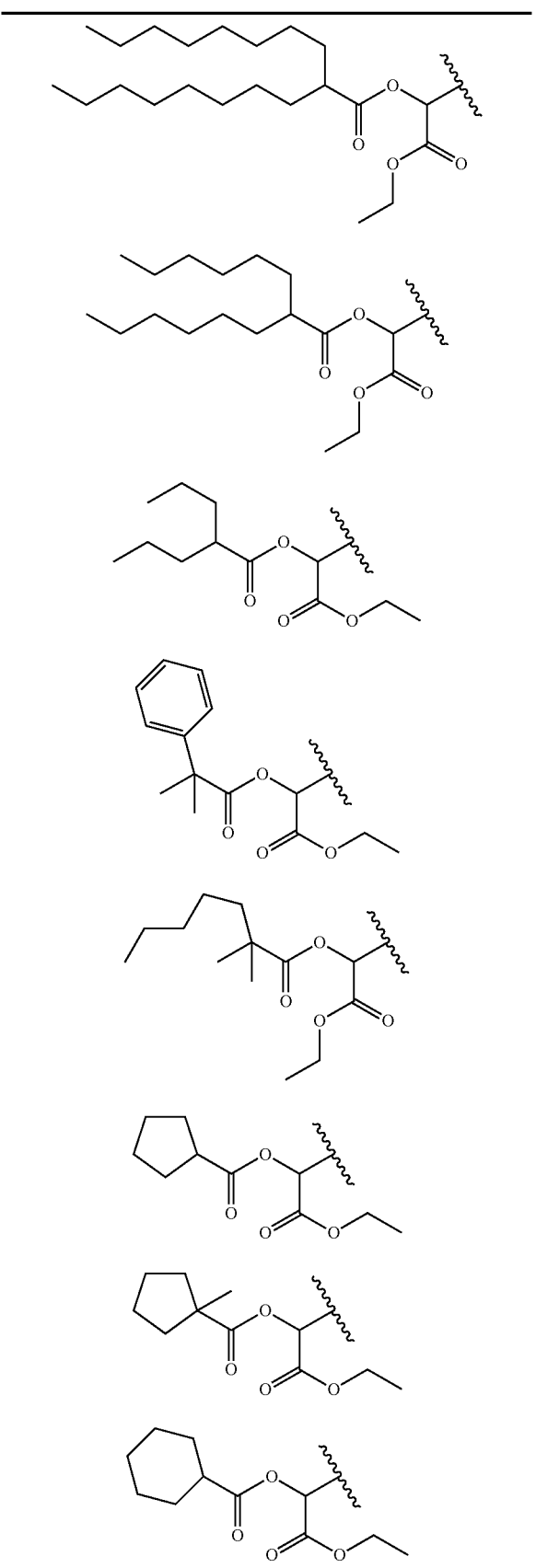
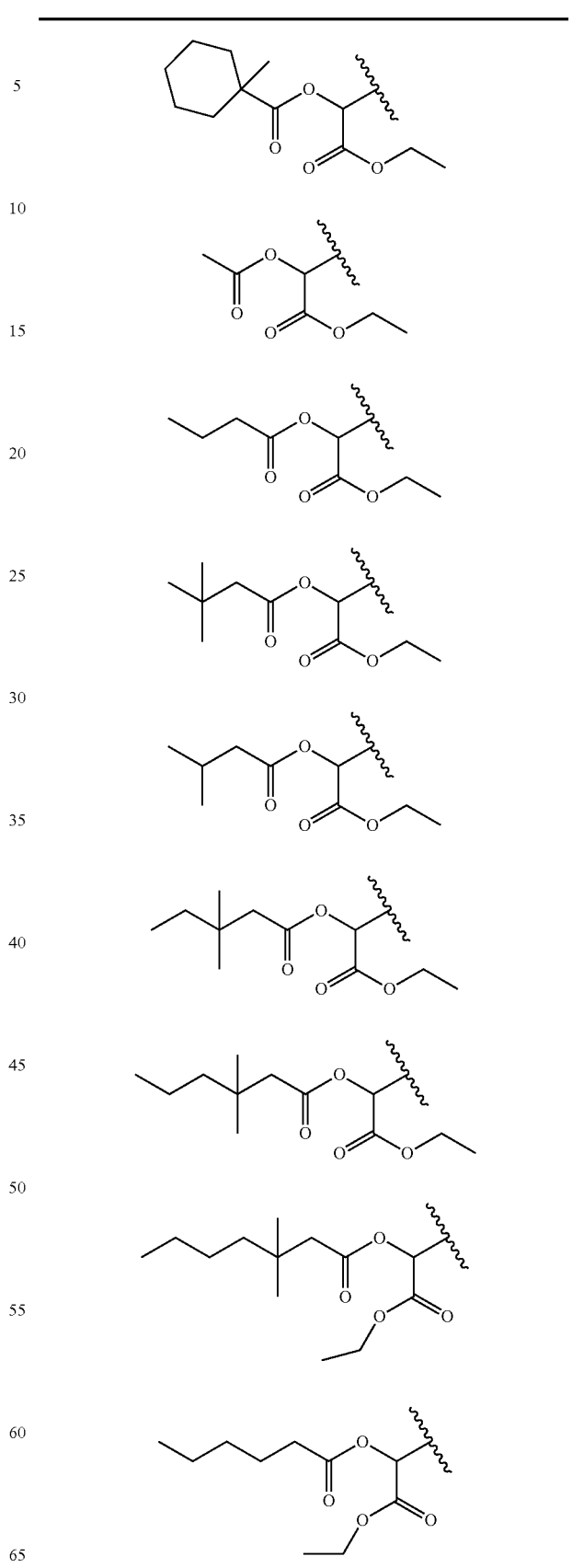

TABLE 1-continued
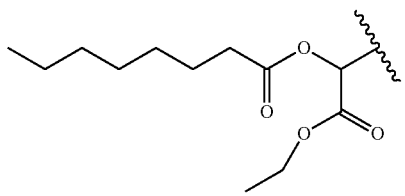 [SMILES: *C(OC(=O)CCCCCCC)C(=O)OCC]
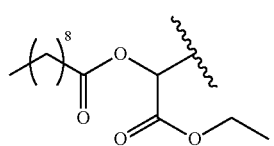
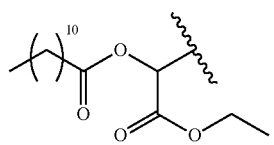
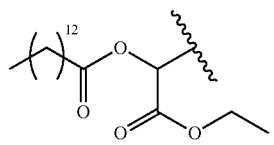
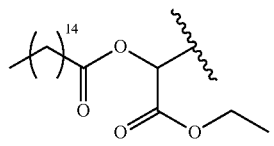
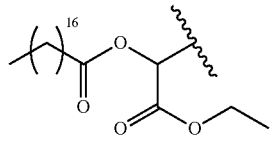
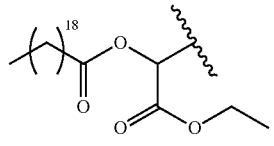
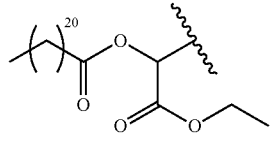
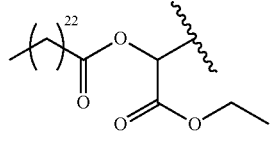
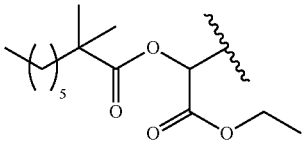
TABLE 1-continued
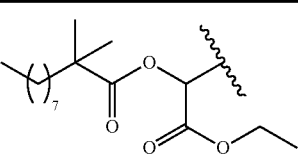
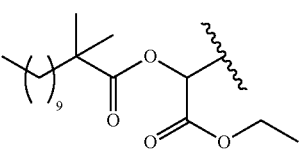
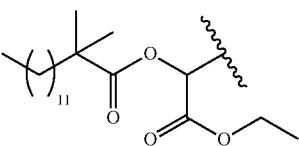
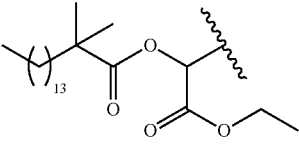
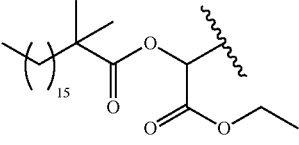
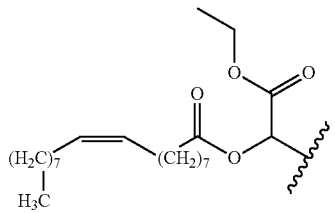
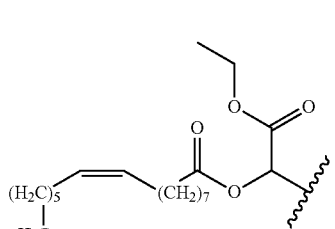
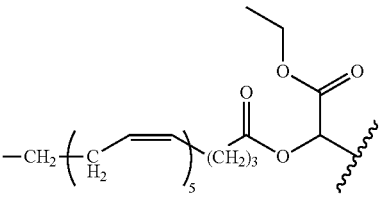

TABLE 1-continued
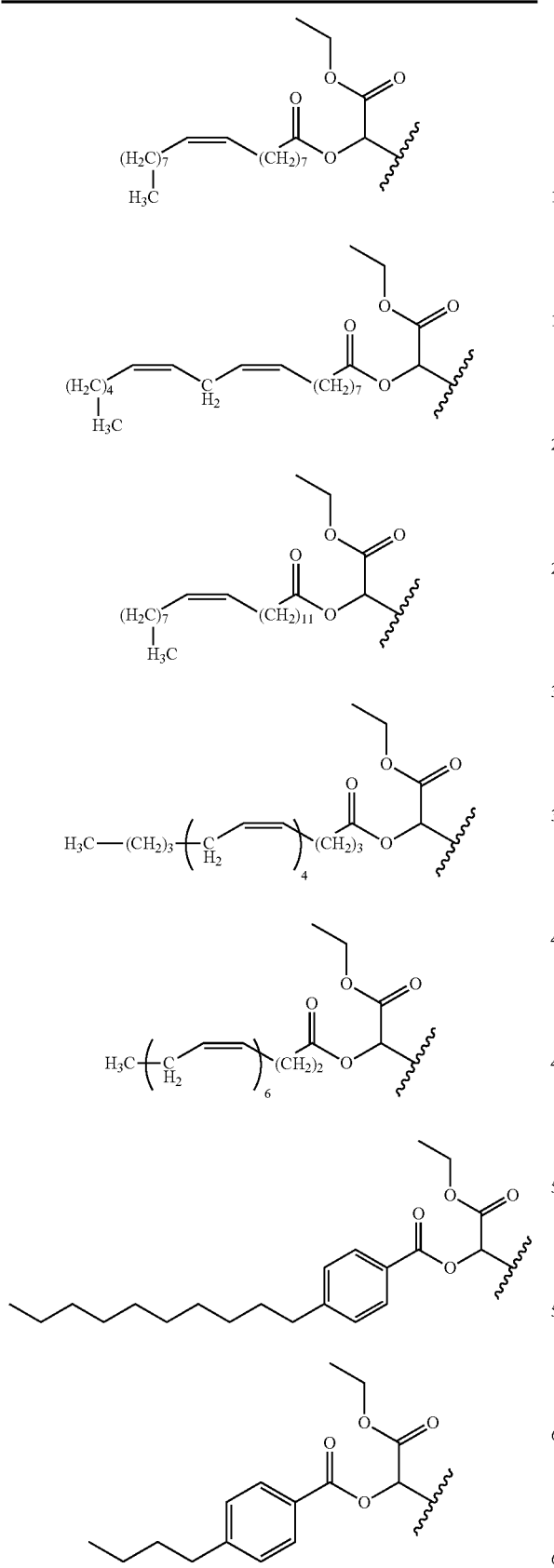
TABLE 1-continued
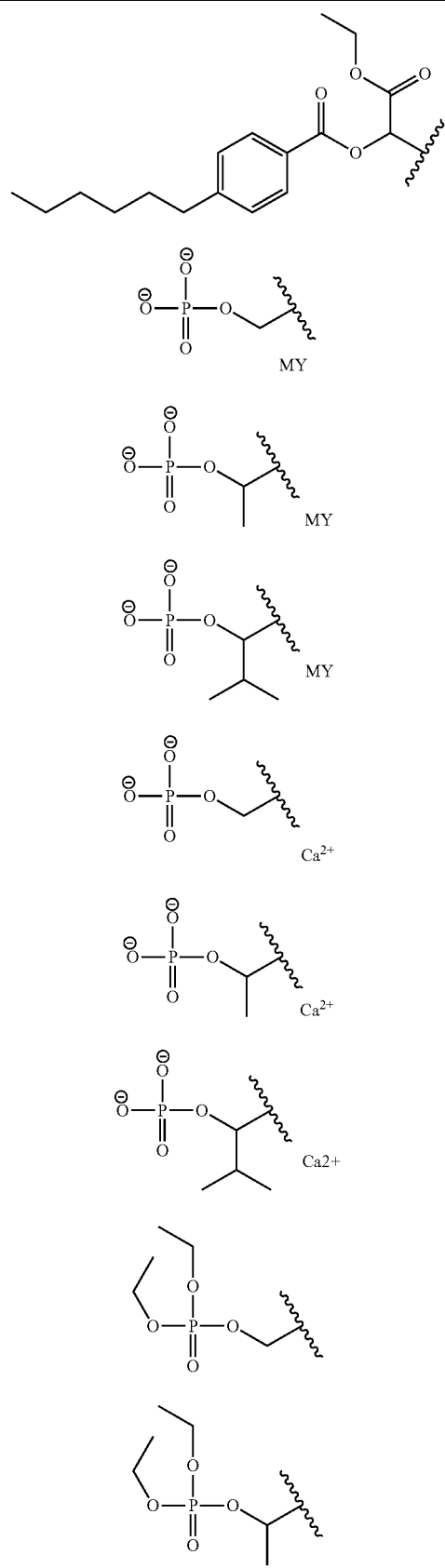

TABLE 1-continued
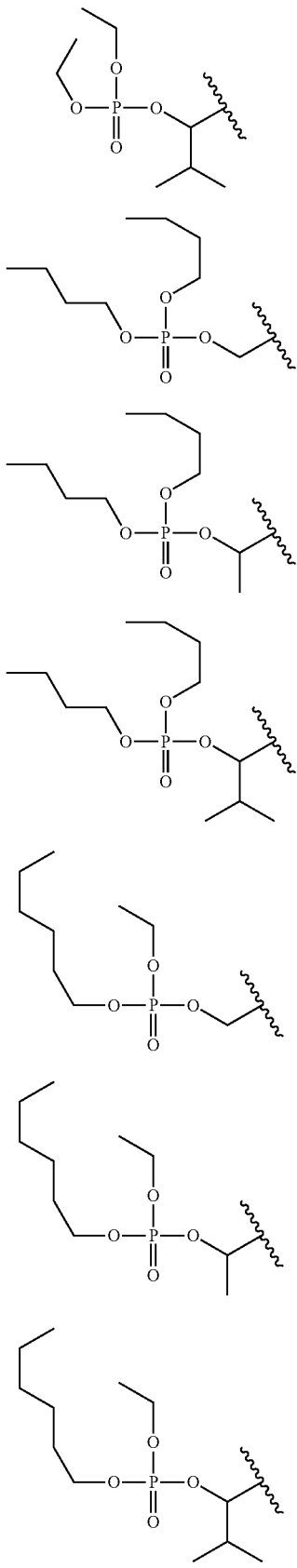
TABLE 1-continued
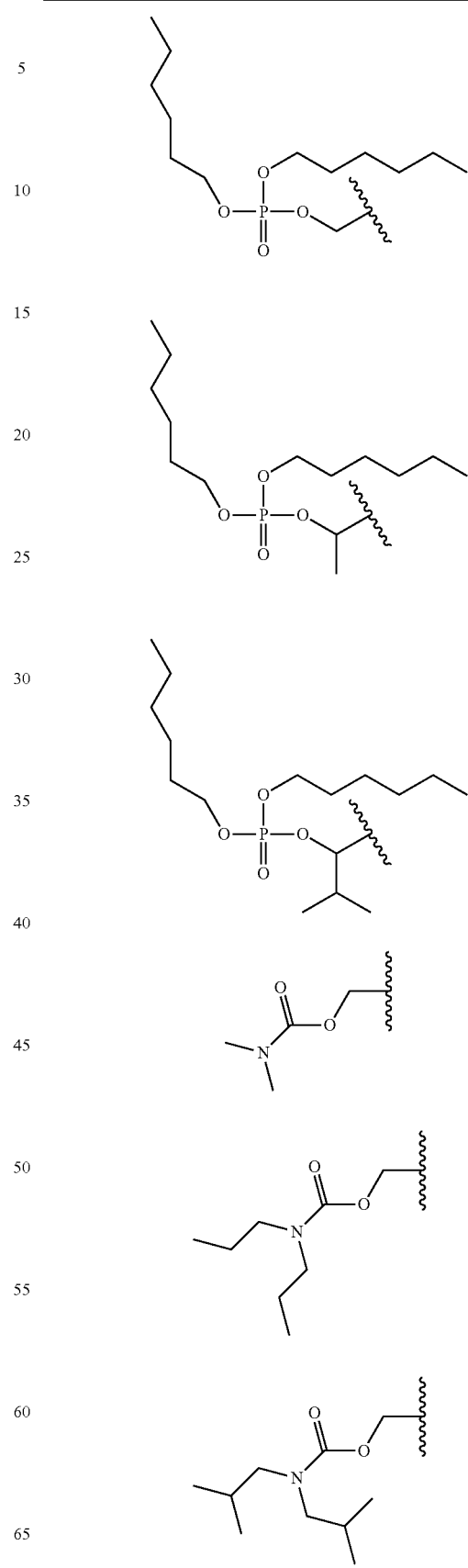

TABLE 1-continued
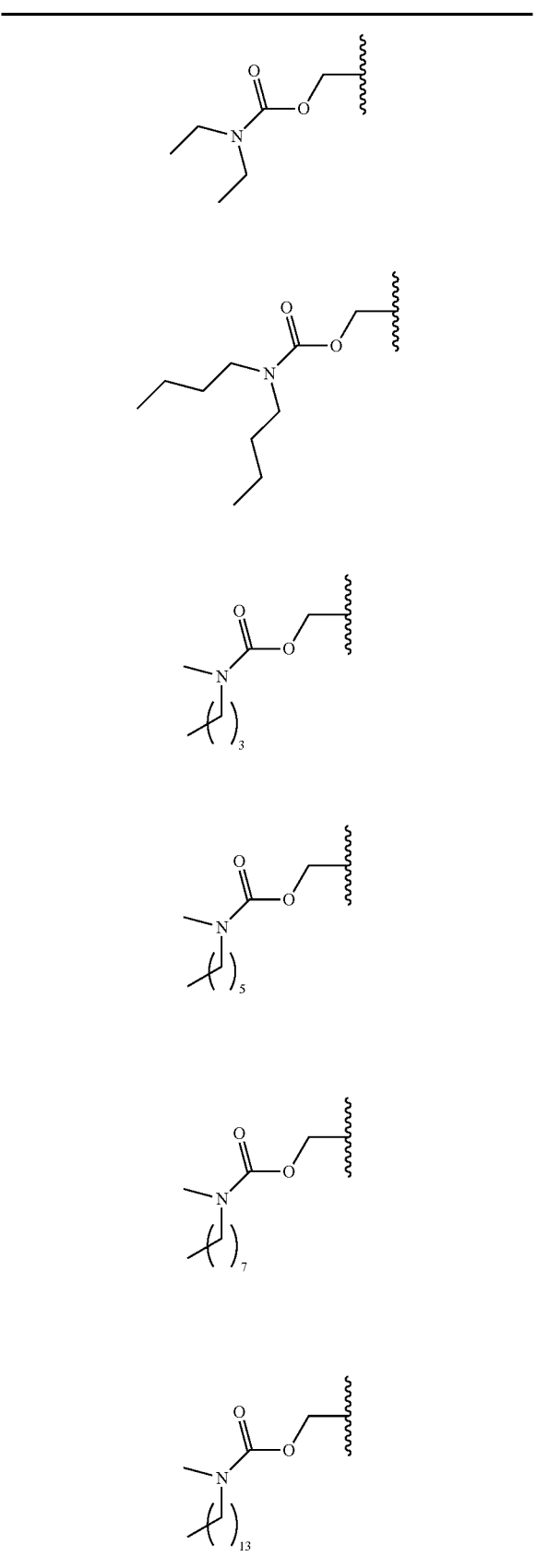
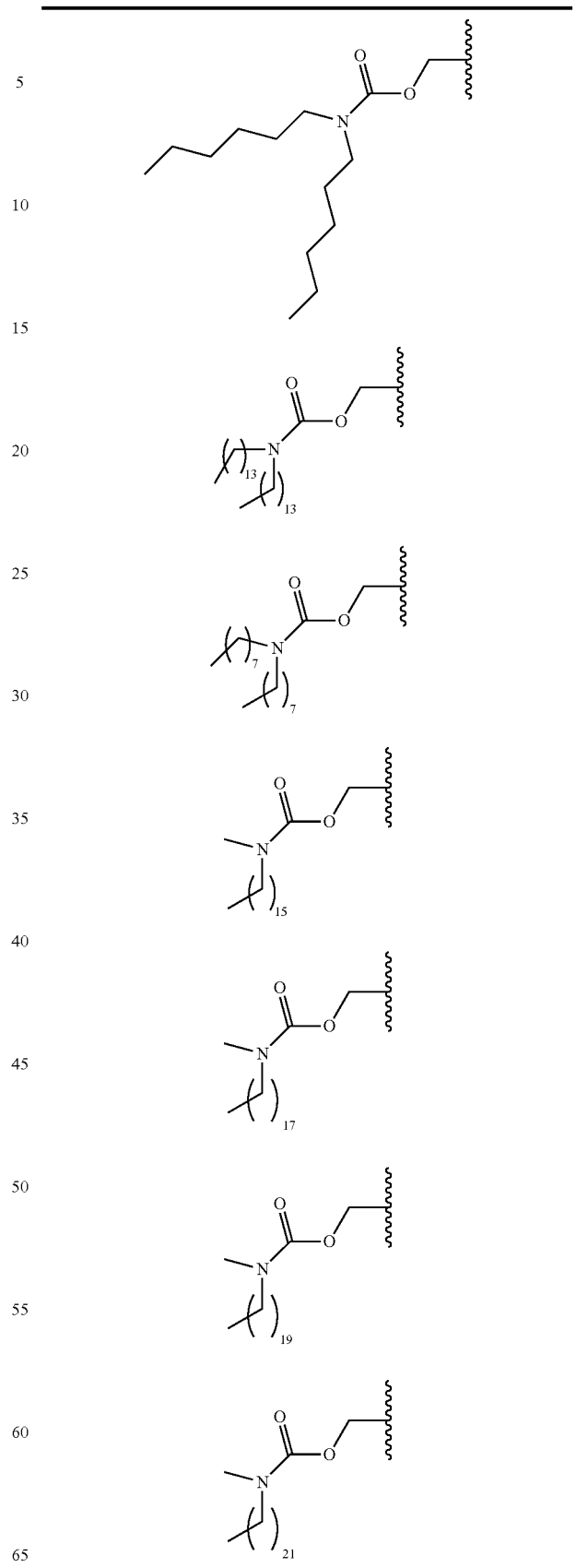

TABLE 1-continued
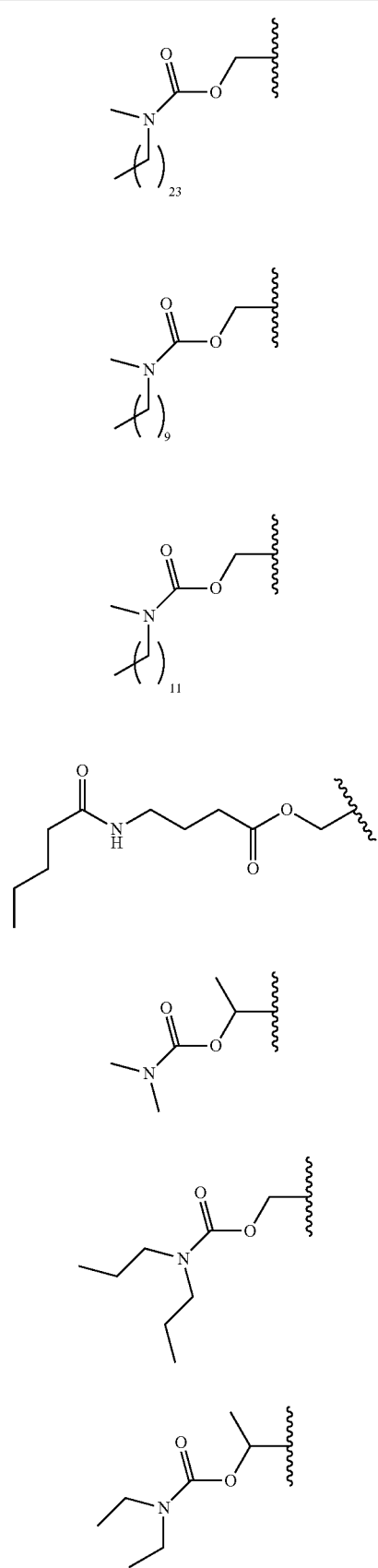
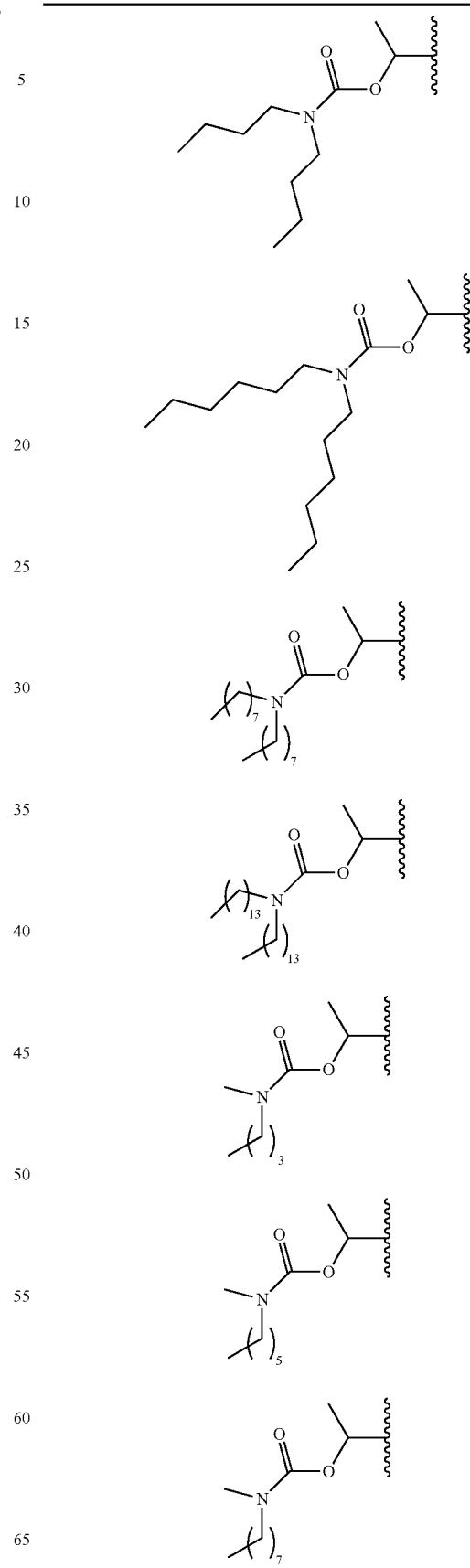

TABLE 1-continued
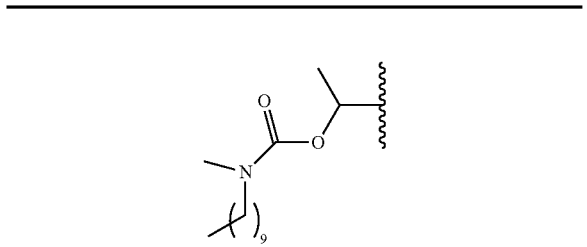
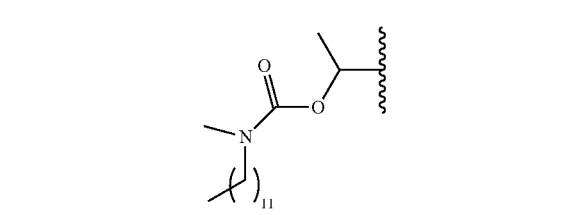
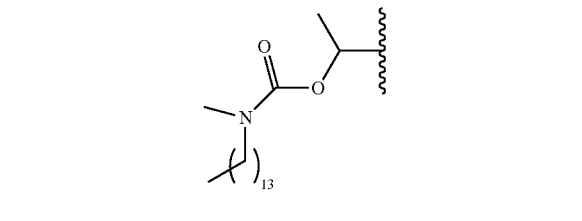
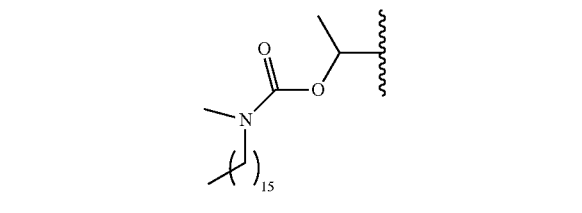
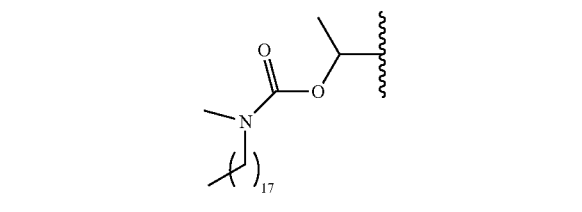
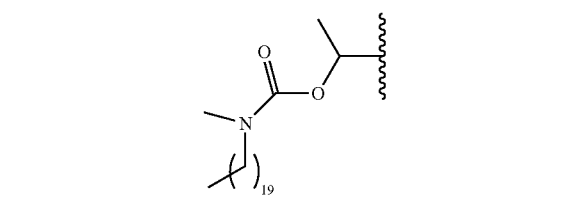
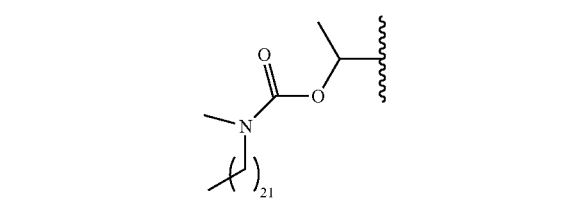
TABLE 1-continued
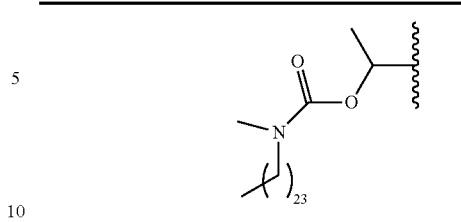
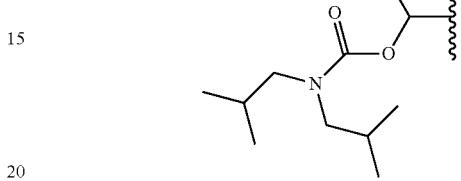
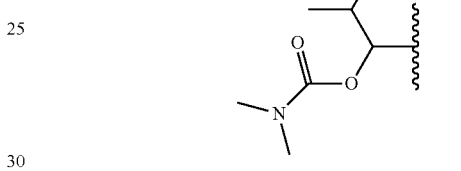
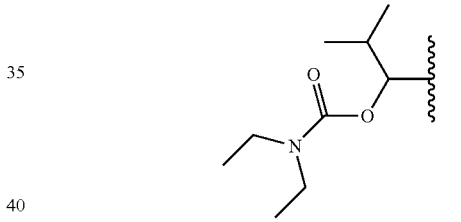
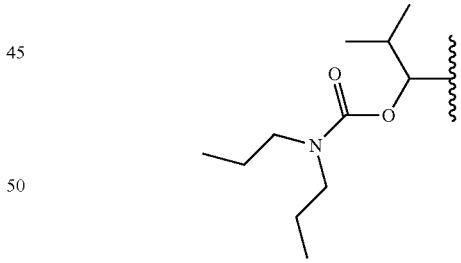
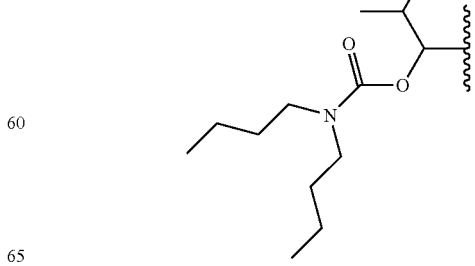

TABLE 1-continued
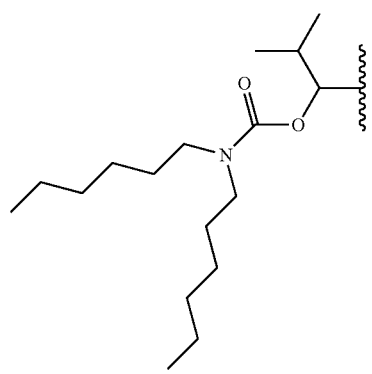 [SMILES: *C(OC(=O)N(CCCCCC)CCCCCC)C(C)C]
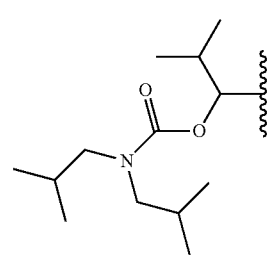 [SMILES: *C(OC(=O)N(CC(C)C)CC(C)C)C(C)C]
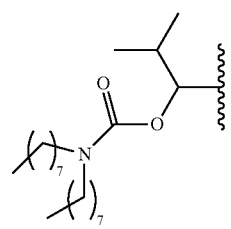
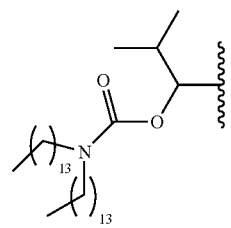
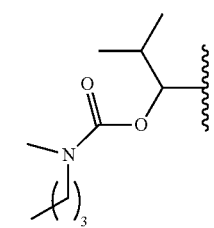
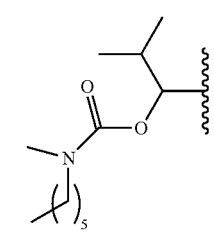
TABLE 1-continued
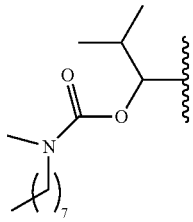
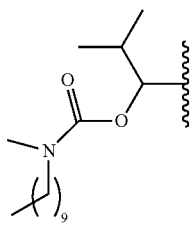
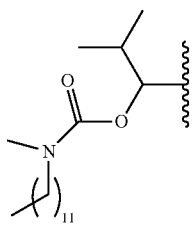
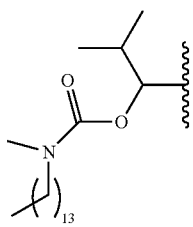
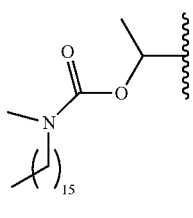
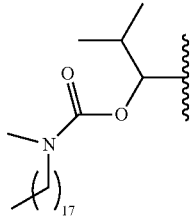
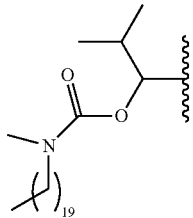

TABLE 1-continued
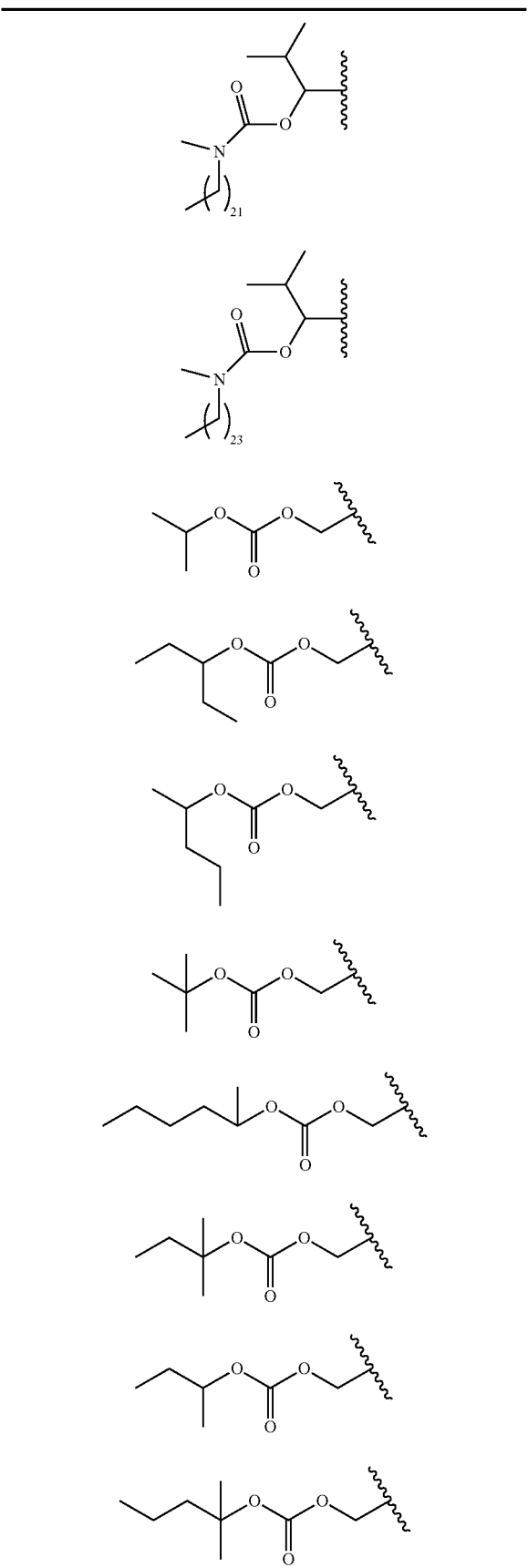
TABLE 1-continued
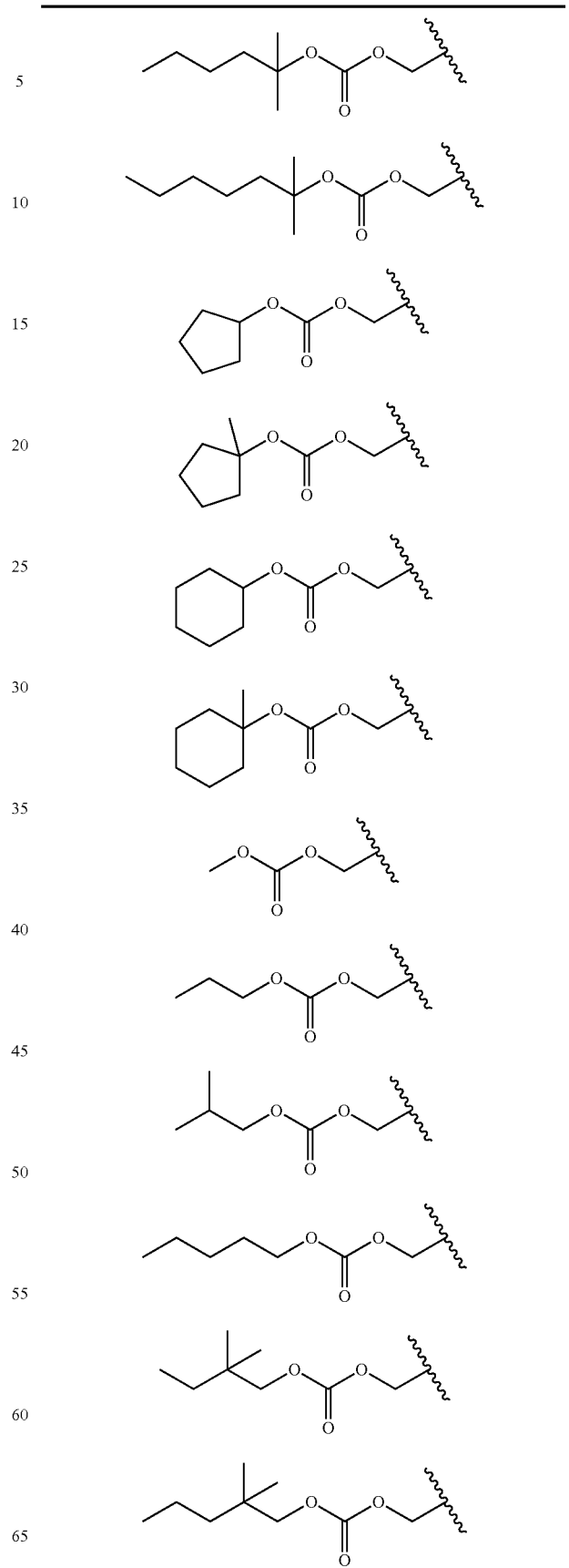

TABLE 1-continued
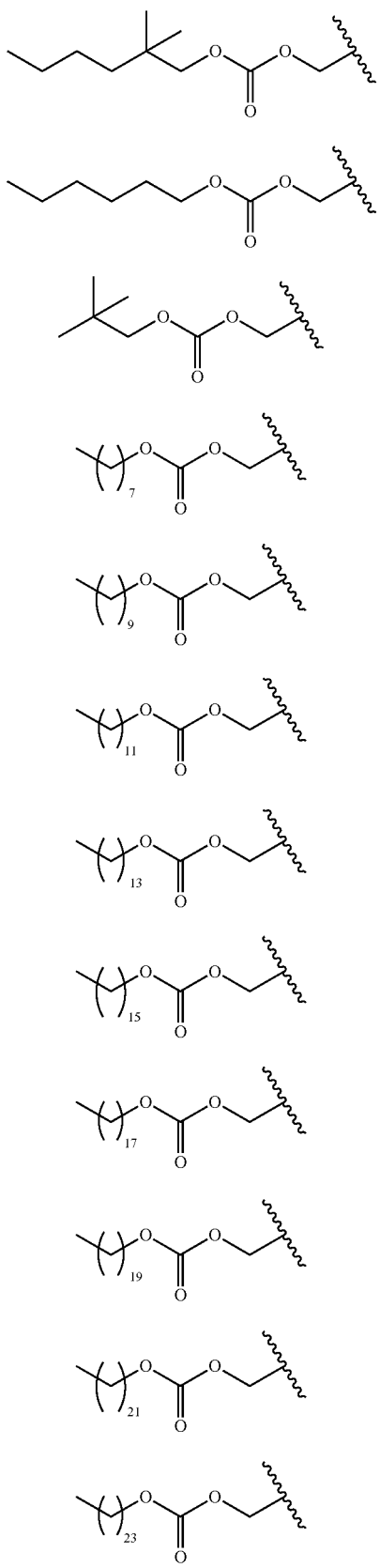
TABLE 1-continued
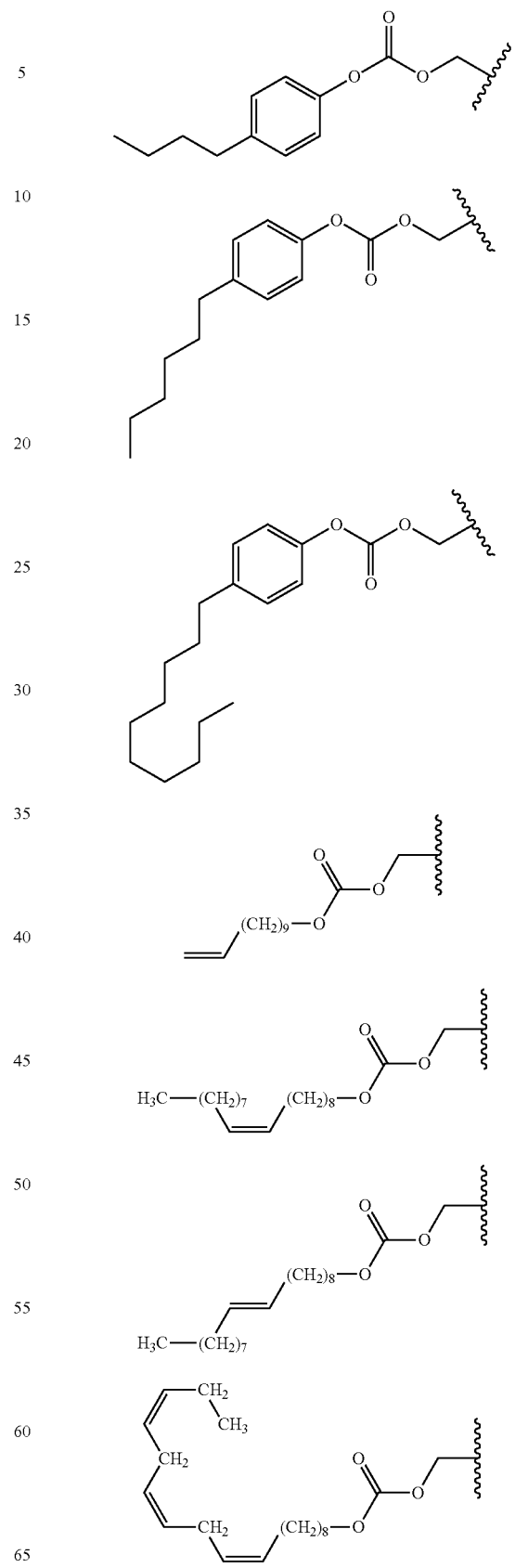

TABLE 1-continued

TABLE 1-continued
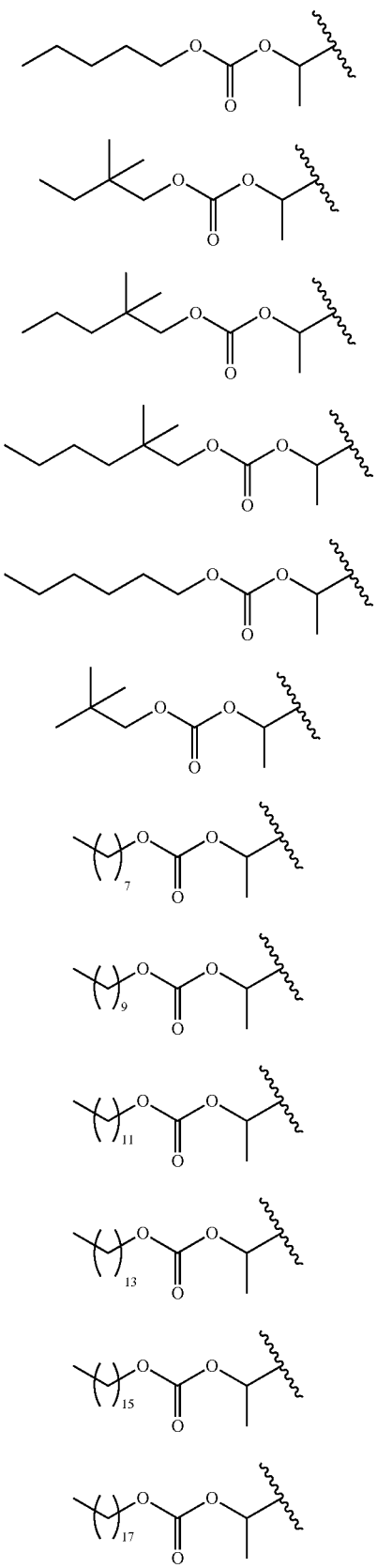
TABLE 1-continued
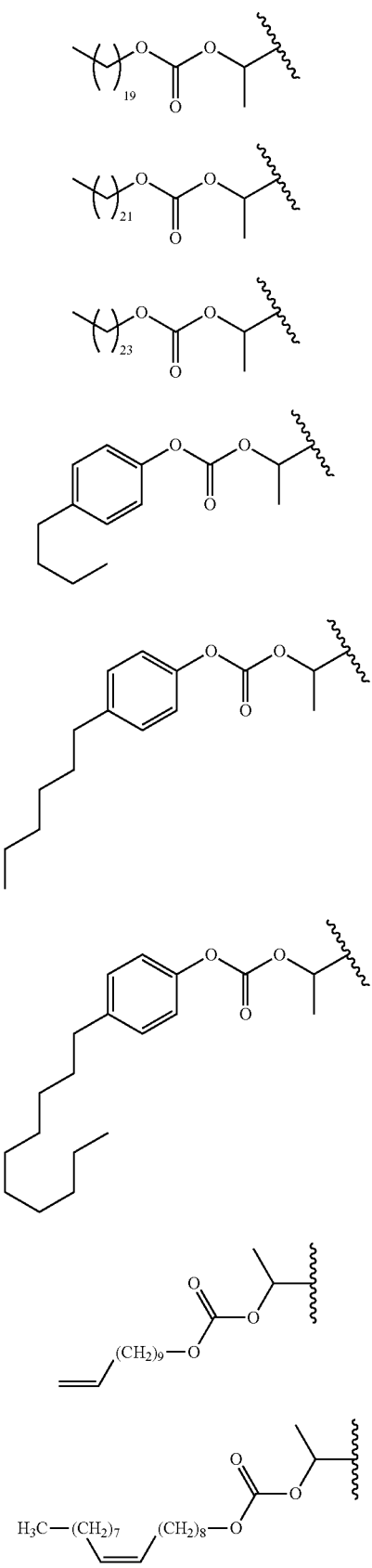

TABLE 1-continued
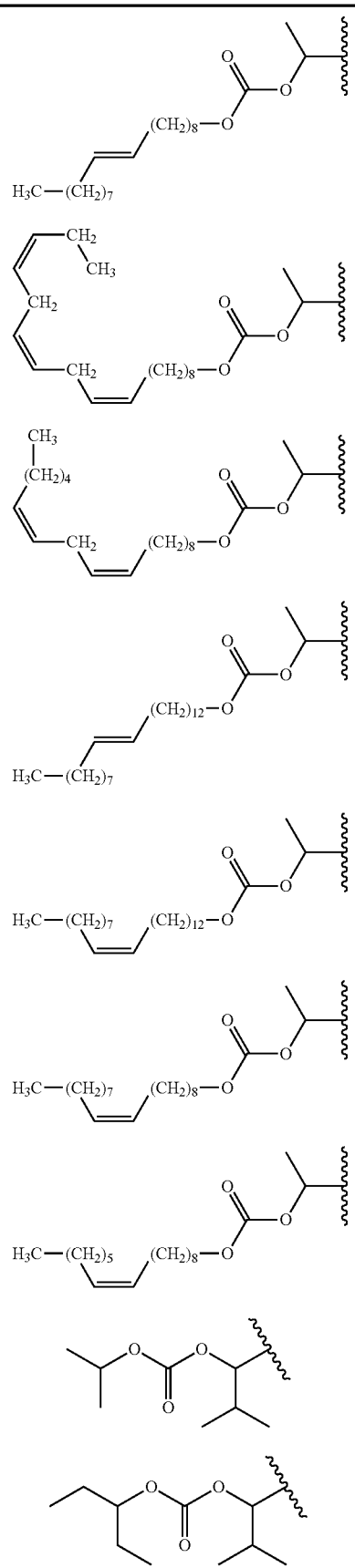
TABLE 1-continued
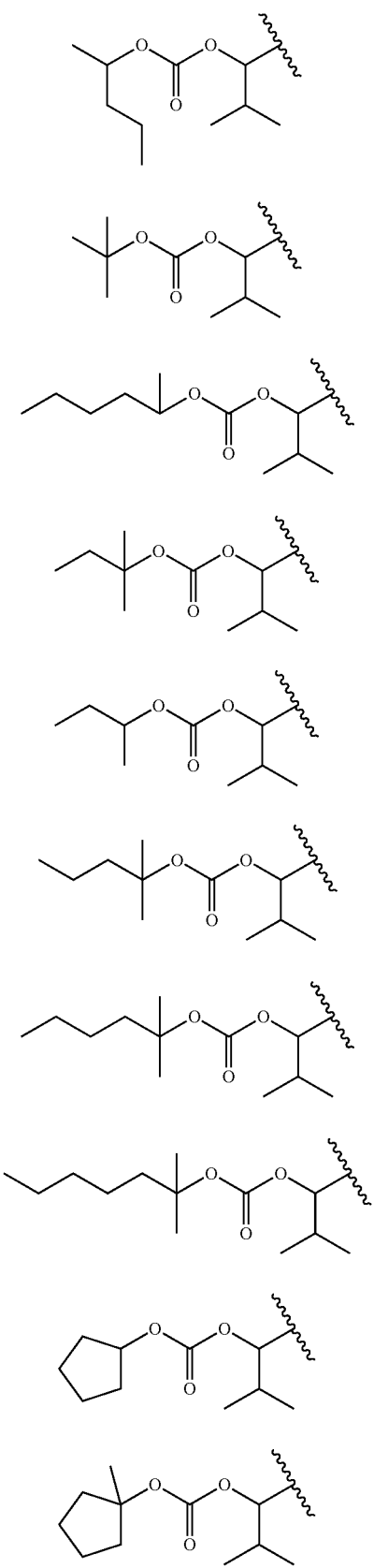

TABLE 1-continued
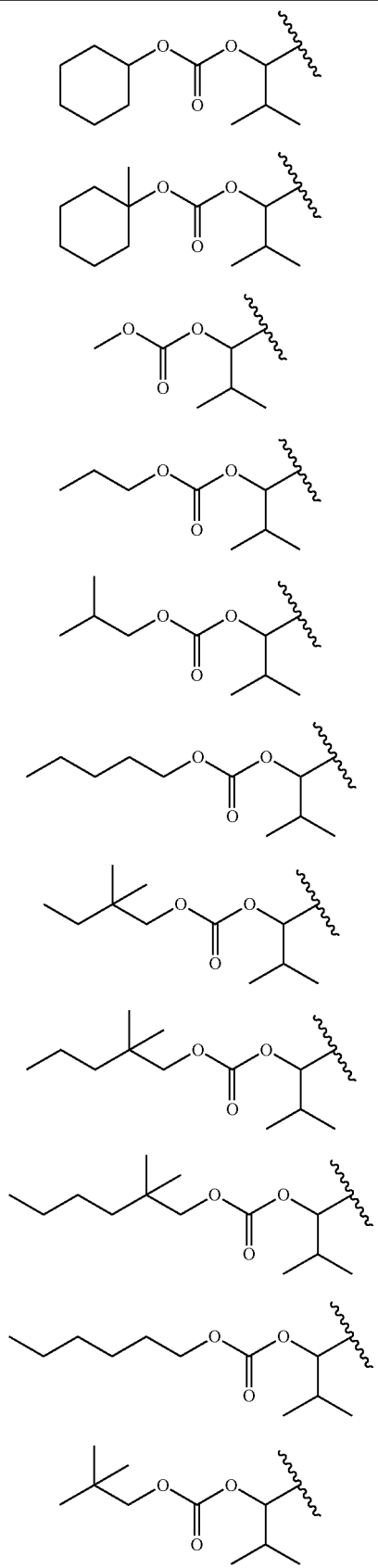
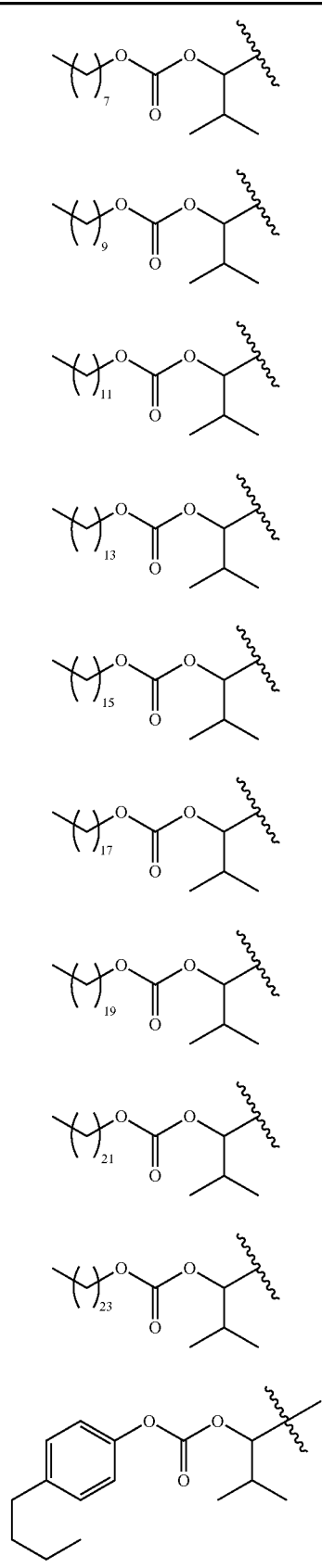

TABLE 1-continued
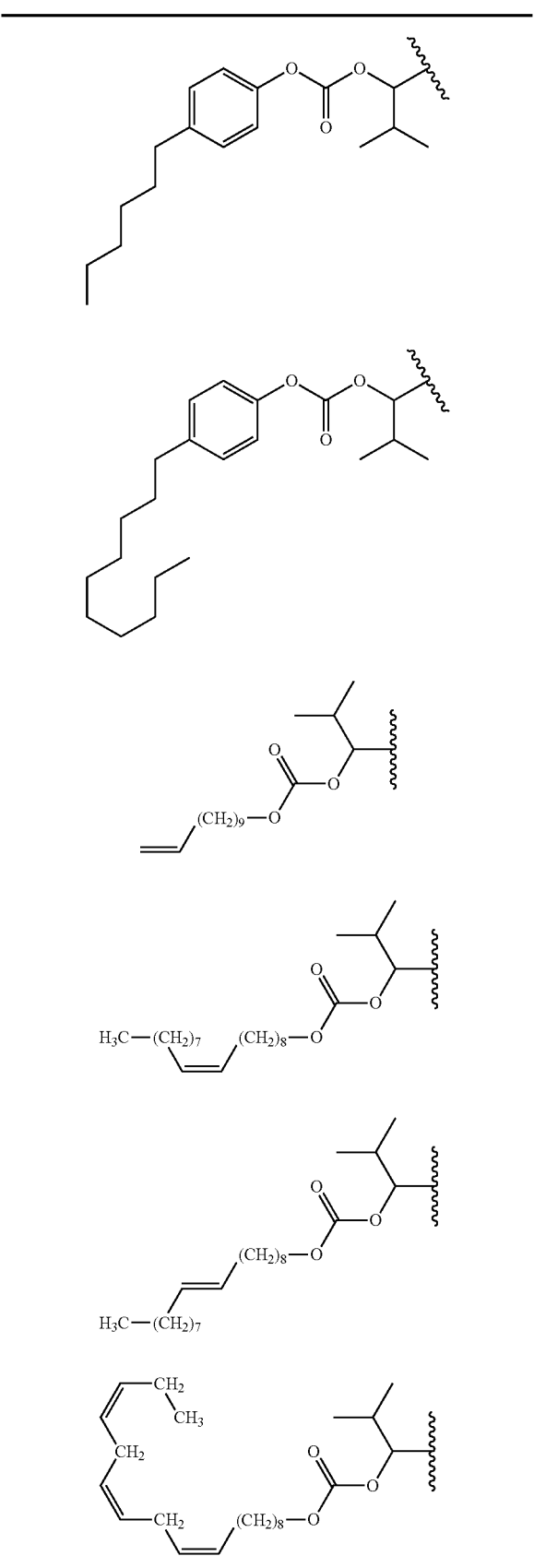
TABLE 1-continued
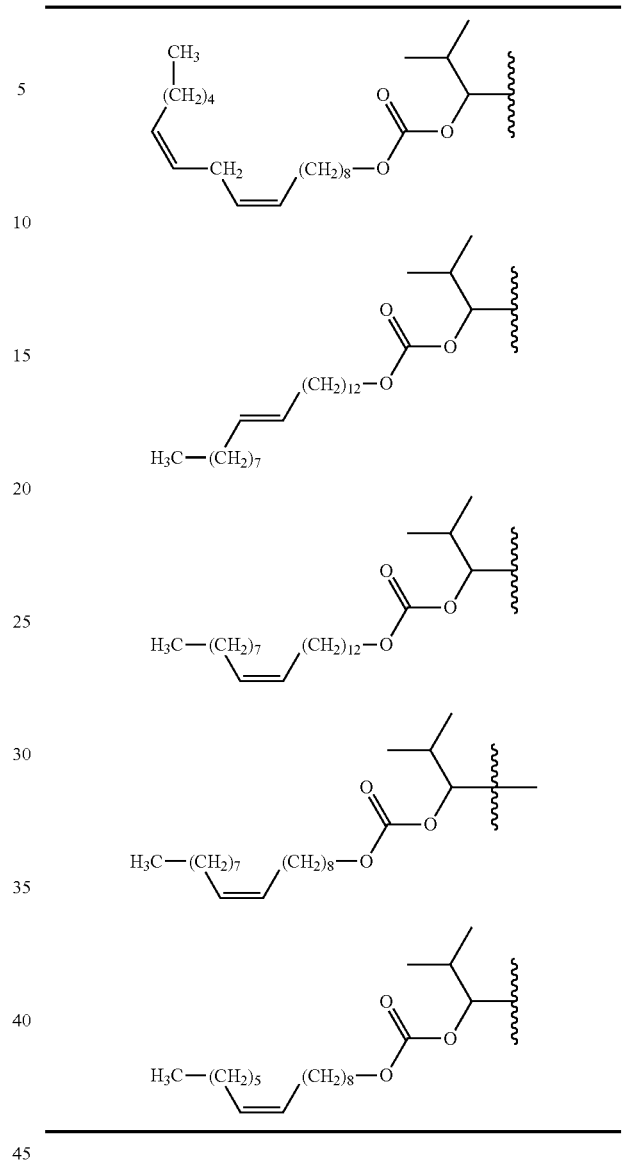
In a more preferred embodiment, $R_1$ is selected from Table 2.
TABLE 2
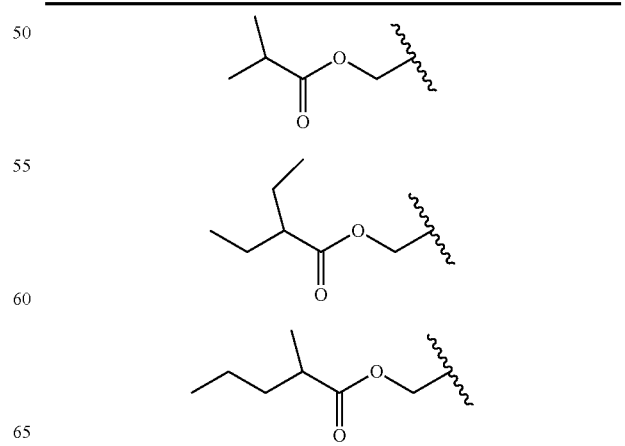

TABLE 2-continued
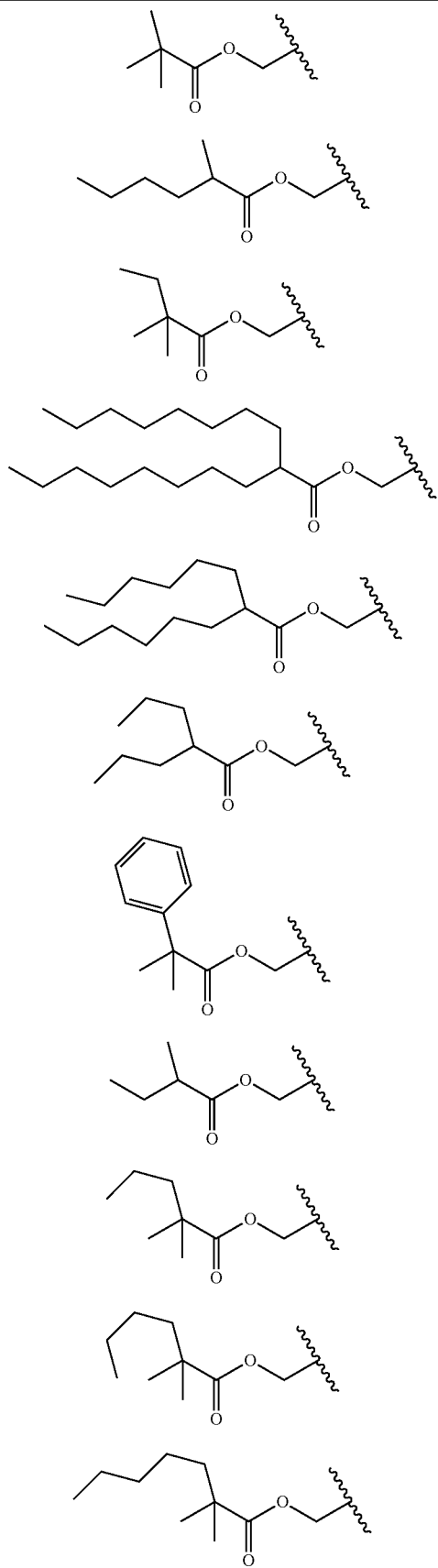
TABLE 2-continued
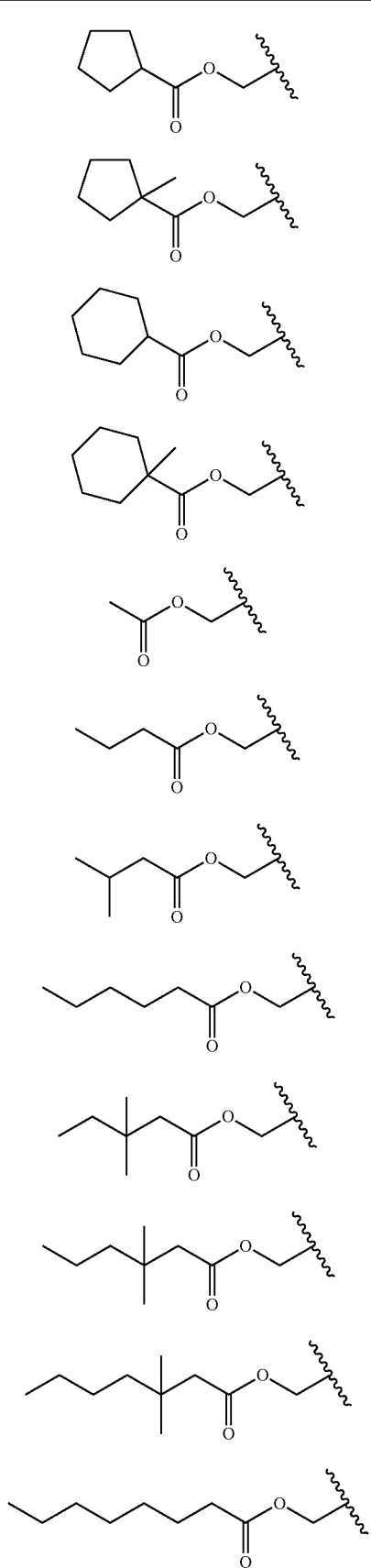

TABLE 2-continued
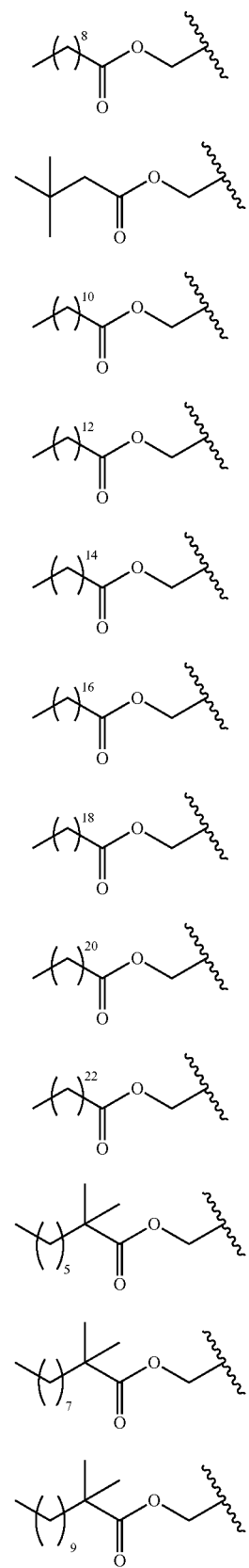
TABLE 2-continued
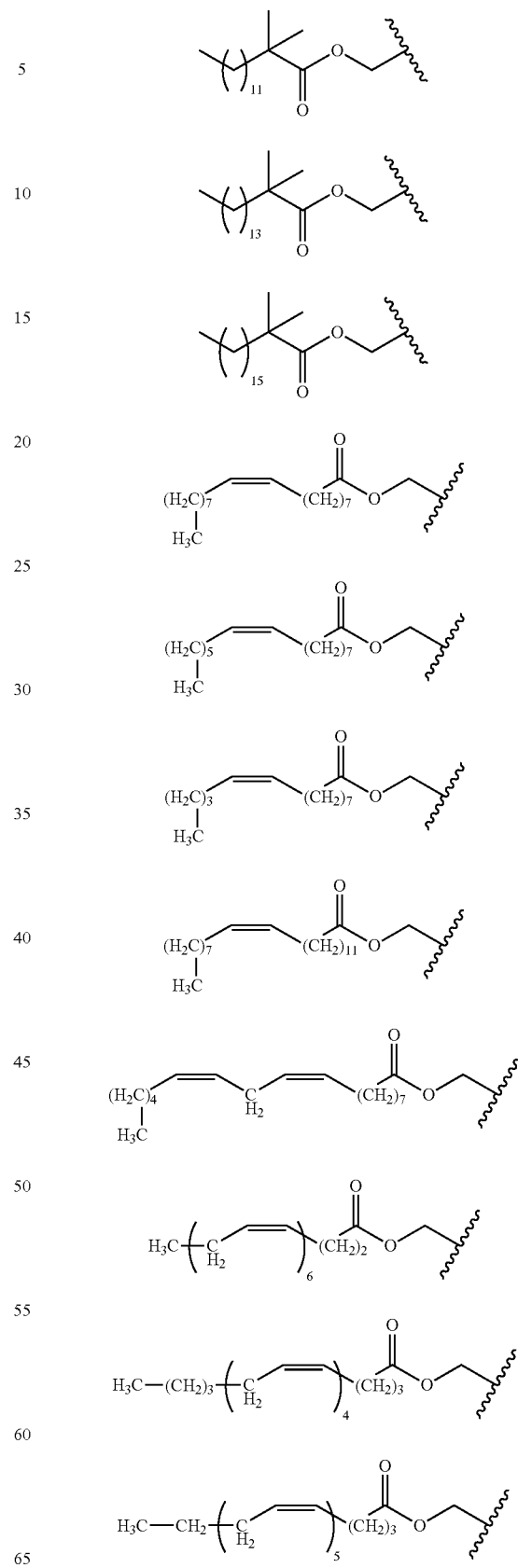

TABLE 2-continued
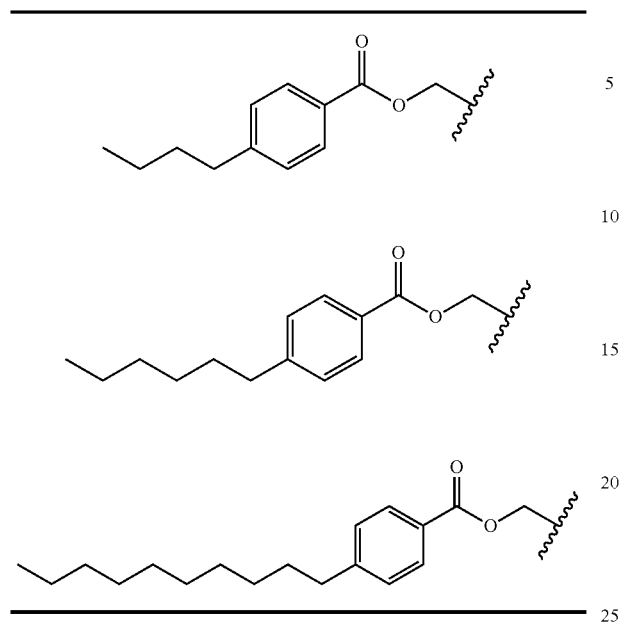
In a more preferred embodiment, $R_1$ is selected from Table 3.
TABLE 3
TABLE 3-continued
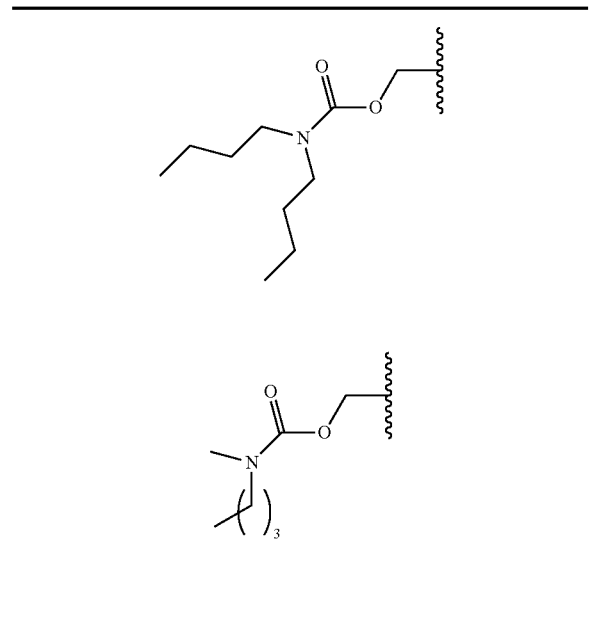
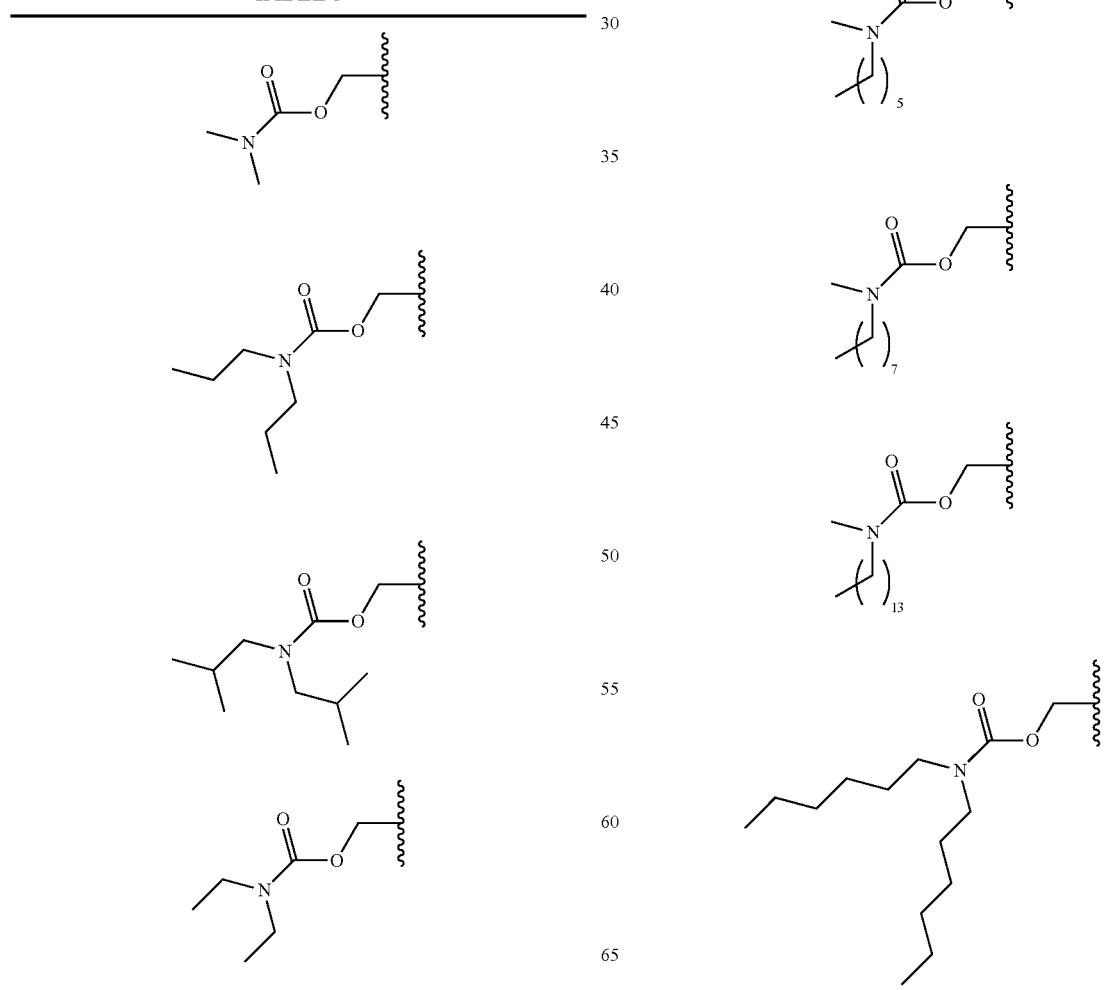

TABLE 3-continued
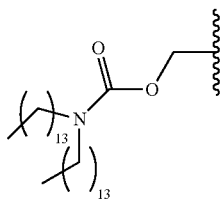
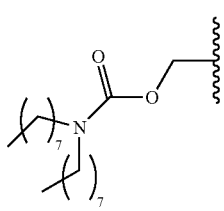
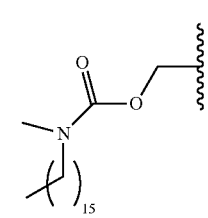
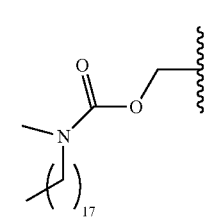
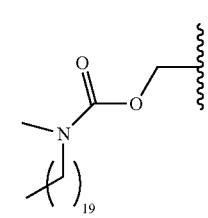
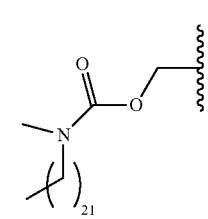
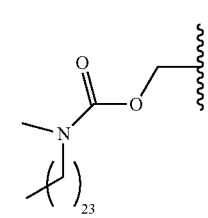
TABLE 3-continued
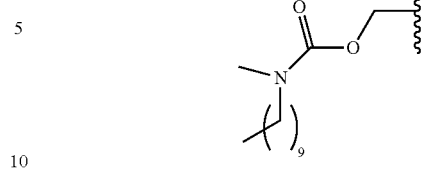
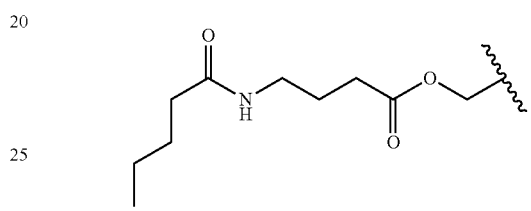
In a more preferred embodiment, $R_1$ is selected from Table 4.
TABLE 4
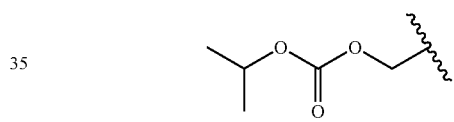
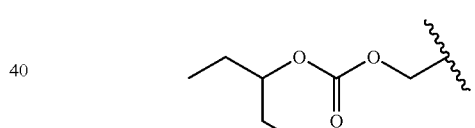
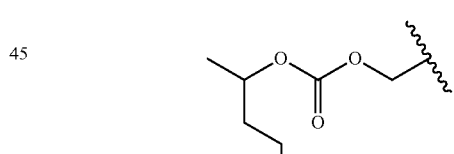
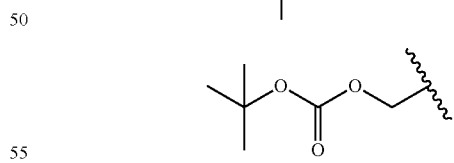
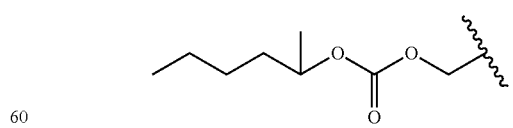
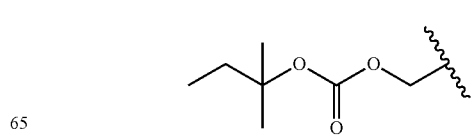

TABLE 4-continued
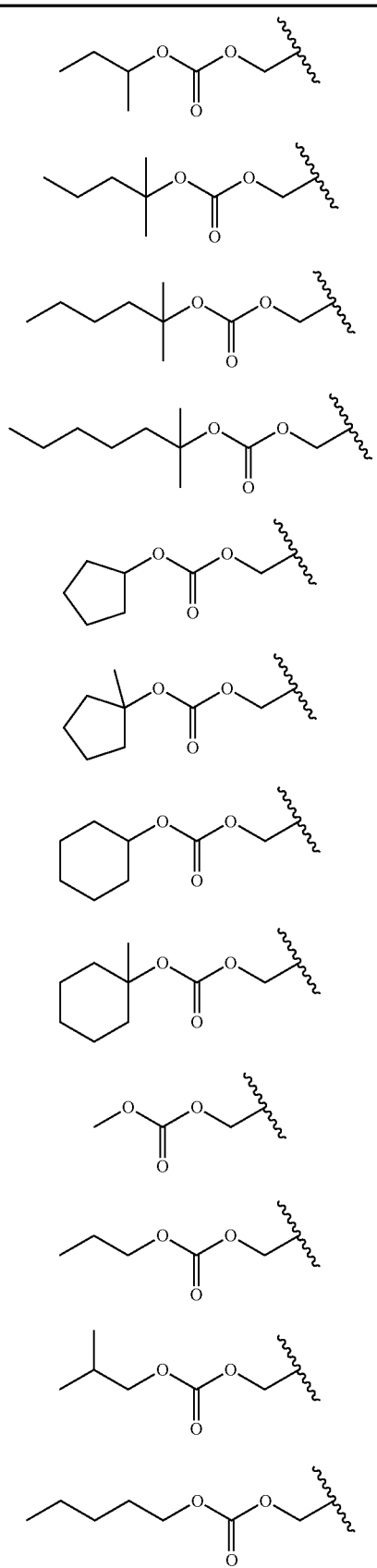
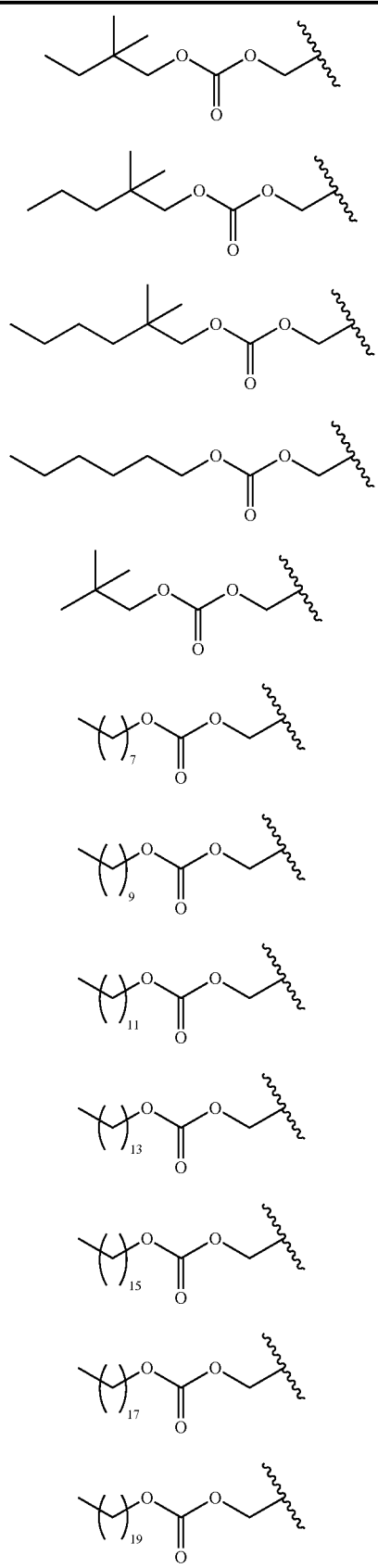

TABLE 4-continued
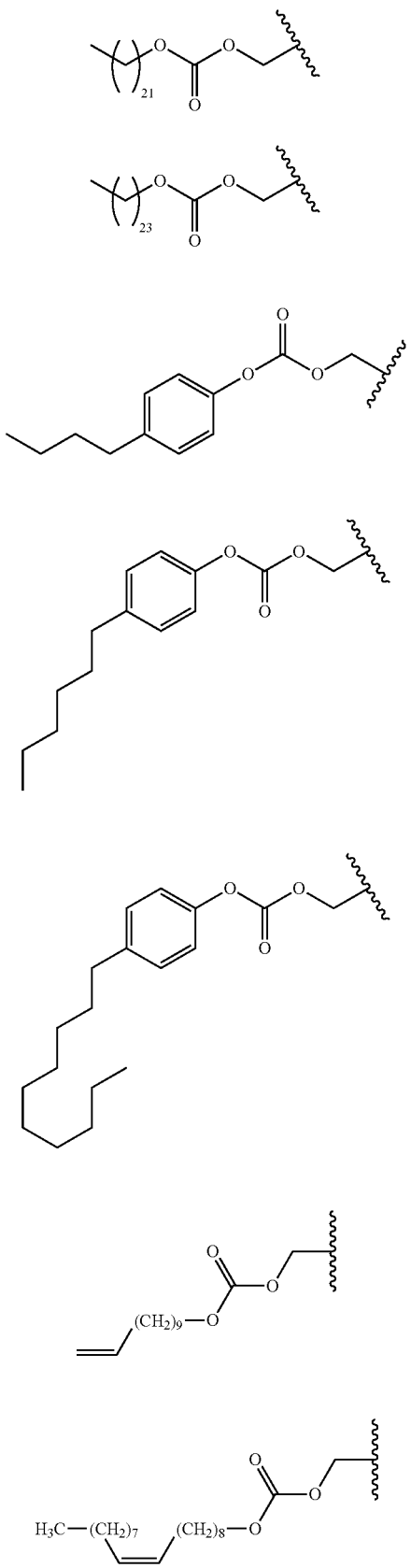
TABLE 4-continued
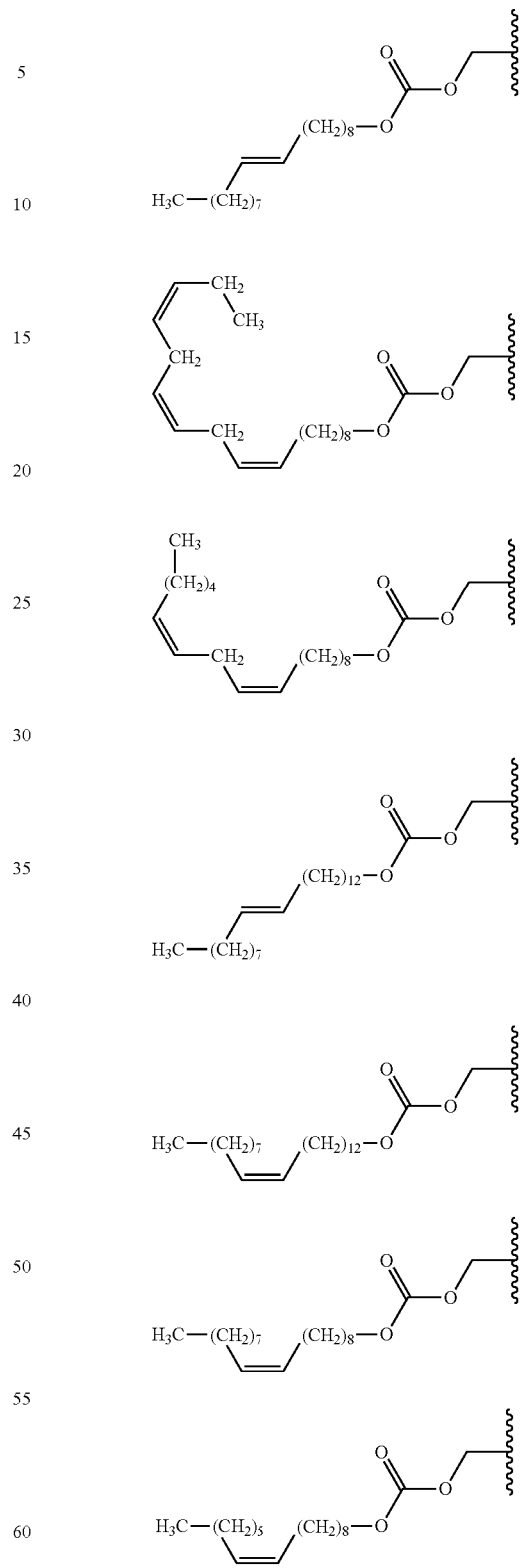
In a preferred embodiment, a compound of Formula VA selected from Table A is oxidized by reacting with DDQ in the presence of an acid to give the corresponding dehydrogenated compound of Formula V.

TABLE A
| No | Structure |
|---|---|
| 1 | 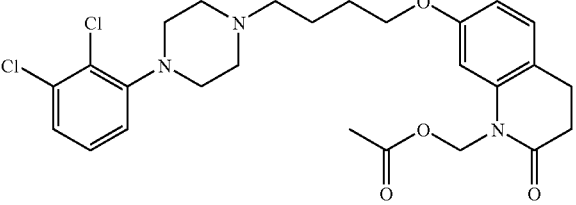 |
| 2 | 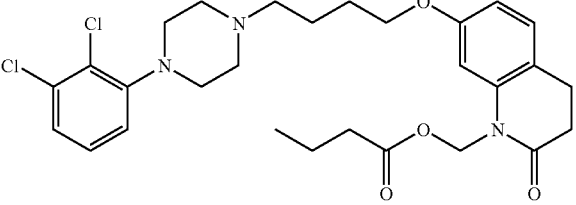 |
| 3 | 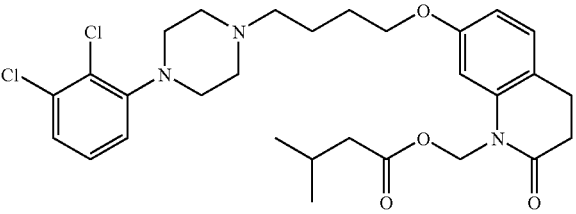 [SMILES: CC(C)CC(=O)OCN1C(=O)CCc2ccc(OCCCCN3CCN(c4cccc(Cl)c4Cl)CC3)cc21] |
| 4 | 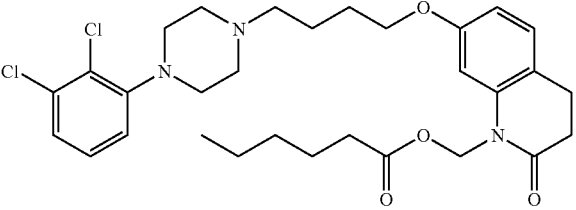 [SMILES: CCCCCC(=O)OCN1C(=O)CCc2ccc(OCCCCN3CCN(c4cccc(Cl)c4Cl)CC3)cc21] |
| 5 | 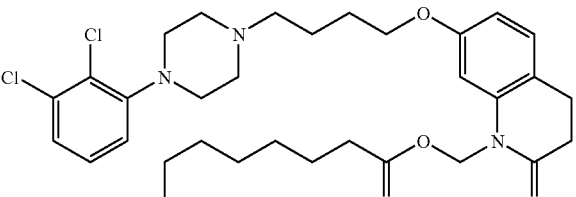 |
| 6 | 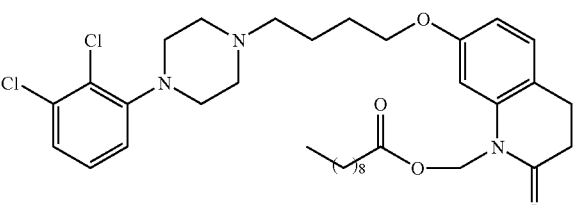 |
| 7 | 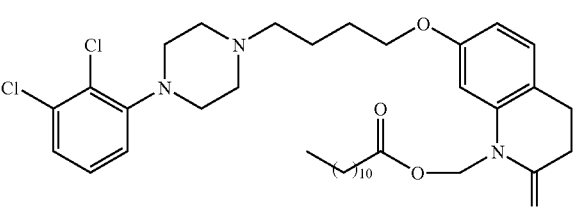 |

TABLE A-continued

| No | Structure |
|---|---|
| 8 | (structure) |
| 9 | (structure) |
| 10 | (structure) |
| 11 | (structure) |
| 12 | (structure) |
| 13 | (structure) |
| 14 | (structure) |

TABLE A-continued
| No | Structure |
|---|---|
| 15 | 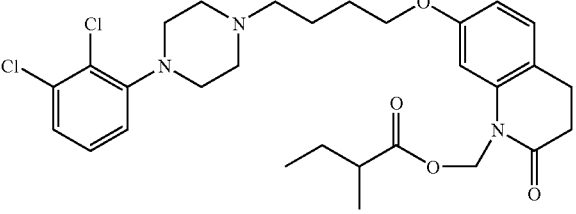 |
| 16 | 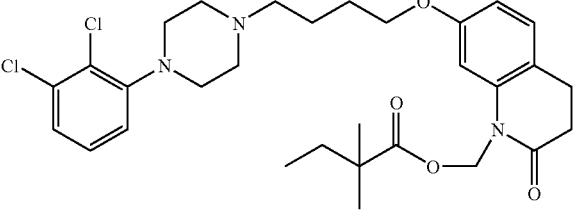 |
| 17 | 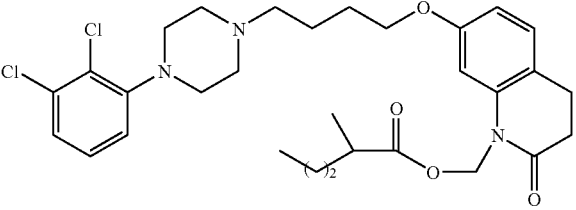 |
| 18 | 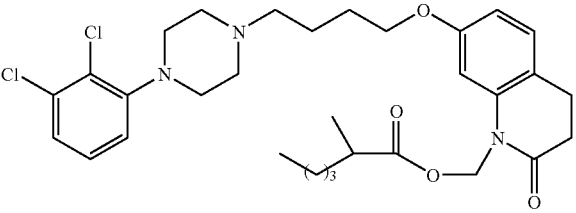 |
| 19 | 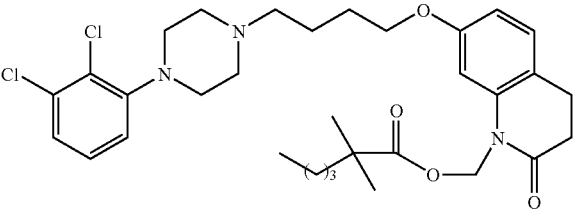 |
| 20 | 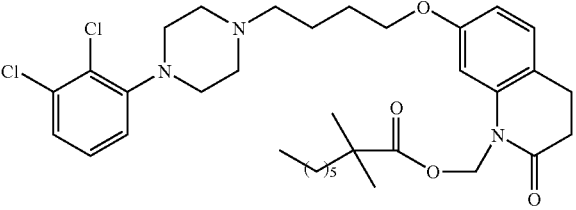 |
| 21 | 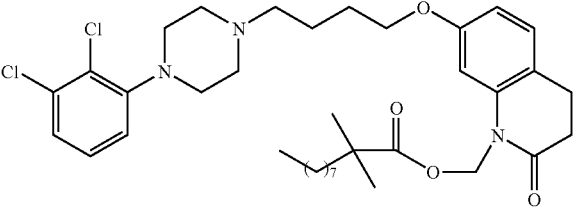 |

TABLE A-continued
| No | Structure |
|---|---|
| 22 | 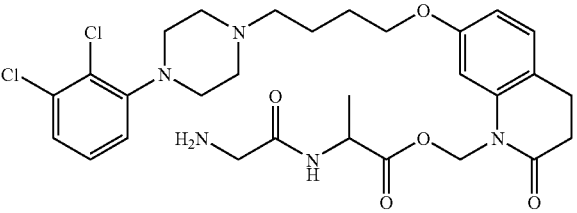 |
| 23 | 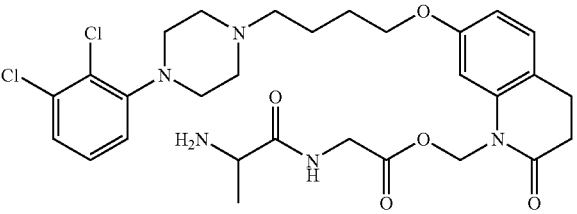 |
| 24 | 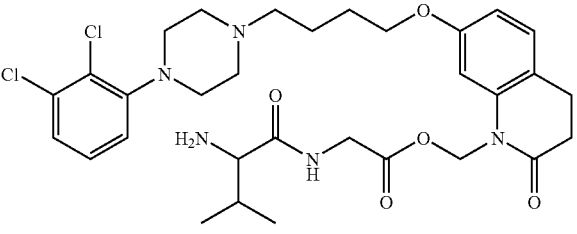 [SMILES: CC(C)C(N)C(=O)NCC(=O)OCN1C(=O)CCc2ccc(OCCCCN3CCN(c4cccc(Cl)c4Cl)CC3)cc21] |
| 25 | 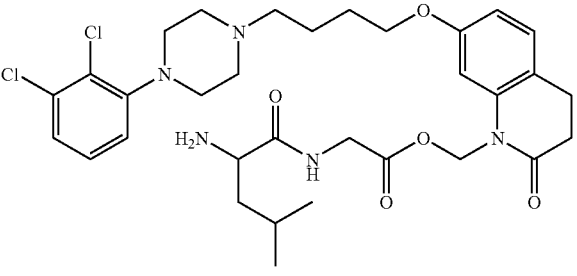 [SMILES: CC(C)CC(N)C(=O)NCC(=O)OCN1C(=O)CCc2ccc(OCCCCN3CCN(c4cccc(Cl)c4Cl)CC3)cc21] |
| 26 | 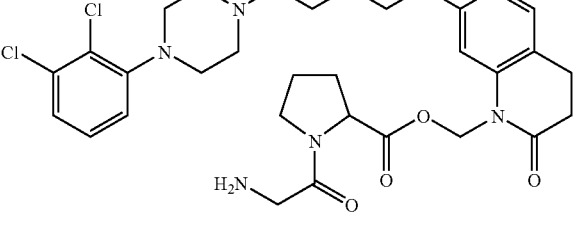 |
| 27 | 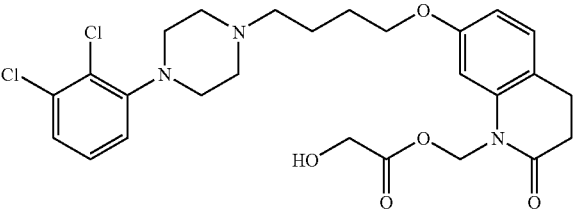 [SMILES: O=C(CO)OCN1C(=O)CCc2ccc(OCCCCN3CCN(c4cccc(Cl)c4Cl)CC3)cc21] |

TABLE A-continued
| No | Structure |
|---|---|
| 28 | 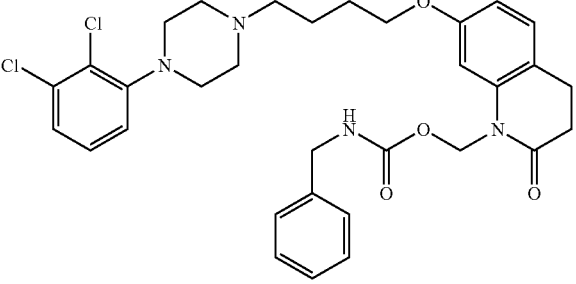 |
| 29 | 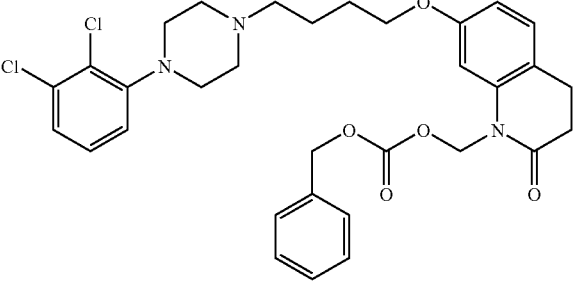 |
| 30 | 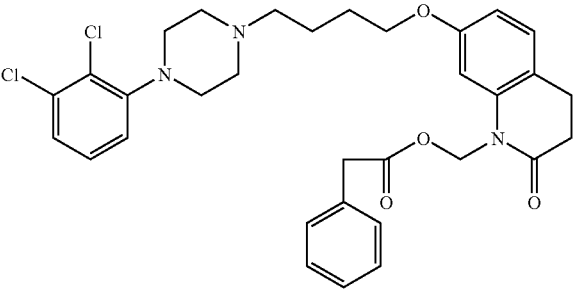 [SMILES: O=C(Cc1ccccc1)OCN1C(=O)CCc2ccc(OCCCCN3CCN(c4cccc(Cl)c4Cl)CC3)cc21] |
| 31 | 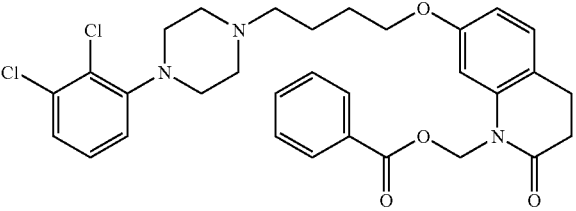 [SMILES: O=C(OCN1C(=O)CCc2ccc(OCCCCN3CCN(c4cccc(Cl)c4Cl)CC3)cc21)c1ccccc1] |
| 32 | 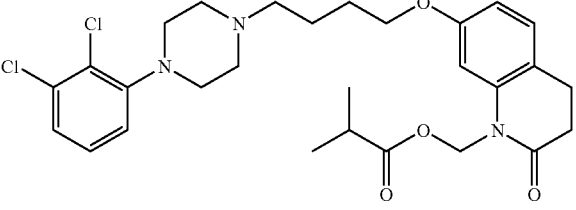 |
| 33 | 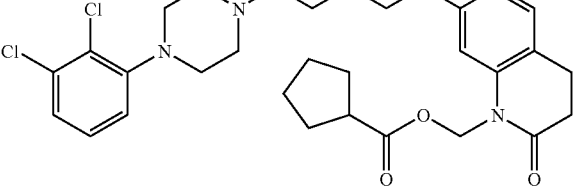 |

TABLE A-continued

| No | Structure |
|---|---|
| 34 | 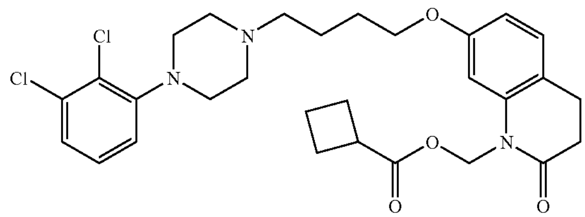 [SMILES: O=C(OCN1C(=O)CCc2ccc(OCCCCN3CCN(c4cccc(Cl)c4Cl)CC3)cc21)C1CCC1] |
| 35 | 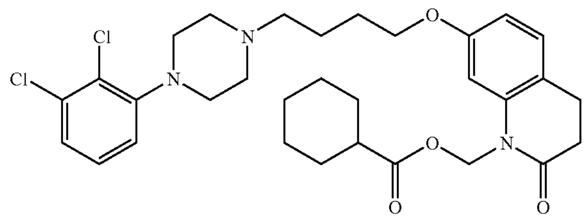 |
| 36 | 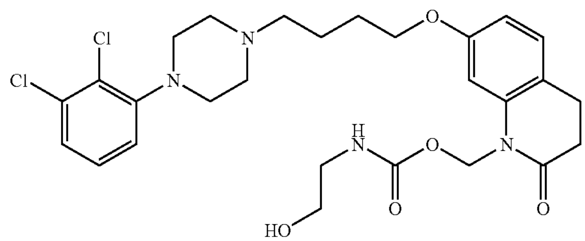 [SMILES: O=C(NCCO)OCN1C(=O)CCc2ccc(OCCCCN3CCN(c4cccc(Cl)c4Cl)CC3)cc21] |
| 37 | 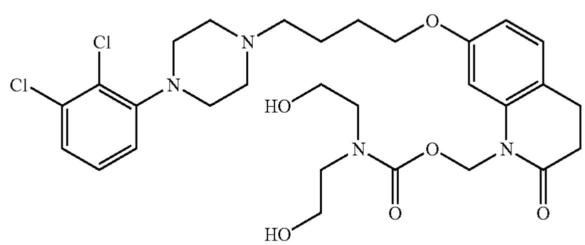 [SMILES: O=C(OCN1C(=O)CCc2ccc(OCCCCN3CCN(c4cccc(Cl)c4Cl)CC3)cc21)N(CCO)CCO] |
| 38 | 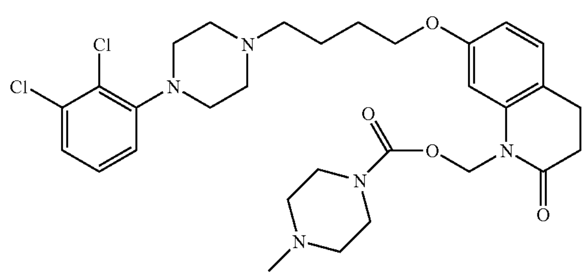 [SMILES: CN1CCN(C(=O)OCN2C(=O)CCc3ccc(OCCCCN4CCN(c5cccc(Cl)c5Cl)CC4)cc32)CC1] |
| 39 | 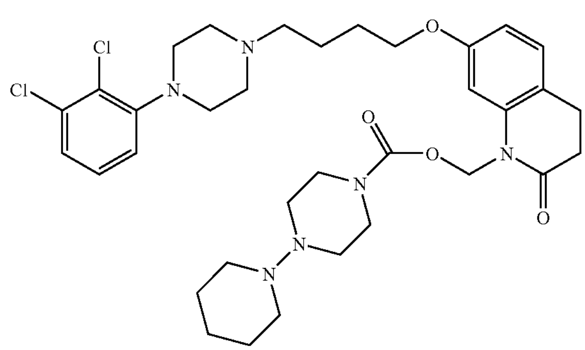 [SMILES: O=C(OCN1C(=O)CCc2ccc(OCCCCN3CCN(c4cccc(Cl)c4Cl)CC3)cc21)N1CCN(N2CCCCC2)CC1] |

TABLE A-continued
| No | Structure |
|---|---|
| 40 | 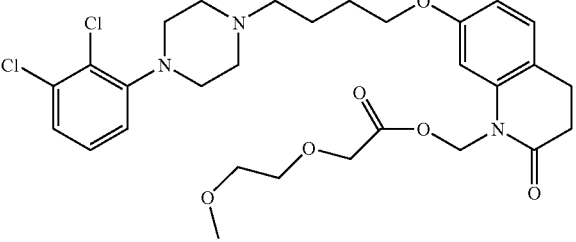 |
| 41 | 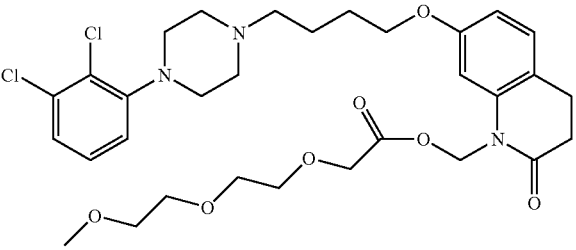 [SMILES: COCCOCCOCC(=O)OCN1C(=O)CCc2ccc(OCCCCN3CCN(c4cccc(Cl)c4Cl)CC3)cc21] |
| 42 | 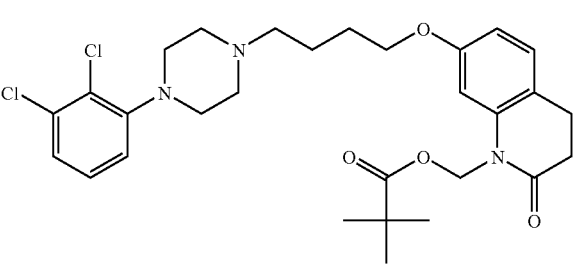 [SMILES: CC(C)(C)C(=O)OCN1C(=O)CCc2ccc(OCCCCN3CCN(c4cccc(Cl)c4Cl)CC3)cc21] |
| 43 | 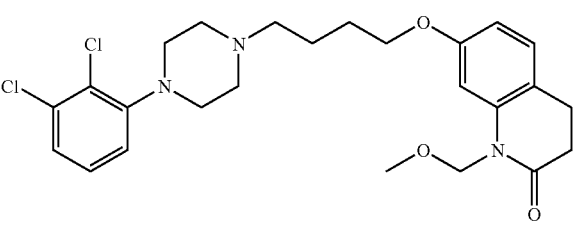 [SMILES: COCN1C(=O)CCc2ccc(OCCCCN3CCN(c4cccc(Cl)c4Cl)CC3)cc21] |
| 44 | 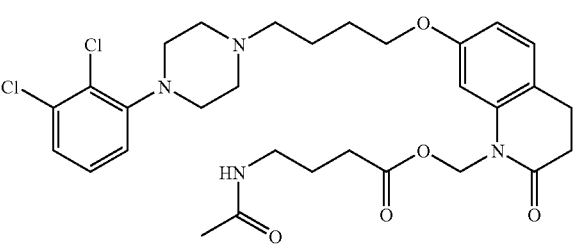 [SMILES: CC(=O)NCCCC(=O)OCN1C(=O)CCc2ccc(OCCCCN3CCN(c4cccc(Cl)c4Cl)CC3)cc21] |
| 45 | 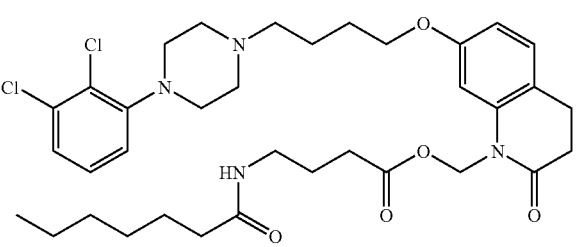 [SMILES: CCCCCCC(=O)NCCCC(=O)OCN1C(=O)CCc2ccc(OCCCCN3CCN(c4cccc(Cl)c4Cl)CC3)cc21] |

TABLE A-continued

| No | Structure |
|---|---|
| 46 | 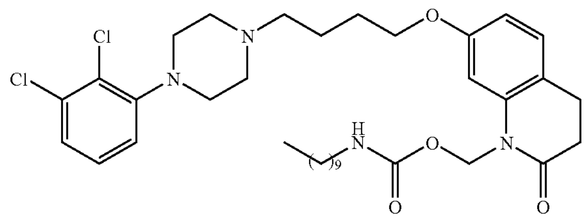 |
| 47 | 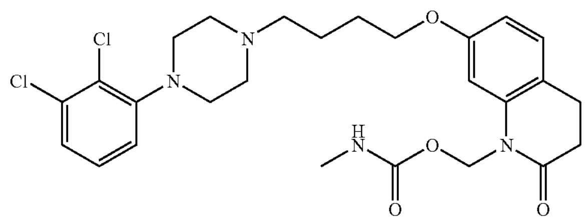 [SMILES: CNC(=O)OCN1C(=O)CCc2ccc(OCCCCN3CCN(c4cccc(Cl)c4Cl)CC3)cc21] |
| 48 | 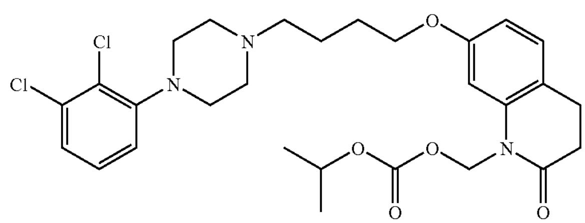 |
| 49 | 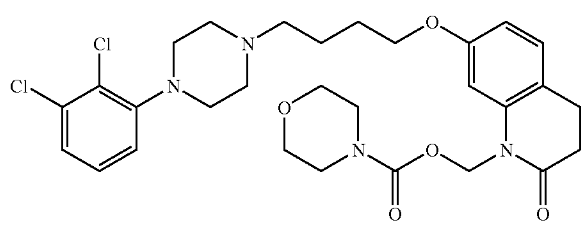 [SMILES: O=C(OCN1C(=O)CCc2ccc(OCCCCN3CCN(c4cccc(Cl)c4Cl)CC3)cc21)N1CCOCC1] |
| 50 | 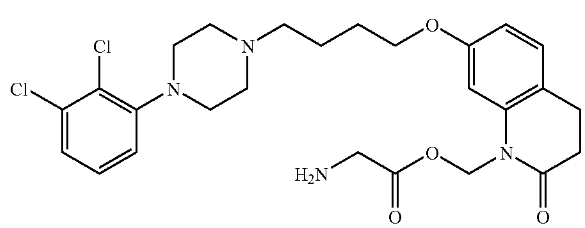 |
| 51 | 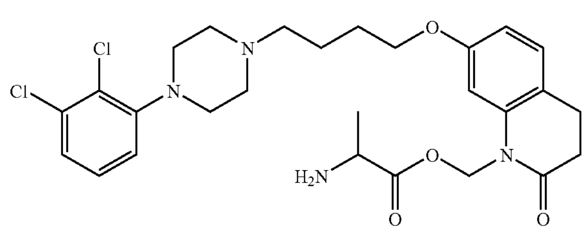 [SMILES: CC(N)C(=O)OCN1C(=O)CCc2ccc(OCCCCN3CCN(c4cccc(Cl)c4Cl)CC3)cc21] |

TABLE A-continued
| No | Structure |
|---|---|
| 52 | 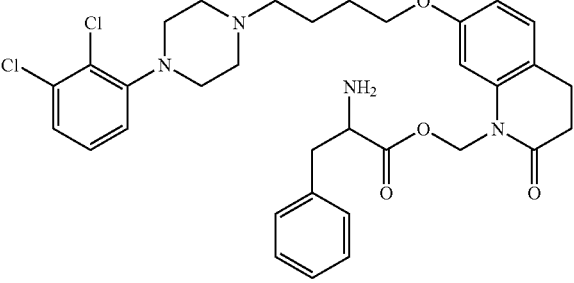 |
| 53 | 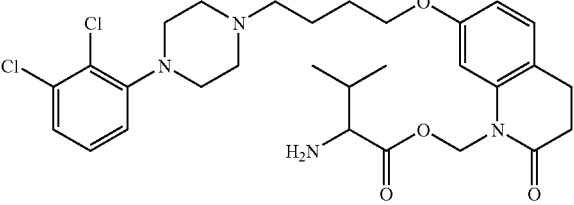 |
| 54 | 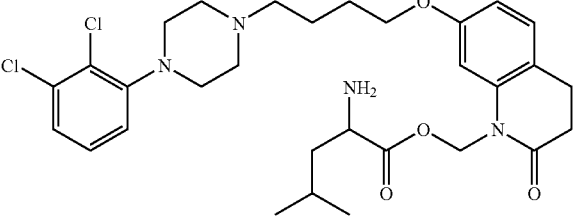 |
| 55 | 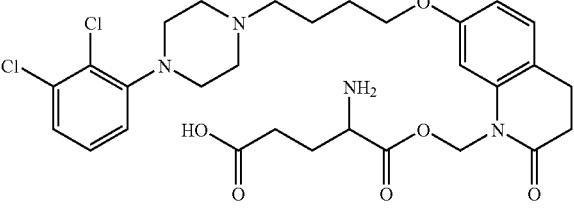 |
| 56 | 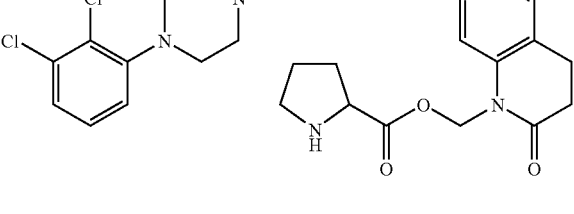 |
| 57 | 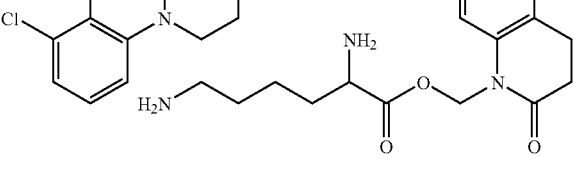 |

TABLE A-continued

| No | Structure |
|---|---|
| 58 | 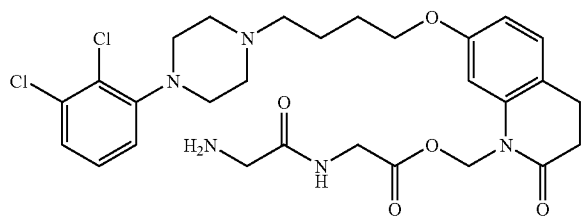 [SMILES: NCC(=O)NCC(=O)OCN1C(=O)CCc2ccc(OCCCCN3CCN(c4cccc(Cl)c4Cl)CC3)cc21] |
| 59 | 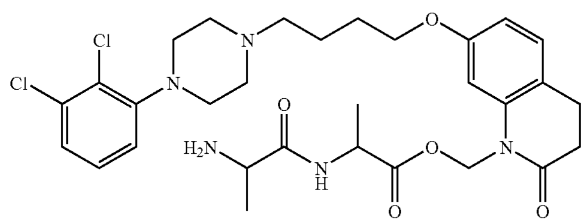 [SMILES: CC(N)C(=O)NC(C)C(=O)OCN1C(=O)CCc2ccc(OCCCCN3CCN(c4cccc(Cl)c4Cl)CC3)cc21] |
| 60 | 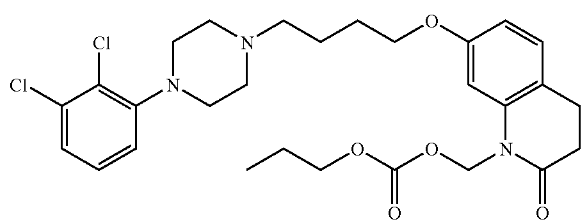 [SMILES: CCCOC(=O)OCN1C(=O)CCc2ccc(OCCCCN3CCN(c4cccc(Cl)c4Cl)CC3)cc21] |
| 61 | 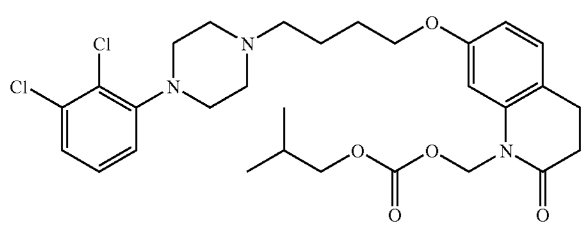 [SMILES: CC(C)COC(=O)OCN1C(=O)CCc2ccc(OCCCCN3CCN(c4cccc(Cl)c4Cl)CC3)cc21] |
| 62 | 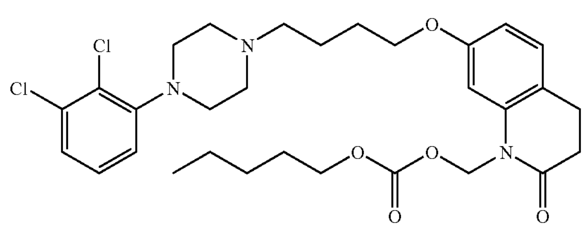 [SMILES: CCCCCOC(=O)OCN1C(=O)CCc2ccc(OCCCCN3CCN(c4cccc(Cl)c4Cl)CC3)cc21] |
| 63 | 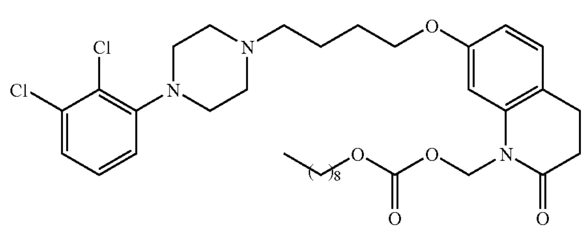 |
| 64 | 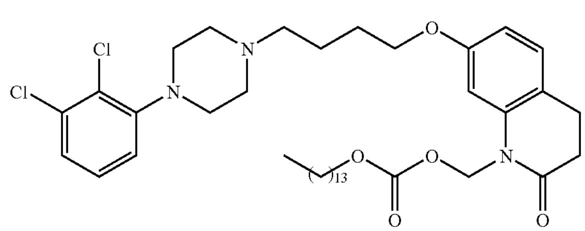 |

TABLE A-continued
| No | Structure |
|---|---|
| 65 | 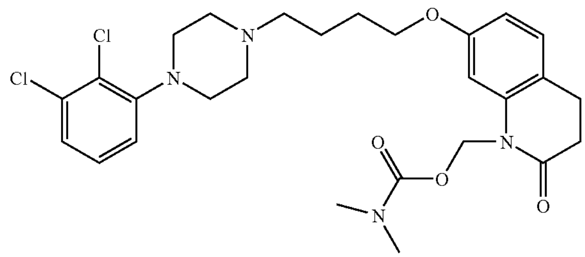 [SMILES: CN(C)C(=O)OCN1C(=O)CCc2ccc(OCCCCN3CCN(c4cccc(Cl)c4Cl)CC3)cc21] |
| 66 | 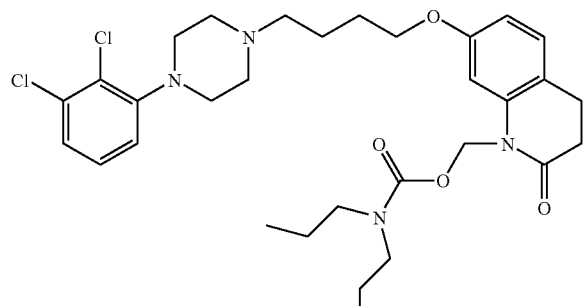 |
| 67 | 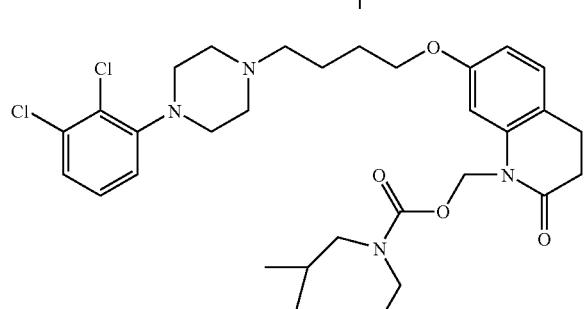 |
| 68 | 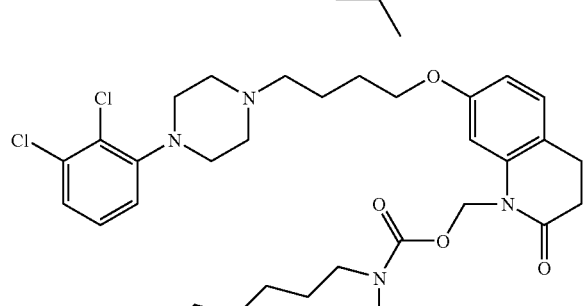 |
| 69 | 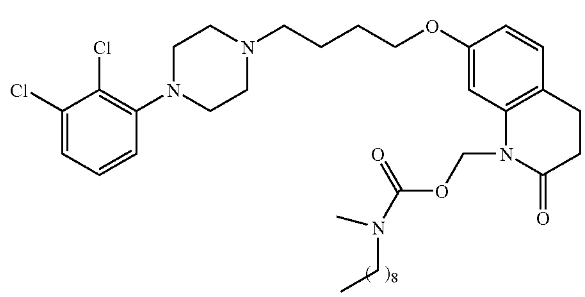 |

TABLE A-continued
| No | Structure |
|----|-----------|
| 70 | 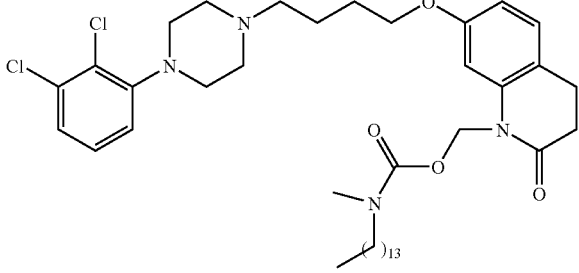 |
| 71 | 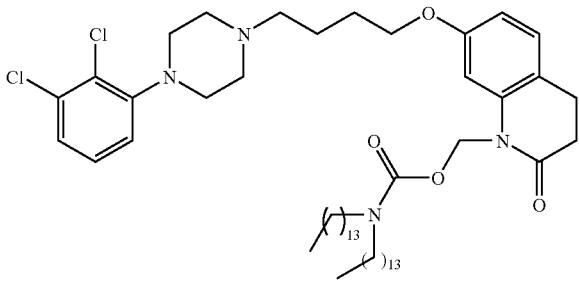 |
| 72 | 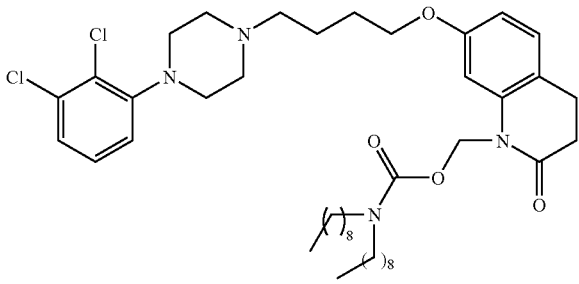 |
| 73 | 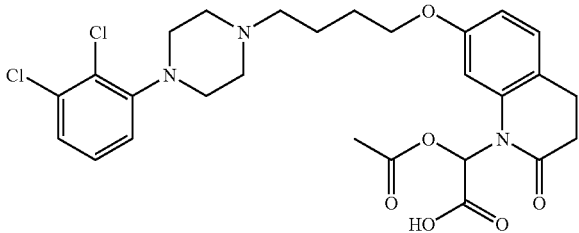 [SMILES: CC(=O)OC(C(=O)O)N1C(=O)CCc2ccc(OCCCCN3CCN(c4cccc(Cl)c4Cl)CC3)cc21] |
| 74 | 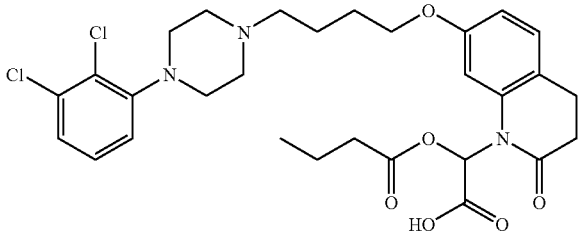 [SMILES: CCCC(=O)OC(C(=O)O)N1C(=O)CCc2ccc(OCCCCN3CCN(c4cccc(Cl)c4Cl)CC3)cc21] |
| 75 | 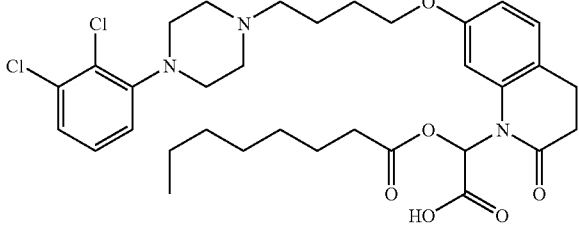 |

TABLE A-continued
| No | Structure |
|---|---|
| 76 | 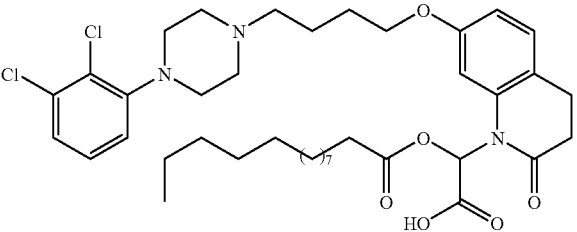 |
| 77 | 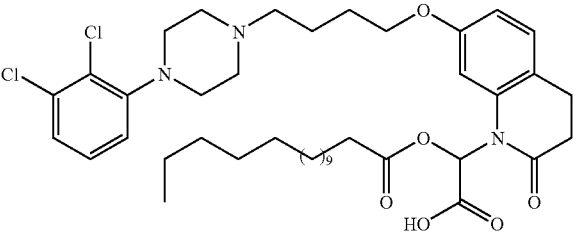 |
| 78 | 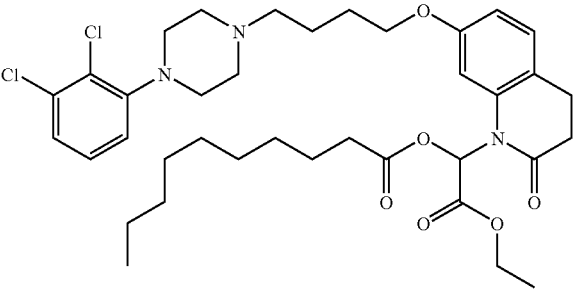 [SMILES: CCCCCCCCCC(=O)OC(C(=O)OCC)N1C(=O)CCc2ccc(OCCCCN3CCN(c4cccc(Cl)c4Cl)CC3)cc21] |
| 79 | 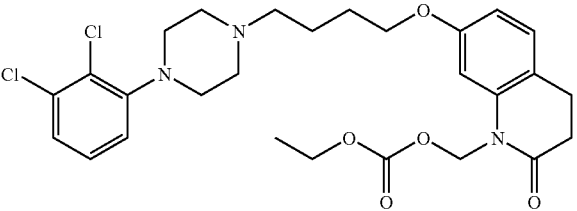 [SMILES: CCOC(=O)OCN1C(=O)CCc2ccc(OCCCCN3CCN(c4cccc(Cl)c4Cl)CC3)cc21] |
| 80 | 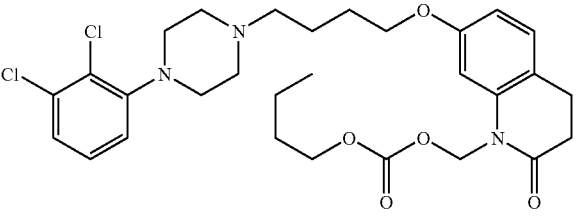 [SMILES: CCCCOC(=O)OCN1C(=O)CCc2ccc(OCCCCN3CCN(c4cccc(Cl)c4Cl)CC3)cc21] |
| 81 | 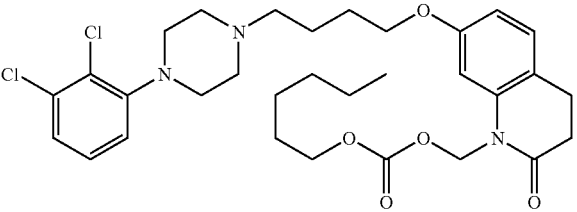 [SMILES: CCCCCCOC(=O)OCN1C(=O)CCc2ccc(OCCCCN3CCN(c4cccc(Cl)c4Cl)CC3)cc21] |

TABLE A-continued
| No | Structure |
|----|-----------|
| 82 | 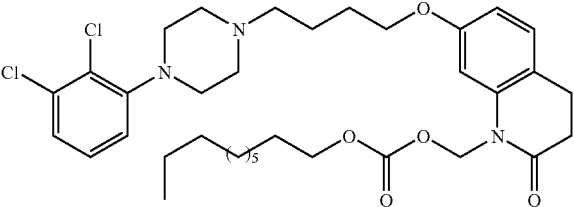 |
| 83 | 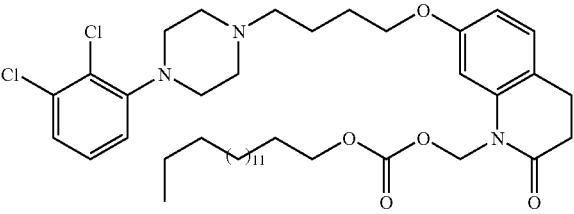 |
| 84 | 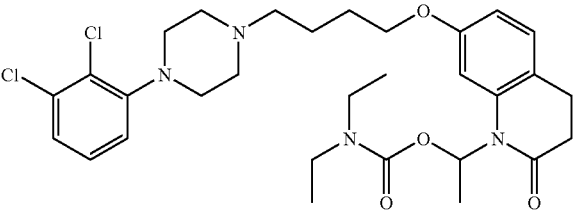 [SMILES: CCN(CC)C(=O)OC(C)N1C(=O)CCc2ccc(OCCCCN3CCN(c4cccc(Cl)c4Cl)CC3)cc21] |
| 85 | 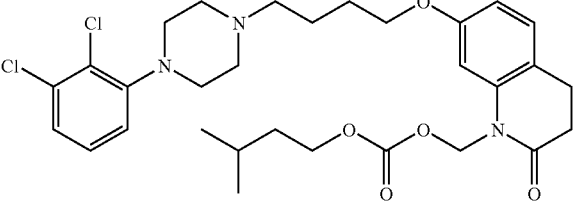 |
| 86 | 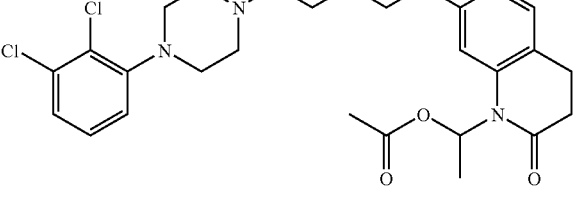 |
| 87 | 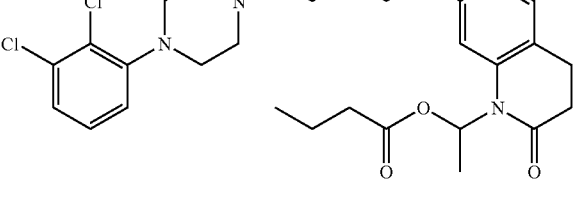 |
| 88 | 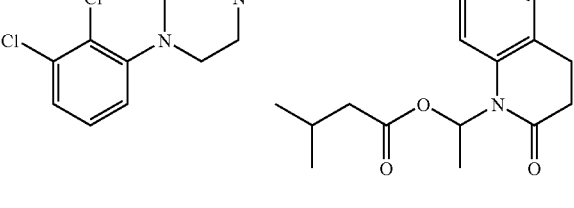 |

TABLE A-continued
| No | Structure |
|---|---|
| 89 | 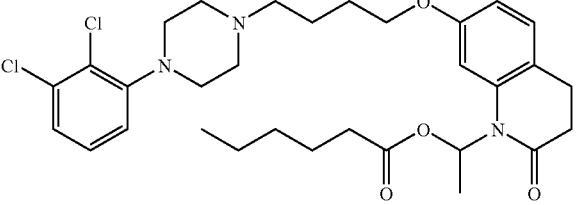 |
| 90 | 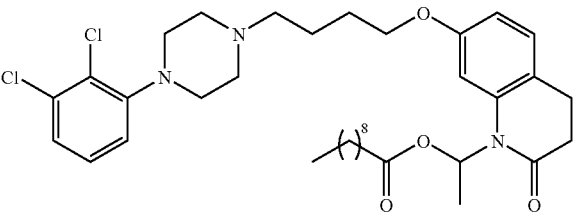 |
| 91 | 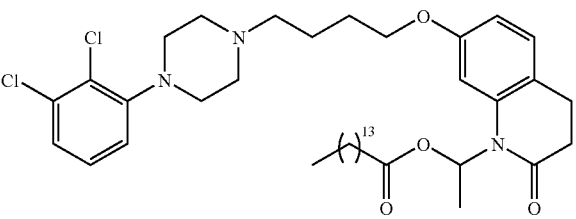 |
| 92 | 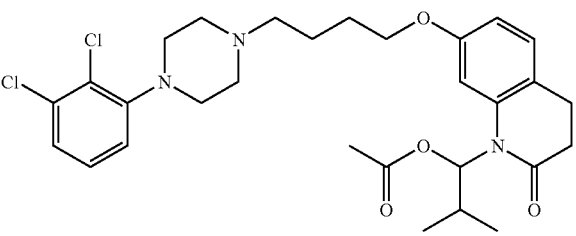 [SMILES: CC(=O)OC(C(C)C)N1C(=O)CCc2ccc(OCCCCN3CCN(c4cccc(Cl)c4Cl)CC3)cc21] |
| 93 | 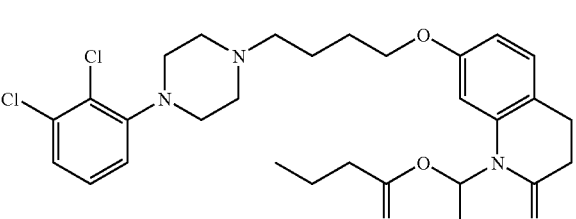 |
| 94 | 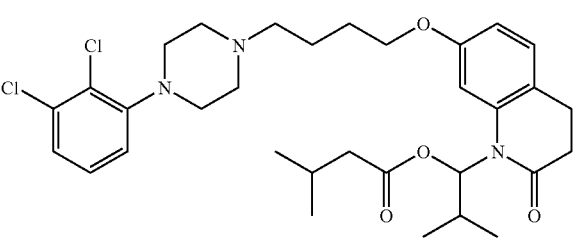 [SMILES: CCCC(=O)OC(C(C)C)N1C(=O)CCc2ccc(OCCCCN3CCN(c4cccc(Cl)c4Cl)CC3)cc21] |

TABLE A-continued
| No | Structure |
|----|-----------|
| 95 | 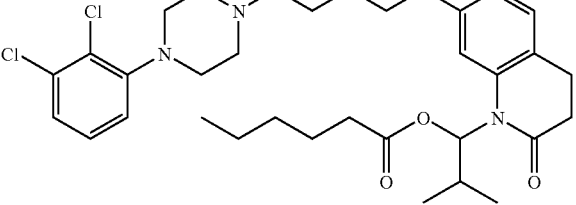 |
| 96 | 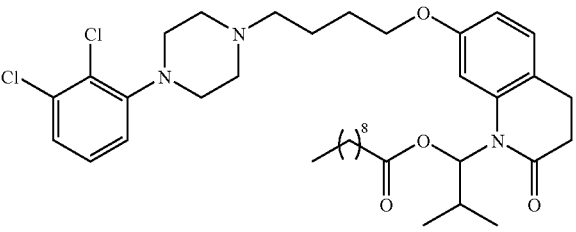 |
| 97 | 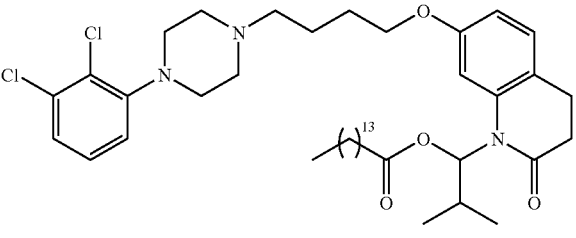 |
| 98 | 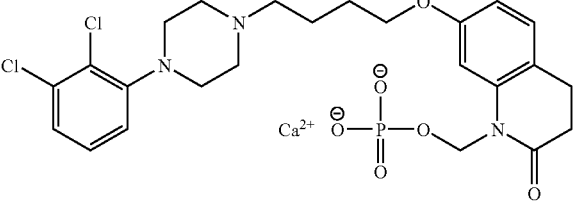 |
| 99 | 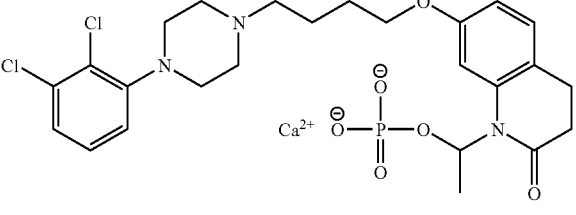 |
| 100 | 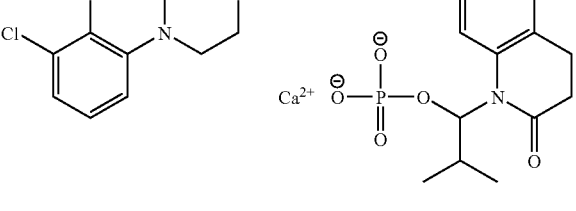 |

TABLE A-continued

| No | Structure |
|---|---|
| 101 | 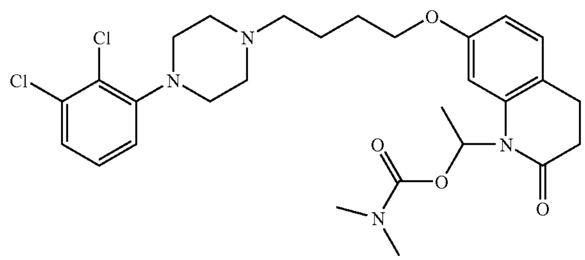 [SMILES: CC(OC(=O)N(C)C)N1C(=O)CCc2ccc(OCCCCN3CCN(c4cccc(Cl)c4Cl)CC3)cc21] |
| 102 | 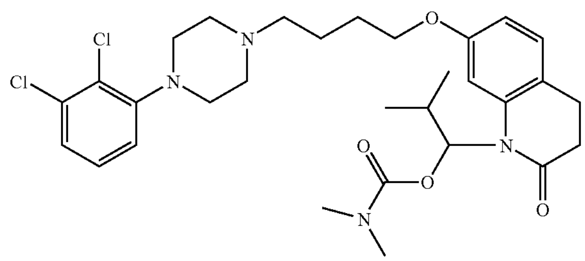 [SMILES: CC(C)C(OC(=O)N(C)C)N1C(=O)CCc2ccc(OCCCCN3CCN(c4cccc(Cl)c4Cl)CC3)cc21] |
| 103 | 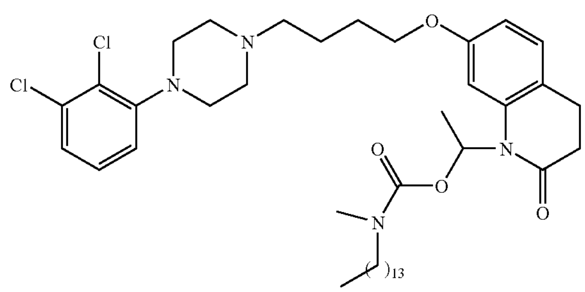 |
| 104 | 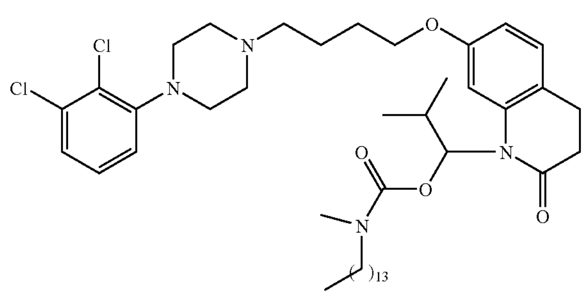 |
| 105 | 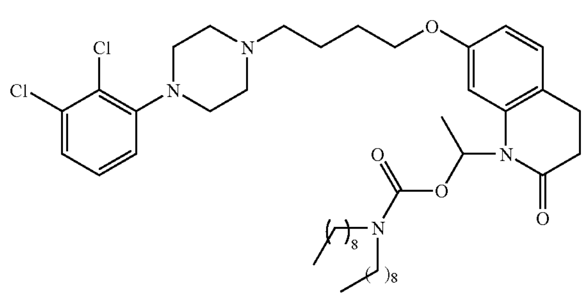 |

TABLE A-continued

| No | Structure |
|---|---|
| 106 | 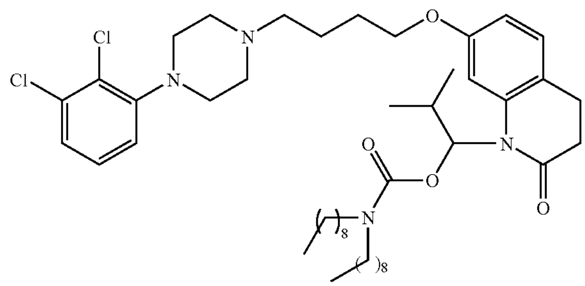 |
| 107 | 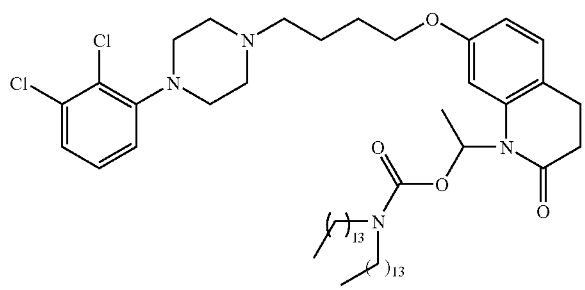 |
| 108 | 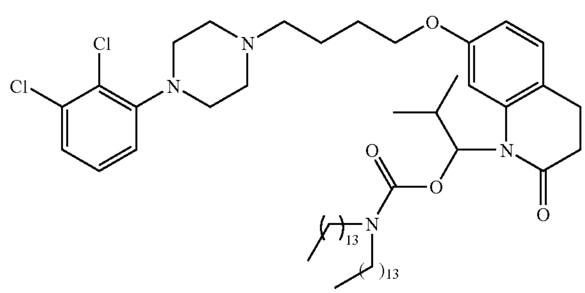 |
| 109 | 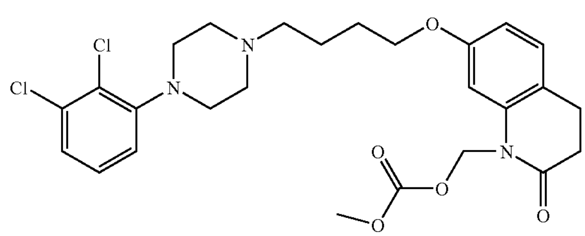 [SMILES: COC(=O)OCN1C(=O)CCc2ccc(OCCCCN3CCN(c4cccc(Cl)c4Cl)CC3)cc21] |
| 110 | 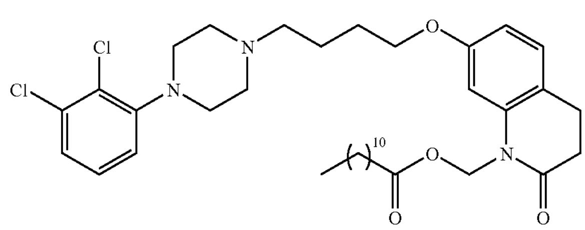 |

TABLE A-continued

| No | Structure |
|---|---|
| 111 | 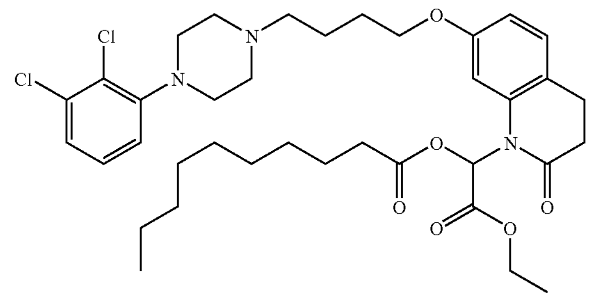 [SMILES: CCCCCCCCCC(=O)OC(C(=O)OCC)N1C(=O)CCc2ccc(OCCCCN3CCN(c4cccc(Cl)c4Cl)CC3)cc21] |
| 112 | 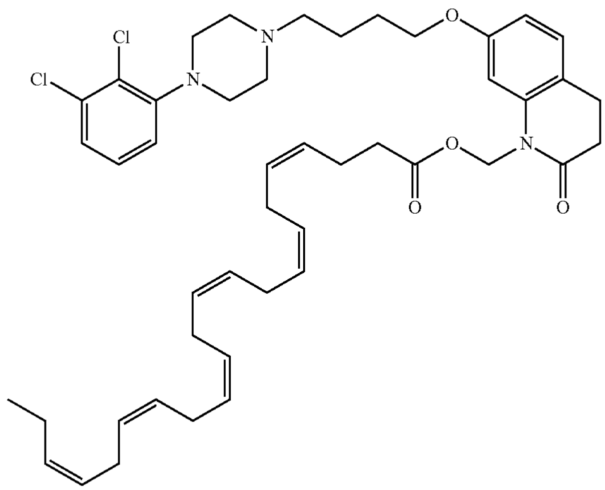 [SMILES: CC/C=C\C/C=C\C/C=C\C/C=C\C/C=C\C/C=C\CCC(=O)OCN1C(=O)CCc2ccc(OCCCCN3CCN(c4cccc(Cl)c4Cl)CC3)cc21] |
| 113 | 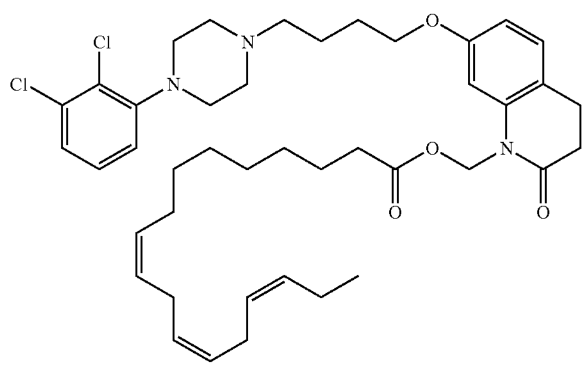 [SMILES: CC/C=C\C/C=C\C/C=C\CCCCCCCC(=O)OCN1C(=O)CCc2ccc(OCCCCN3CCN(c4cccc(Cl)c4Cl)CC3)cc21] |
| 114 | 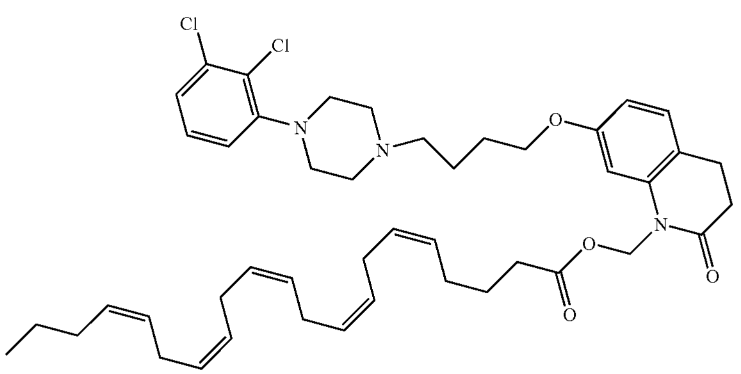 [SMILES: CCC/C=C\C/C=C\C/C=C\C/C=C\C/C=C\CCCC(=O)OCN1C(=O)CCc2ccc(OCCCCN3CCN(c4cccc(Cl)c4Cl)CC3)cc21] |

TABLE A-continued

| No | Structure |
|---|---|
| 115 | 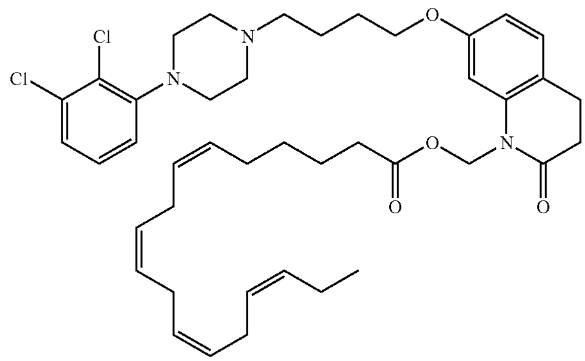 |
| 116 | 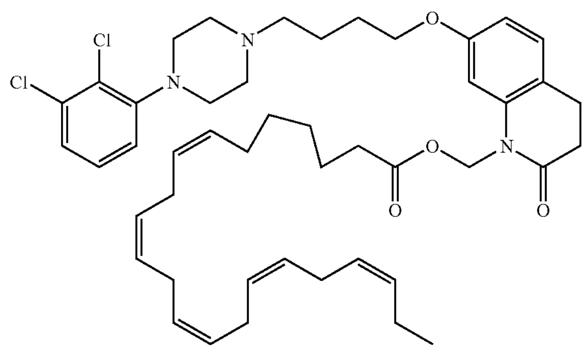 [SMILES: CC/C=C\C/C=C\C/C=C\C/C=C\C/C=C\CCCCCC(=O)OCN1C(=O)CCc2ccc(OCCCCN3CCN(c4cccc(Cl)c4Cl)CC3)cc21] |
| 117 | 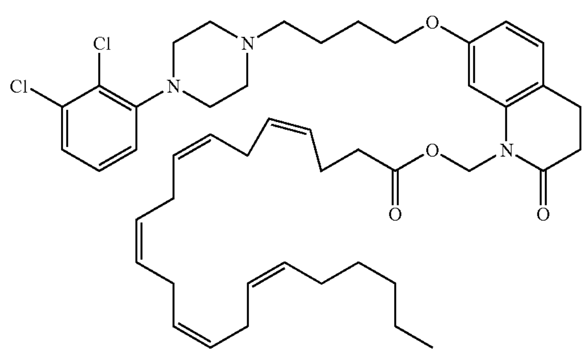 [SMILES: CCCCC/C=C\C/C=C\C/C=C\C/C=C\C/C=C\CCC(=O)OCN1C(=O)CCc2ccc(OCCCCN3CCN(c4cccc(Cl)c4Cl)CC3)cc21] |
| 118 | 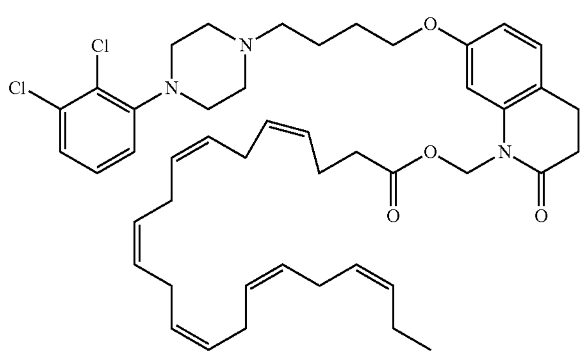 |

DEFINITIONS

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$") preferably about 7 to about 24 carbon atoms ("$C_7$-$C_{24}$"), preferably about 8 to about 24 carbon atoms ("$C_8$-$C_{24}$"), preferably about 9 to about 24 carbon atoms ("$C_9$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a tetravalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3, 4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug", and "prodrug" as used herein all include pharmaceutically acceptable salts, co-crystals, solvates, hydrates, polymorphs, enantiomers, diastereoisomers, racemates and the like of the compounds, drugs and prodrugs having the Formulas as set forth herein.

Substituents indicated as attached through variable points of attachments can be attached to any available position on the ring structure.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or methods of the invention may be made without departing from the spirit of the invention and the scope of the appended claims. General methodology for the preparation of lactam compounds can be found in the following publications: U.S. Pat. No. 7,160,888; U.S. Pat. No. 5,462,934; U.S. Pat. No. 4,914,094; U.S. Pat. No. 4,234,584; U.S. Pat. No. 4,514,401; U.S. Pat. No. 5,462,934; U.S. Pat. No. 4,468,402; WO 2006/090273 A2; WO 2008/150848 A1; WO 2006/112464 A1; WO 2008/132600 A1.

Example 1

Large scale synthesis of dehydroaripiprazole [7-(4-(4-(2,3-dichlorophenyl)piperazin-1-yl)butoxy)quinolin-2(1H)-one] (Compound 1; Formula VI)

Aripiprazole (Formula VIA; 15 g, 0.03 mol) was dissolved in anhydrous tetrahydrofuran (360 mL). Trifluoroacetic acid (12 mL, 0.16 mol) was added to the clear solution. 1,2-Dichloro-4,5-dicyano quinone (24.3 g, 0.11 mol) was added and the mixture was stirred at room temperature under nitrogen atmosphere. The reaction was stirred for 40 minutes and TLC showed no starting material remaining Water (1.5 L) was added then reaction mixture basified with 50% aq NaOH until pH 12. The reaction mixture was extracted with dichloromethane (3×1 L) and the combined organics were dried (MgSO$_4$) to give the crude product. This was purified by column chromatography on silica eluting with dichloromethane to 10% methanol/dichloromethane. The product was further purified by recrystallisation from 2-propanol to give the desired product (13.7 g, 92%) as an off white solid. $^1$H-NMR (400 MHz, CDCl$_3$) δ 12.33 (1H, br s), 7.72 (1H, d), 7.42 (1H, d), 7.16-7.11 (2H, m), 6.98-6.93 (1H, dd), 6.83-6.79 (2H, m), 6.53 (1H, d), 4.10 (2H, t), 3.09 (4H, br s), 2.67 (4H, br s), 2.52 (2H, t), 1.93-1.70 (4H, m). LCMS (acidic method) [M+H]$^+$ 446.02, rt 14.246 min.

Example 2

Synthesis of (7-(4-(4-(2,3-dichlorophenyl)piperazin-1-yl)butoxy)-2-oxoquinolin-1(2H)-yl)methyl butyrate (Compound 2)

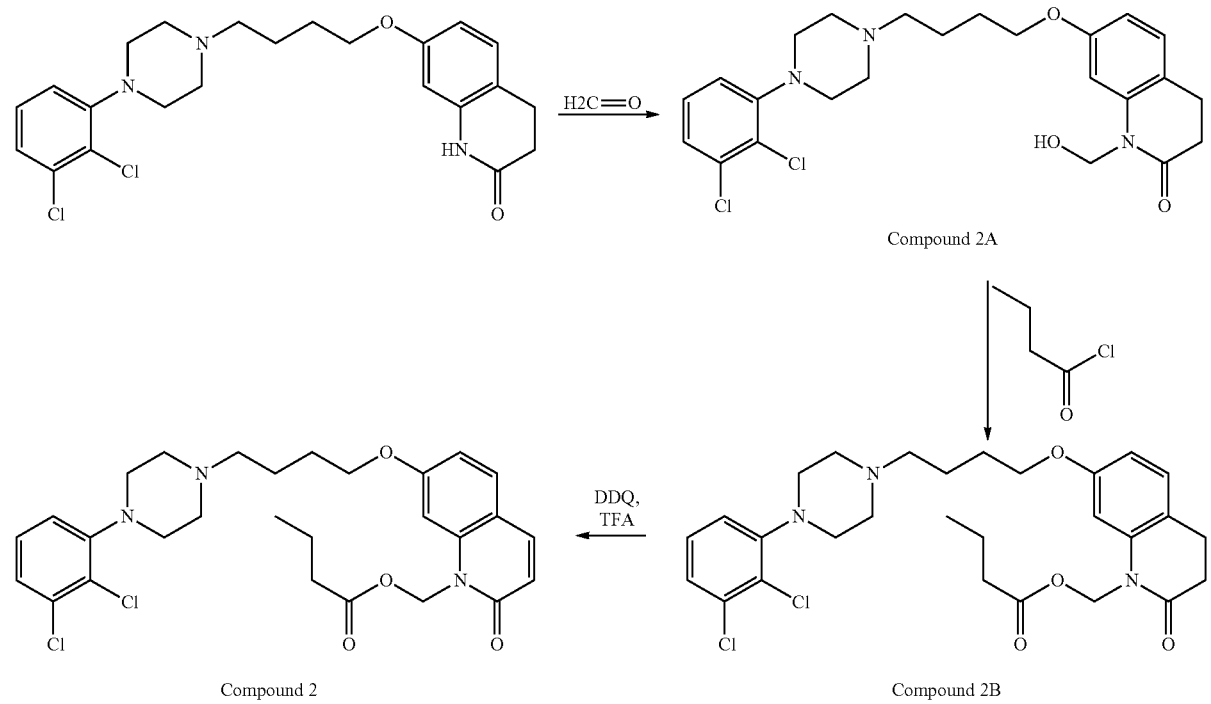

Step 1: Preparation of 7-(4-(4-(2,3-dichlorophenyl)piperazin-1-yl)butoxy)-1-(hydroxymethyl)-3,4-dihydroquinolin-2(1H)-one (Compound 2A)

A mixture of Aripiprazole (20 g, 45 mmol), triethylamine (1 mL, 7.1 mmol), formaldehyde (37% aqueous solution, 70 mL) and dimethylformamide (200 mL) was heated to 80° C. for 20 h. The reaction mixture was cooled, diluted with ethyl acetate (400 mL) and washed with water/brine (1:1, 3×500 mL). The organic phase was dried over MgSO$_4$, filtered and evaporated to dryness under vacuum to give hemi-aminal Compound 2A as a white solid (18.6 g, containing 25% Aripiprazole, 65% yield based on 2A).

Step 2: Synthesis of (7-(4-(4-(2,3-dichlorophenyl)piperazin-1-yl)butoxy)-2-oxo-3,4-dihydroquinolin-1(2H)-yl)methyl butyrate (Compound 2B)

To a stirred suspension of Compound 2A (3 g, 6.27 mmol) in dichloromethane (30 mL) was added pyridine (2.54 mL, 31.35 mmol) followed by butyryl chloride (0.98 mL, 9.41 mmol) over 1-2 mins. The resultant solution was stirred at room temperature for 1 h 30 mins. The reaction was quenched with methanol (2 mL) and the mixture diluted with 1:1 NaHCO$_3$ (aq)/brine (50 mL) and the layers separated. The aqueous layer was extracted with dichloromethane (10 mL) and the combined organics dried over MgSO$_4$. After filtration, the volatiles were removed and the residue azeotroped with toluene (3×10 mL). The crude material was purified by silica chromatography eluting 8% Methanol/(1:1 ethyl acetate/dichloromethane) to provide the desired product, Compound 2B (3.26 g, 5.94 mmol, 95% yield).

Step 3: Synthesis of Compound 2

To a stirred solution of Compound 2B (3.26 g, 5.94 mmol) in THF (100 mL) was added TFA (2.74 mL, 35.63 mmol) followed by DDQ (7.01 g, 30.88 mmol) in THF (40 mL). The reaction was stirred at room temperature over the weekend. The reaction was quenched with water (100 mL) and then poured into water (600 mL) and dichloromethane (100 mL). Solid NaHCO$_3$ (100 g) was added and the mixture stirred for approximately 30 minutes. Dichloromethane (200 mL) was added and the mixture filtered. The collected filtrate was transferred to a separating funnel and the layers separated. The aqueous layer was extracted with dichloromethane (2×100 mL) and the combined organics washed with water (3×100 mL, brine (100 mL) and dried over MgSO$_4$. After filtration, the volatiles were removed. The crude material was purified by silica chromatography eluting 0-4% Methanol/(1:1 ethyl acetate/dichloromethane). The oil was recrystallized from methanol to give Compound 2, (2.03 g, 3.72 mmol, 63% yield). $^1$H-NMR (300 MHz, CDCl$_3$) δ 7.63 (1H, d), 7.45 (1H, d), 7.19-7.06 (2H, m), 6.99-6.90 (1H, m), 6.88-6.78 (2H, m), 6.52 (1H, d), 6.33 (2H, s), 4.06 (2H, t), 3.17-2.99 (4H, bs), 2.74-2.43 (6H, m), 2.35 (2H, t), 1.94-1.54 (6H, m), 0.93 (3H, t).

The following compounds were prepared in an analogous fashion to Compound 2:

(7-(4-(4-(2,3-dichlorophenyl)piperazin-1-yl)butoxy)-2-oxoquinolin-1(2H)-yl)methyl palmitate (Compound 3). $^1$H-NMR (400 MHz, CDCl$_3$) δ 7.62 (1H, d), 7.44 (1H, d), 7.18-7.10 (2H, m), 6.98-6.91 (1H, m), 6.87-6.80 (2H, m), 6.52 (1H, d), 6.32 (2H, s), 4.05 (2H, t), 3.15-2.99 (4H, bs), 2.74-2.44 (6H, m), 2.35 (2H, t), 1.92-1.83 (2H, m), 1.80-1.68 (2H, m) 1.66-1.55 (2H, m), 1.32-1.14 (24H, m), 0.87 (3H, t).

(7-(4-(4-(2,3-dichlorophenyl)piperazin-1-yl)butoxy)-2-oxoquinolin-1(2H)-yl)methyl laurate (Compound 4) $^1$H-NMR (400 MHz, CDCl$_3$) δ 7.62 (1H, d), 7.43 (1H, d), 7.17-7.10 (2H, m), 6.96-6.92 (1H, m), 6.87-6.80 (2H, m), 6.51 (1H, d), 6.33 (2H, s), 4.06 (2H, t), 3.12-3.01 (4H, bs), 2.71-2.59 (4H, bs), 2.50 (2H, t), 2.35 (2H, t), 1.92-1.83 (2H, m), 1.78-1.69 (2H, m) 1.66-1.55 (2H, m), 1.32-1.16 (16H, m), 0.86 (3H, t).

(7-(4-(4-(2,3-dichlorophenyl)piperazin-1-yl)butoxy)-2-oxoquinolin-1(2H)-yl)methyl stearate (Compound 5) $^1$H-NMR (400 MHz, CDCl$_3$) δ 7.62 (1H, d), 7.44 (1H, d), 7.17-7.11 (2H, m), 6.97-6.92 (1H, m), 6.87-6.79 (2H, m), 6.51 (1H, d), 6.32 (2H, s), 4.05 (2H, t), 3.13-3.00 (4H, bs), 2.73-2.58 (4H, bs), 2.50 (2H, t), 2.35 (2H, t), 1.92-1.83 (2H, m), 1.79-1.69 (2H, m) 1.66-1.55 (2H, m), 1.32-1.14 (28H, m), 0.87 (3H, t).

(7-(4-(4-(2,3-dichlorophenyl)piperazin-1-yl)butoxy)-2-oxoquinolin-1(2H)-yl)methyl acetate (Compound 6) $^1$H-NMR (300 MHz, CDCl$_3$) δ 7.63 (1H, d), 7.45 (1H, d), 7.18-7.11 (2H, m), 6.98-6.92 (1H, m), 6.90-6.80 (2H, m), 6.52 (1H, d), 6.32 (2H, s), 4.07 (2H, t), 3.14-3.01 (4H, bs), 2.73-2.59 (4H, bs), 2.51 (2H, t), 2.12 (3H, s), 1.95-1.82 (2H, m), 1.82-1.68 (2H, m).

(7-(4-(4-(2,3-dichlorophenyl)piperazin-1-yl)butoxy)-2-oxoquinolin-1(2H)-yl)methyl 2,2-dimethylbutanoate (Compound 7) $^1$H-NMR (400 MHz, CDCl$_3$) δ 7.61 (1H, d), 7.43 (1H, d), 7.17-7.10 (2H, m), 6.97-6.92 (1H, m), 6.83-6.79 (2H, m), 6.51 (1H, d), 6.31 (2H, s), 4.05 (2H, t), 3.12-3.02 (4H, bs), 2.71-2.60 (4H, bs), 2.50 (2H, t), 1.92-1.83 (2H, m), 1.78-1.68 (2H, m) 1.55 (2H, q), 1.15 (6H, s), 0.81 (3H, t).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed:
1. A method for preparing a compound of Formula I, comprising the step of reacting a compound of Formula IA:

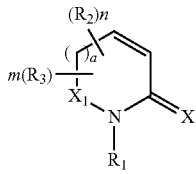

Formula I

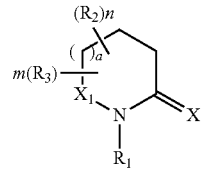

Formula IA with a compound of Formula II:

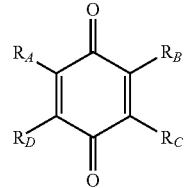

Formula II wherein X is —S— or —O—;

Each n, m and a is independently selected from 0, 1, 2 or 3;

$X_1$ is selected from absent, —S—, —O—, —S(O)—, —S(O)$_2$—, —N(R$_{10}$)—, —C(O)—, —C(OR$_{10}$)(R$_{11}$)—, —[C(R$_{10}$)(R$_{11}$)]$_v$—, —C(R$_{10}$)(R$_{11}$)=C(R$_{10}$)(R$_{11}$)—; wherein v is 0, 1, 2, 3, 4, 5; wherein each R$_{10}$ and R$_{11}$ is independently absent, hydrogen, halogen, aliphatic, substituted aliphatic, aryl or substituted aryl; alternatively two R$_{10}$ and R$_{11}$ together with the atoms to which they are attached may form an additional optionally substituted, 3, 4, 5, 6 or 7 membered ring;

Each R$_1$, R$_2$ and R$_3$ is independently absent, hydrogen, halogen, aliphatic, substituted aliphatic, aryl or substituted aryl; alternatively two or more R$_1$, R$_2$ and R$_3$ together with the atoms to which they are attached may form one or two additional optionally substituted, 3, 4, 5, 6 or 7 membered ring;

Each R$_A$, R$_B$, R$_C$, and R$_D$ is independently selected from hydrogen, halogen, —CN, NH$_2$, NR$_{100}$R$_{101}$, SR$_{100}$, OR$_{100}$, aliphatic, substituted aliphatic, aryl and substituted aryl;

wherein R$_{100}$ and R$_{101}$, are independently selected from hydrogen, halogen, aliphatic, substituted aliphatic, aryl or substituted aryl;

in the presence of an acid;

wherein said compound of Formula IA contains a primary, secondary or tertiary amine having a pKa of about 6 to about 45.

2. The method according to claim 1, wherein R$_1$ is selected from H, —C(R$_J$)(R$_K$)—OR$_{20}$, —C(R$_J$)(R$_K$)—OC(O)OR$_{20}$, —C(R$_J$)(R$_K$)—OC(O)R$_{20}$, —C(R$_J$)(R$_K$)—OC(O)NR$_{20}$R$_{21}$, —(C(R$_J$)(R$_K$))—OPO$_3$MY, —(C(R$_J$)(R$_K$))—OP(O)(OR$_{20}$)(OR$_{21}$), —[C(R$_J$)(R$_K$)O]$_z$—R$_{20}$, —[C(R$_J$)(R$_K$)O]$_z$—C(O)OR$_2$O, —[C(R$_J$)(R$_K$)O]$_z$—C(O)R$_{20}$, —[C(R$_J$)(R$_K$)O]$_z$—C(O)NR$_{20}$R$_{21}$, —[C(R$_J$)(R$_K$)O]$_z$—OPO$_3$MY, —[C(R$_J$)(R$_K$)O]$_z$—P(O)$_2$(OR$_{20}$)M and —[C(R$_J$)(R$_K$)O]$_z$—P(O)(OR$_{20}$)(OR$_{21}$);

wherein each R$_J$ and R$_K$ is independently selected from hydrogen, halogen, aliphatic, substituted aliphatic, aryl or substituted aryl;

each R$_{20}$ and R$_{21}$ is independently selected from hydrogen, aliphatic, substituted aliphatic, aryl or substituted aryl;

Y and M are the same or different and each is a monovalent cation; or M and Y together is a divalent cation; and z is 0, 1, 2, 3, 4, 5, 6, 7, 8, 9 or 10.

3. A method according to claim 2, wherein R$_1$ is selected from Tables 1-4:

TABLE 1

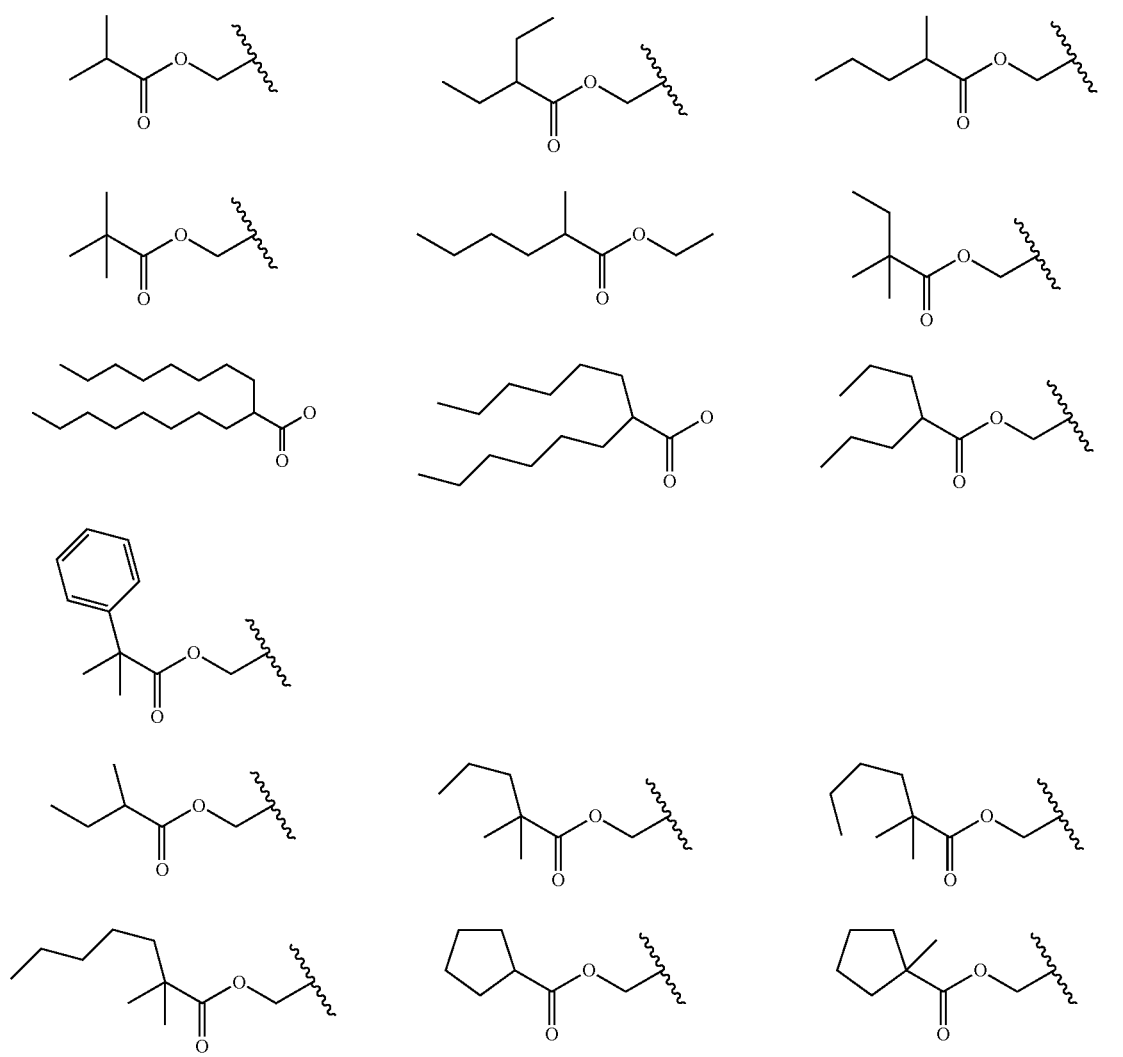

TABLE 1-continued
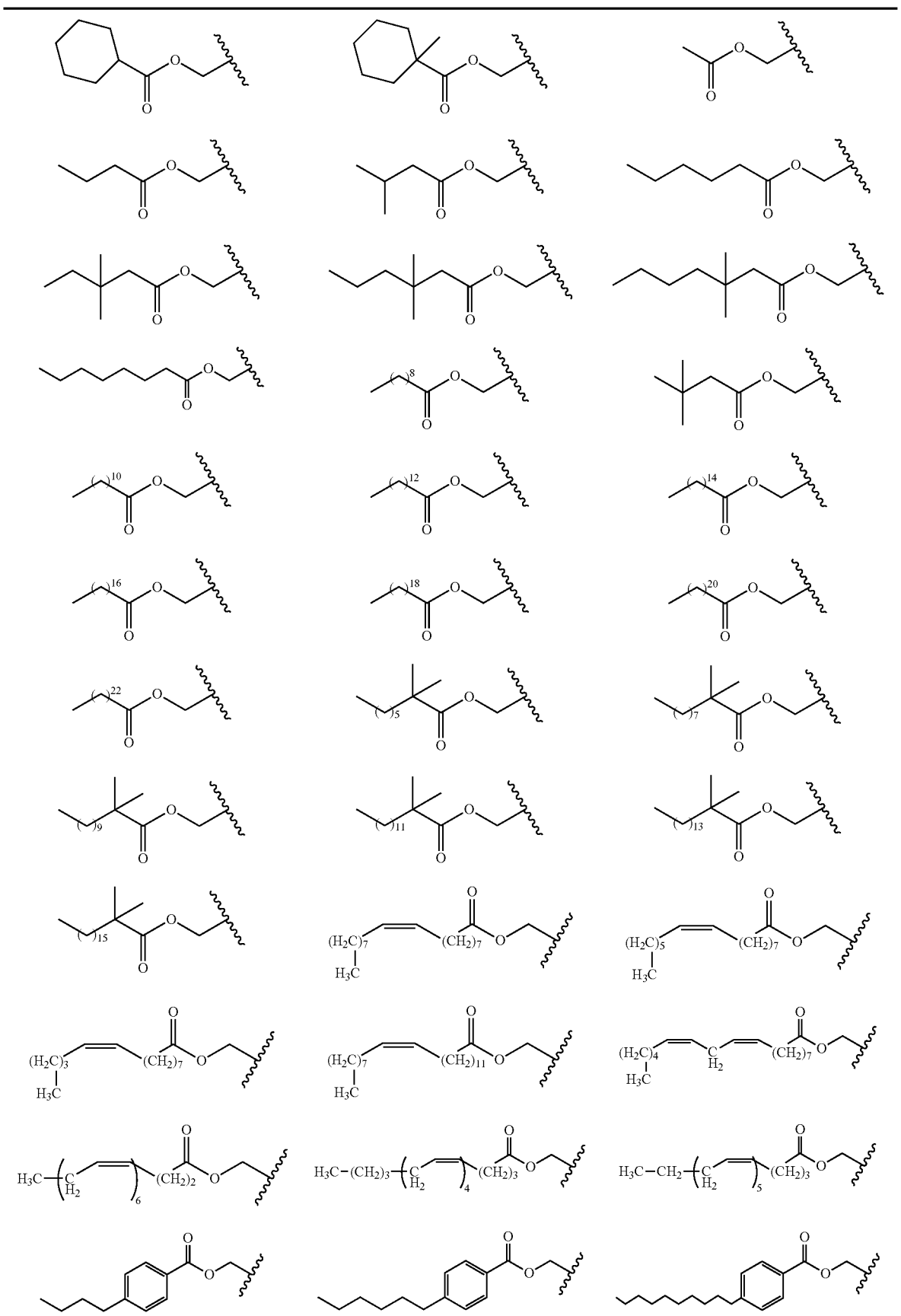

TABLE 1-continued
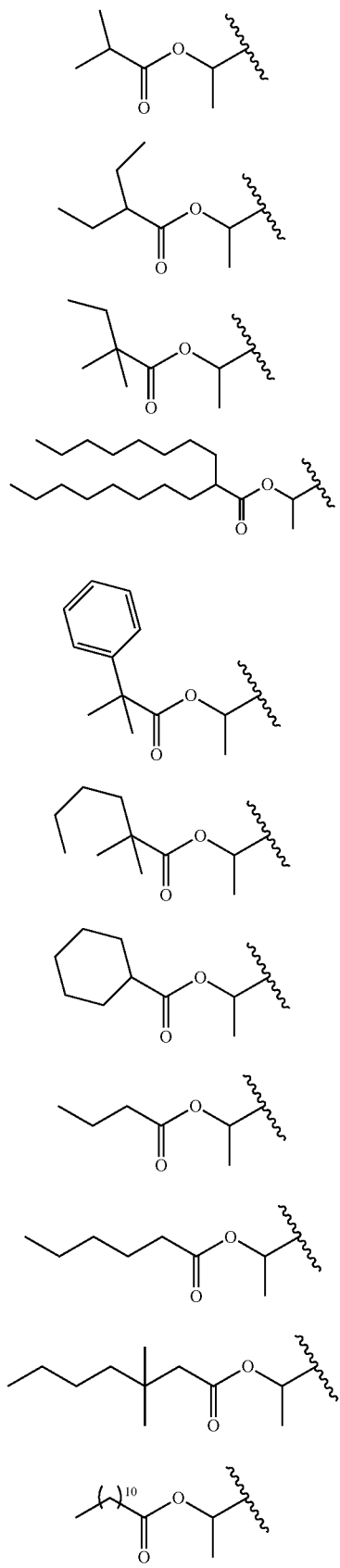

TABLE 1-continued
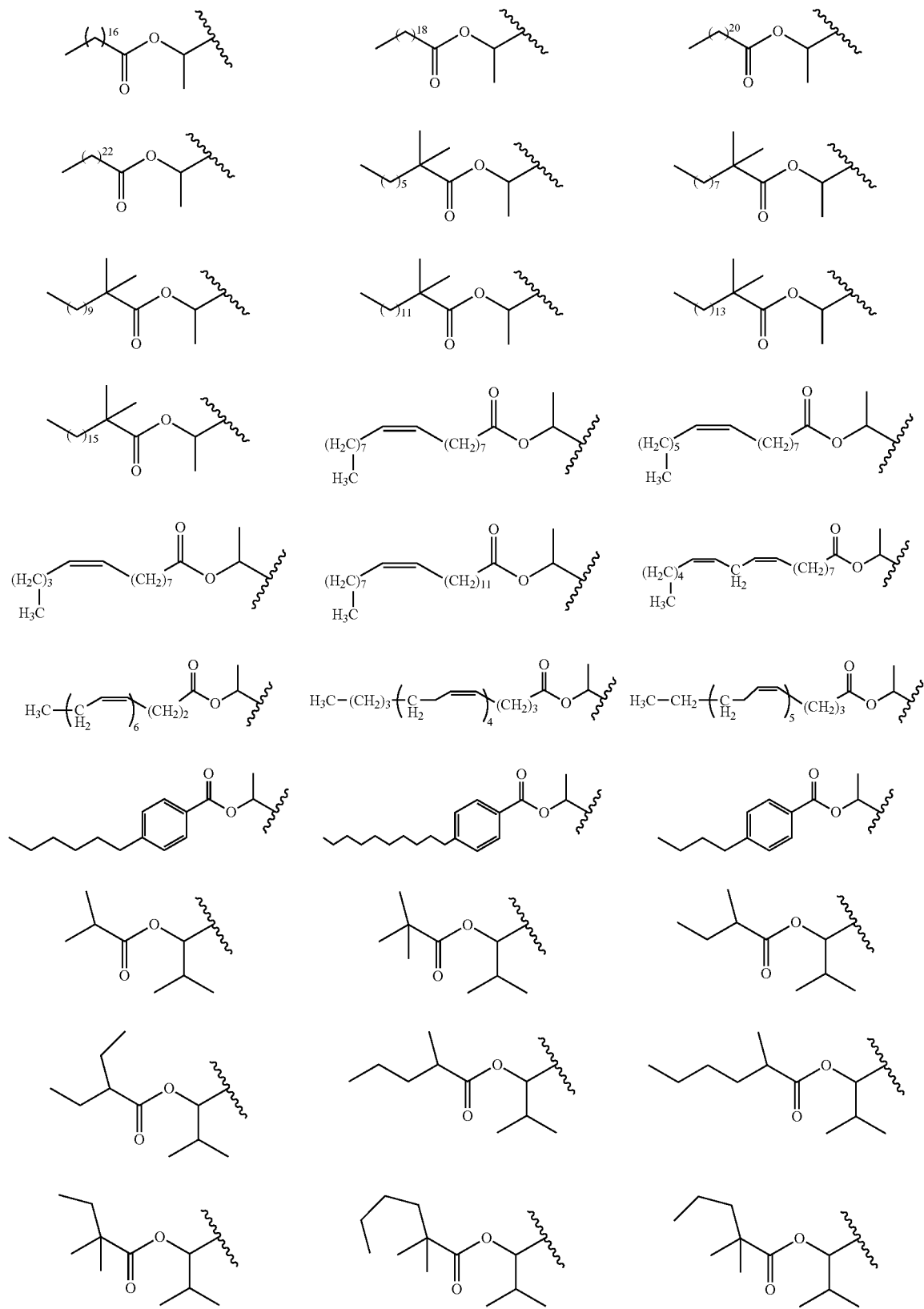

TABLE 1-continued
| 125 | | 126 |
|---|---|---|
| 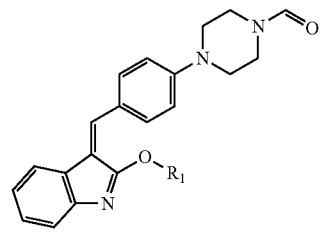 | 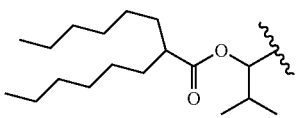 [SMILES: *C(OC(=O)C(CCCCCC)CCCCCC)C(C)C] | 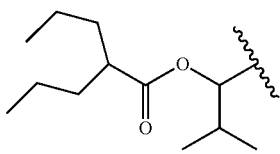 [SMILES: *C(OC(=O)C(CCC)CCC)C(C)C] |
| 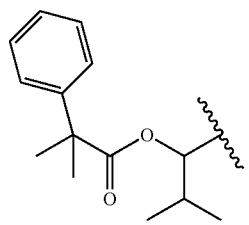 [SMILES: *C(OC(=O)C(C)(C)c1ccccc1)C(C)C] | 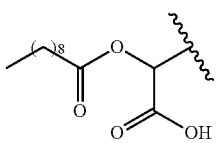 | 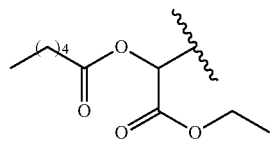 |
| 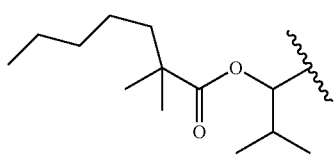 [SMILES: *C(OC(=O)C(C)(C)CCCCC)C(C)C] | 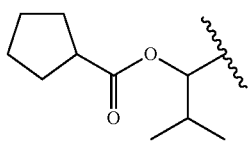 [SMILES: *C(OC(=O)C1CCCC1)C(C)C] | 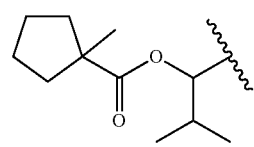 [SMILES: *C(OC(=O)C1(C)CCCC1)C(C)C] |
| 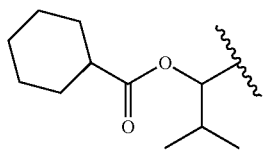 [SMILES: *C(OC(=O)C1CCCCC1)C(C)C] | 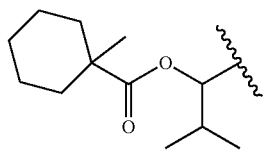 [SMILES: *C(OC(=O)C1(C)CCCCC1)C(C)C] | 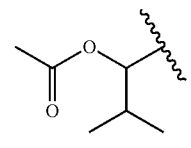 [SMILES: *C(OC(C)=O)C(C)C] |
| 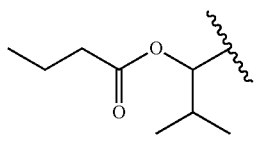 [SMILES: *C(OC(=O)CCC)C(C)C] | 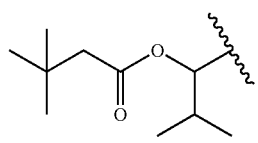 [SMILES: *C(OC(=O)CC(C)(C)C)C(C)C] | 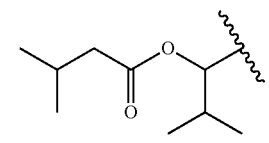 [SMILES: *C(OC(=O)CC(C)C)C(C)C] |
| 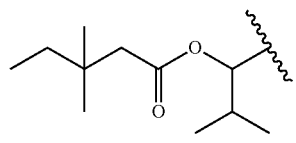 [SMILES: *C(OC(=O)CC(C)(C)CC)C(C)C] | 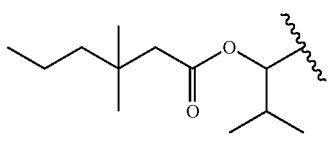 [SMILES: *C(OC(=O)CC(C)(C)CCC)C(C)C] | 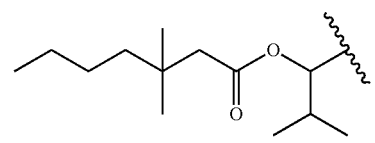 [SMILES: *C(OC(=O)CC(C)(C)CCCC)C(C)C] |
| 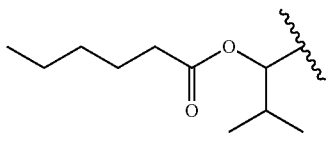 [SMILES: *C(OC(=O)CCCCC)C(C)C] | 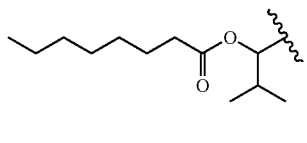 [SMILES: *C(OC(=O)CCCCCCC)C(C)C] | 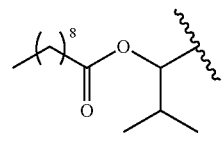 |
| 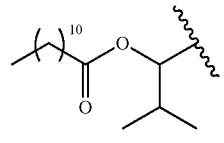 | 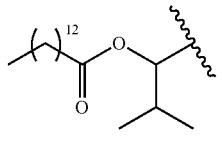 | 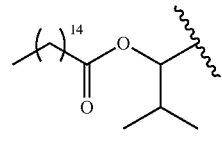 |
| 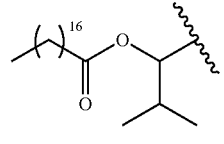 | 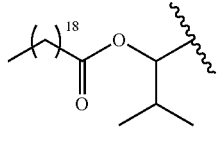 | 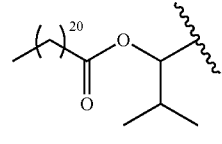 |

TABLE 1-continued
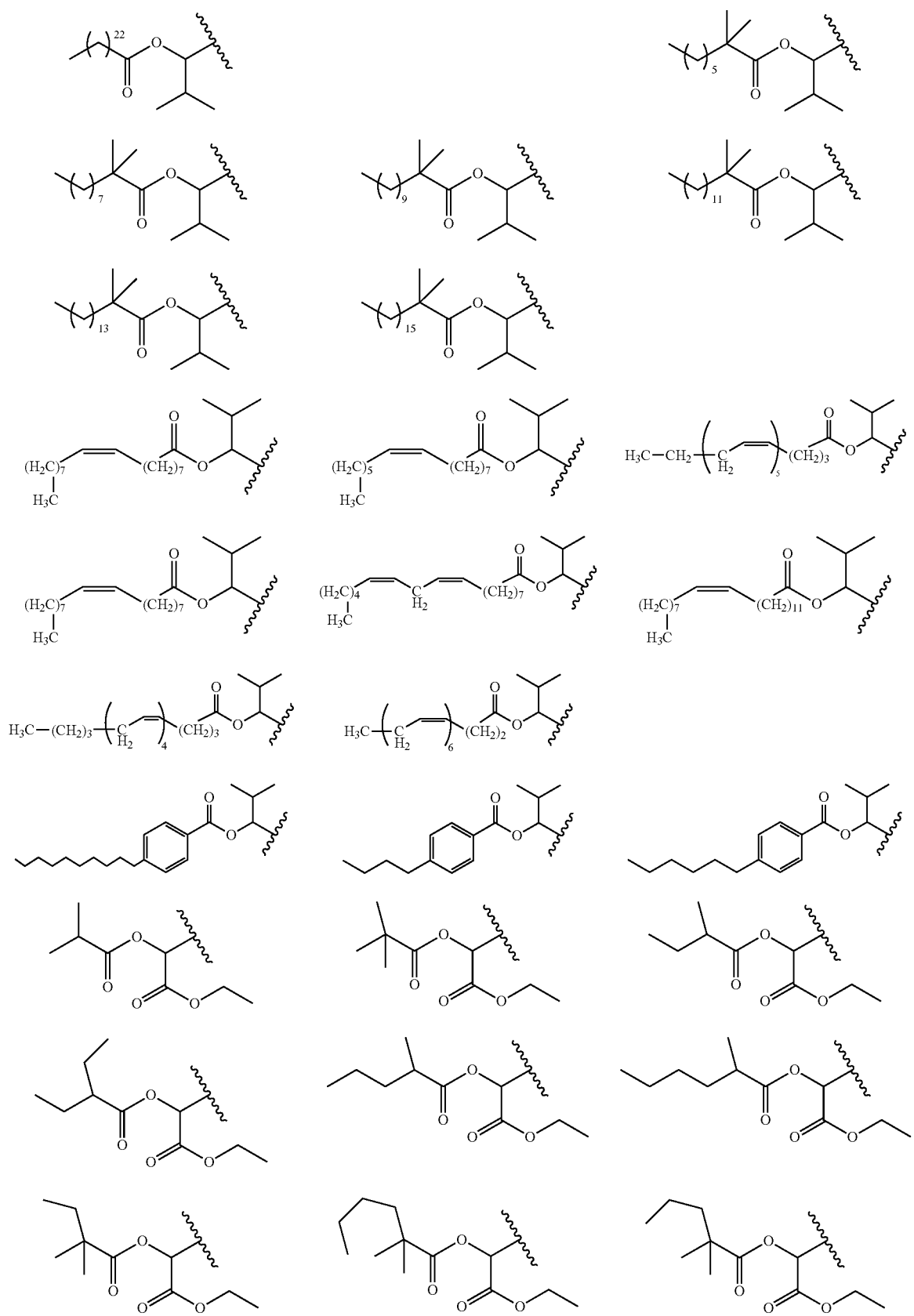

TABLE 1-continued
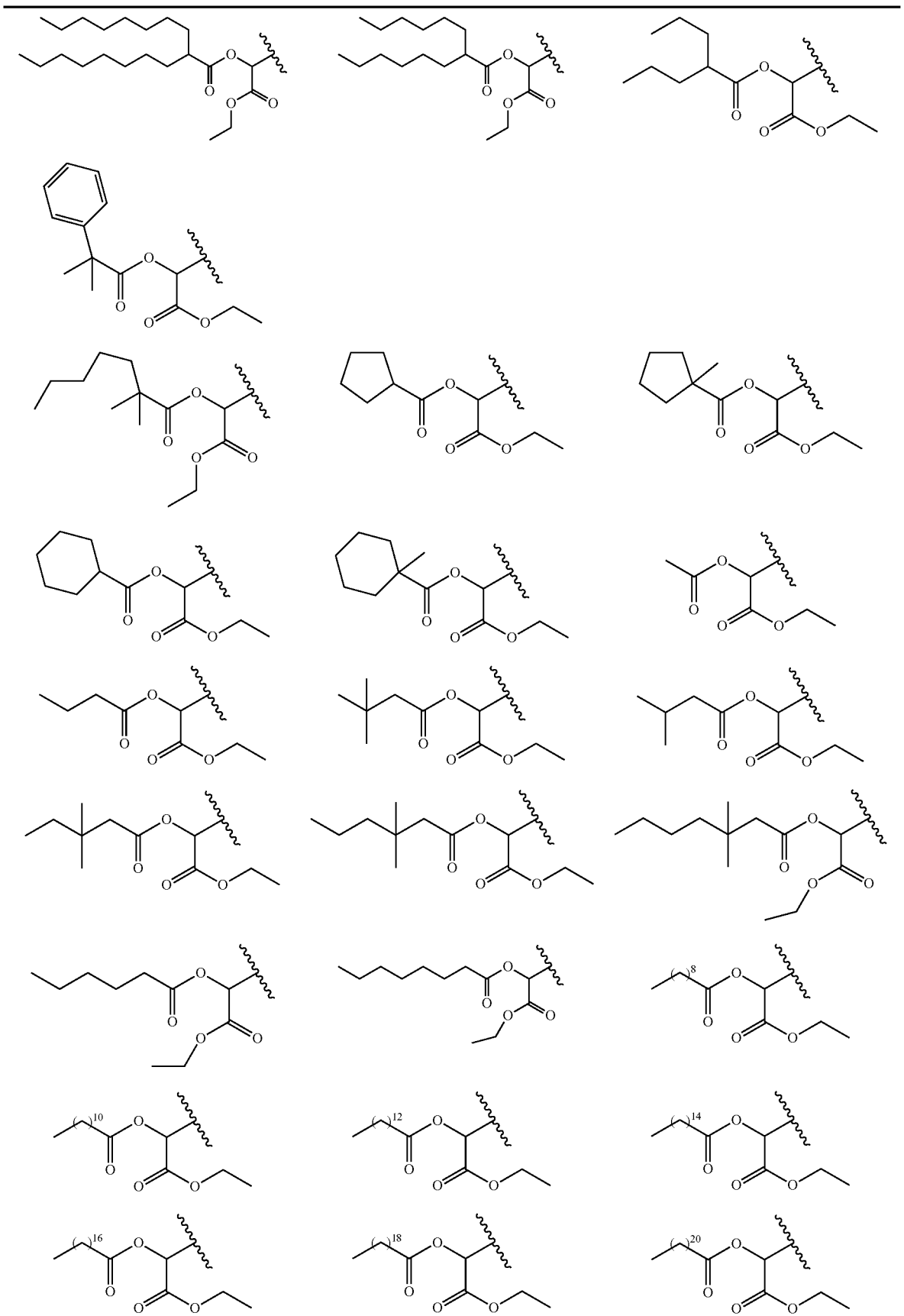

TABLE 1-continued
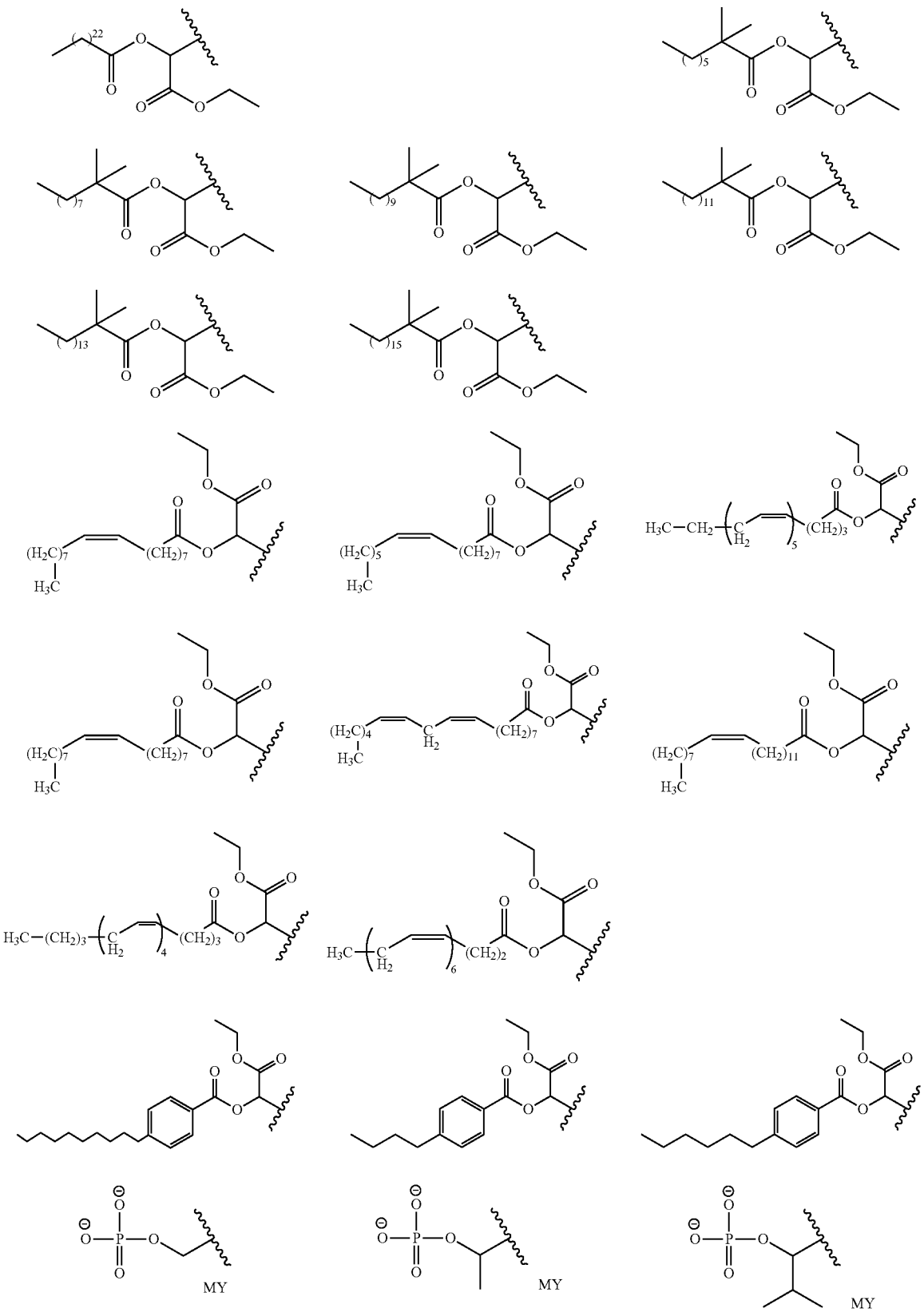

TABLE 1-continued
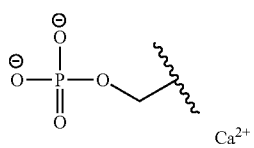 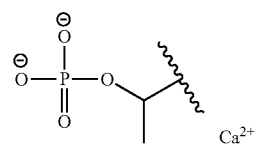 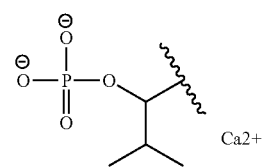
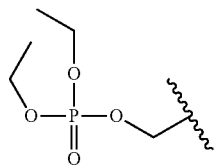 [SMILES: *COP(=O)(OCC)OCC] 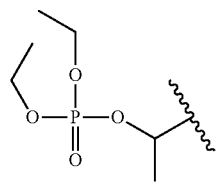 [SMILES: *C(C)OP(=O)(OCC)OCC] 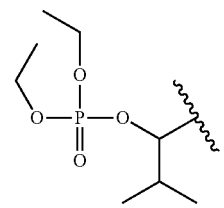 [SMILES: *C(OP(=O)(OCC)OCC)C(C)C]
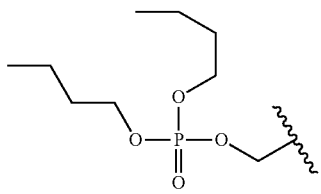 [SMILES: *COP(=O)(OCCCC)OCCCC] 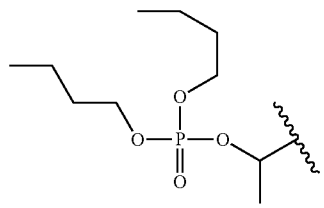 [SMILES: *C(C)OP(=O)(OCCCC)OCCCC] 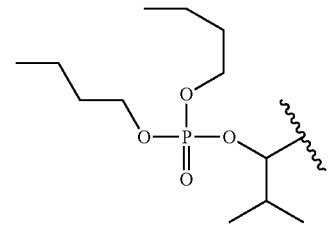 [SMILES: *C(OP(=O)(OCCCC)OCCCC)C(C)C]
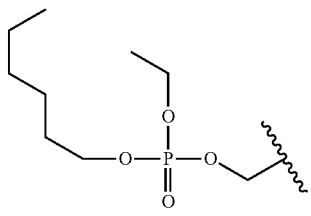 [SMILES: *COP(=O)(OCC)OCCCCCC] 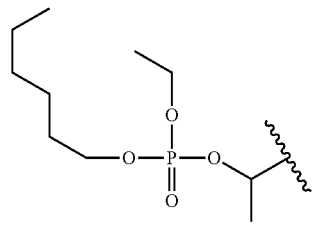 [SMILES: *C(C)OP(=O)(OCC)OCCCCCC] 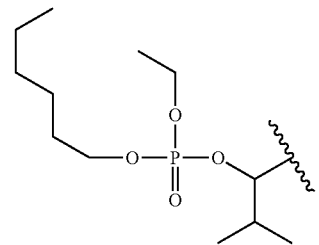 [SMILES: *C(OP(=O)(OCC)OCCCCCC)C(C)C]
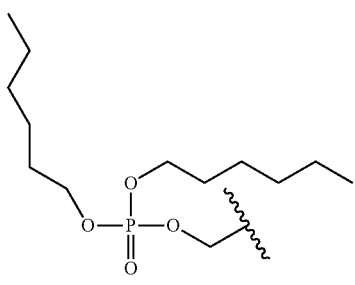 [SMILES: *COP(=O)(OCCCCCC)OCCCCCC] 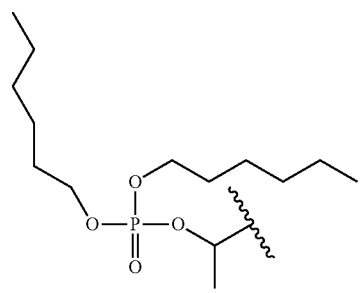 [SMILES: *C(C)OP(=O)(OCCCCCC)OCCCCCC] 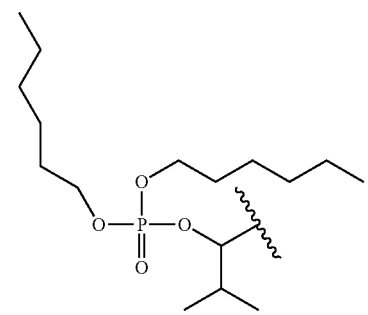 [SMILES: *C(OP(=O)(OCCCCCC)OCCCCCC)C(C)C]
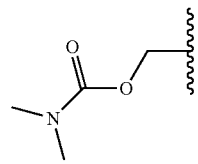 [SMILES: *COC(=O)N(C)C] 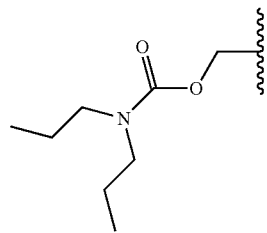 [SMILES: *COC(=O)N(CCC)CCC] 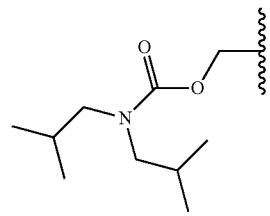 [SMILES: *COC(=O)N(CC(C)C)CC(C)C]

TABLE 1-continued
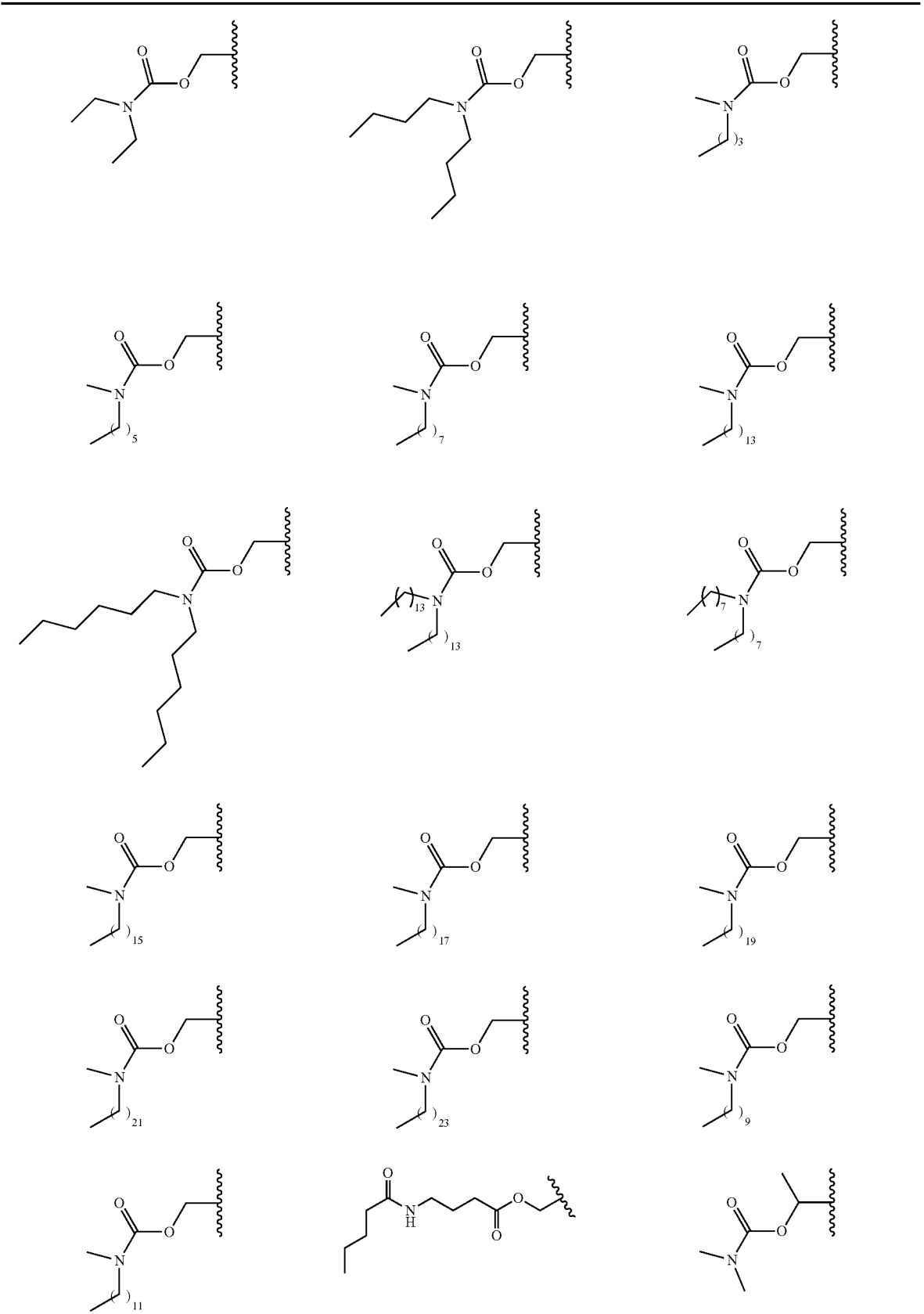

TABLE 1-continued
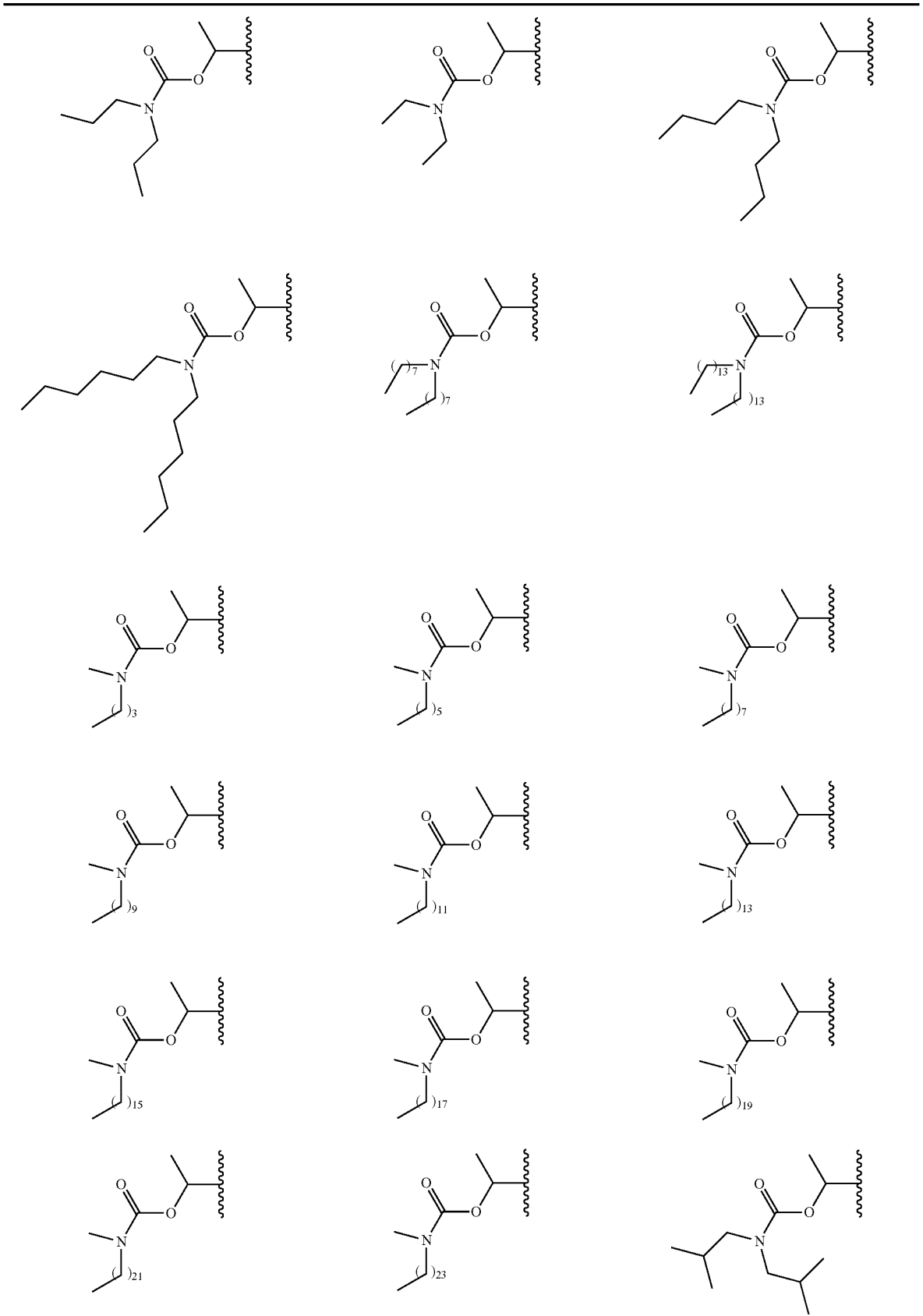

TABLE 1-continued
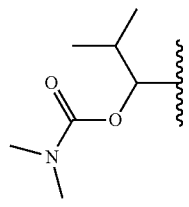 [SMILES: *C(OC(=O)N(C)C)C(C)C] 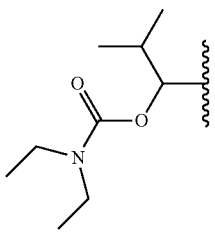 [SMILES: *C(OC(=O)N(CC)CC)C(C)C] 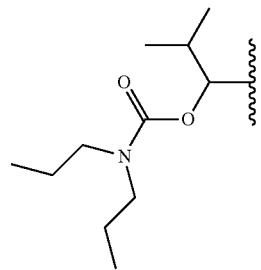 [SMILES: *C(OC(=O)N(CCC)CCC)C(C)C]
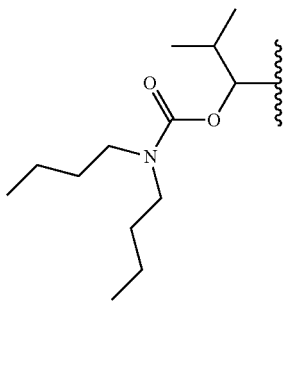 [SMILES: *C(OC(=O)N(CCCC)CCCC)C(C)C] 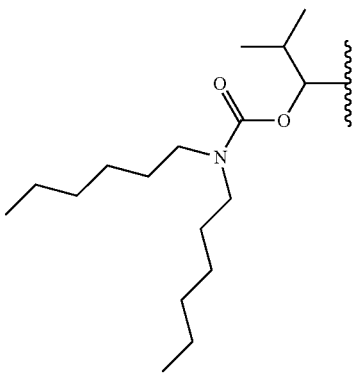 [SMILES: *C(OC(=O)N(CCCCCC)CCCCCC)C(C)C] 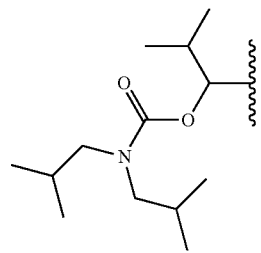 [SMILES: *C(OC(=O)N(CC(C)C)CC(C)C)C(C)C]
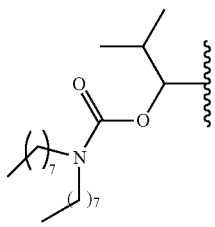 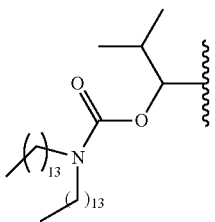 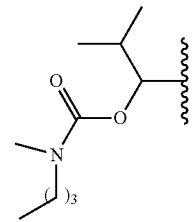
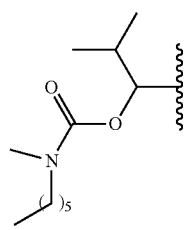 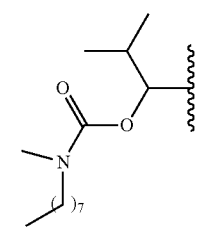 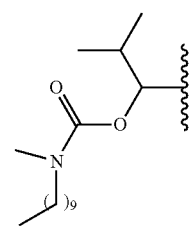
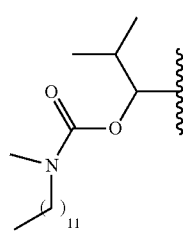 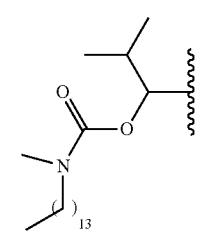 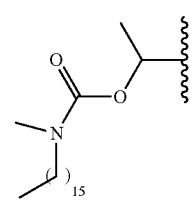
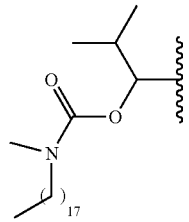 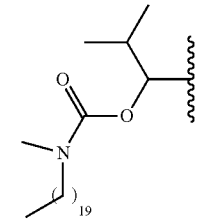 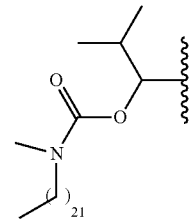

TABLE 1-continued
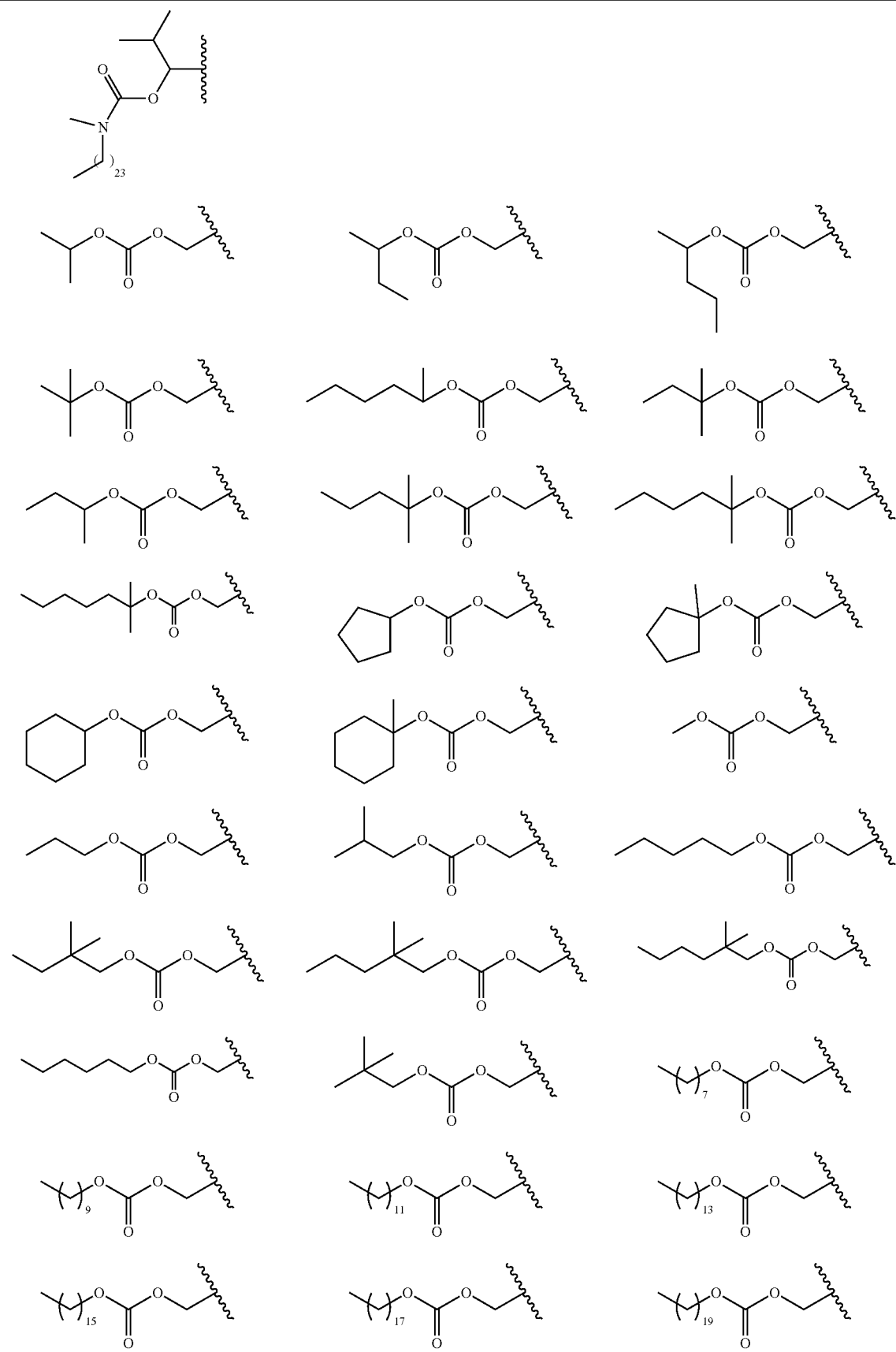

TABLE 1-continued
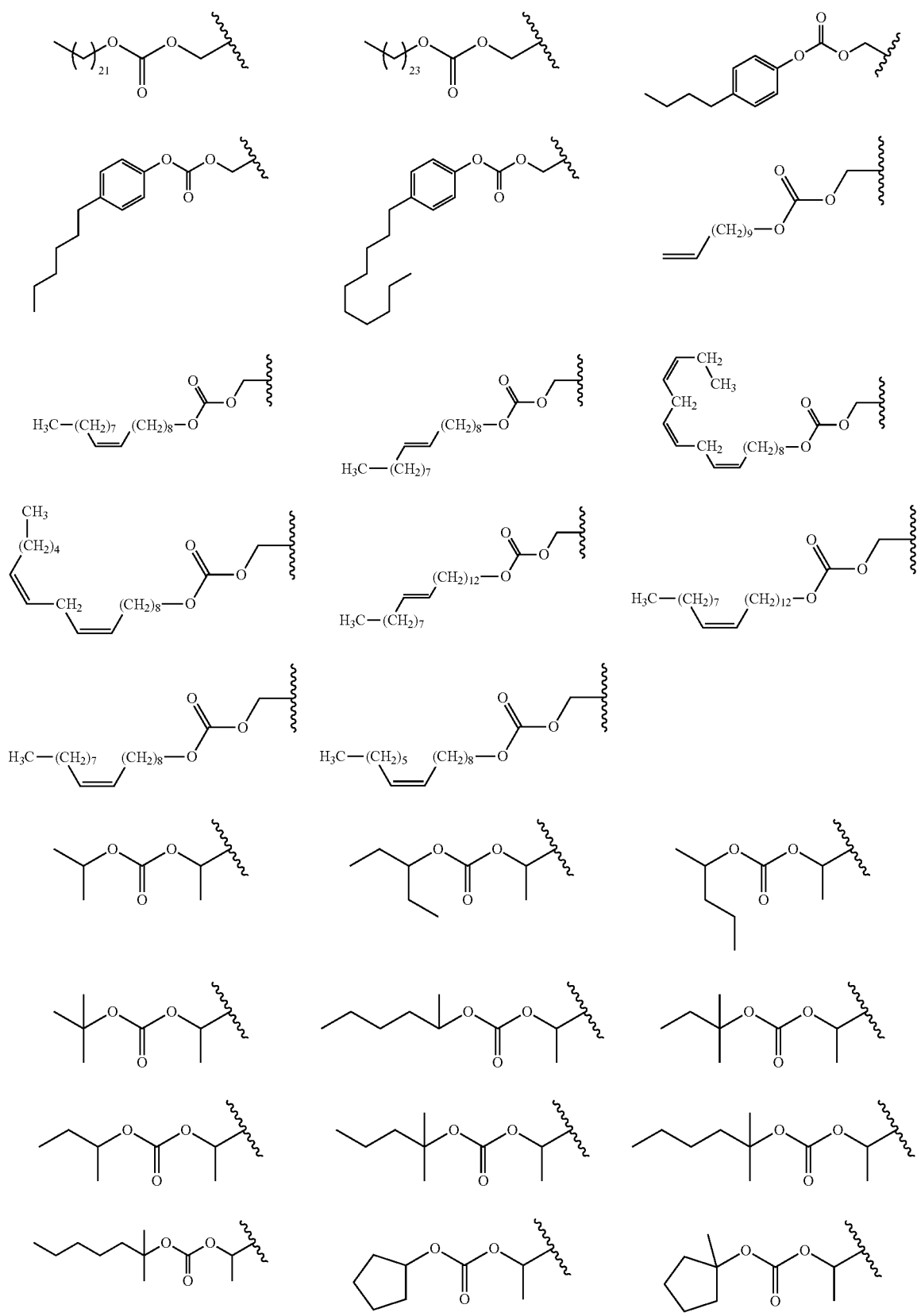

TABLE 1-continued
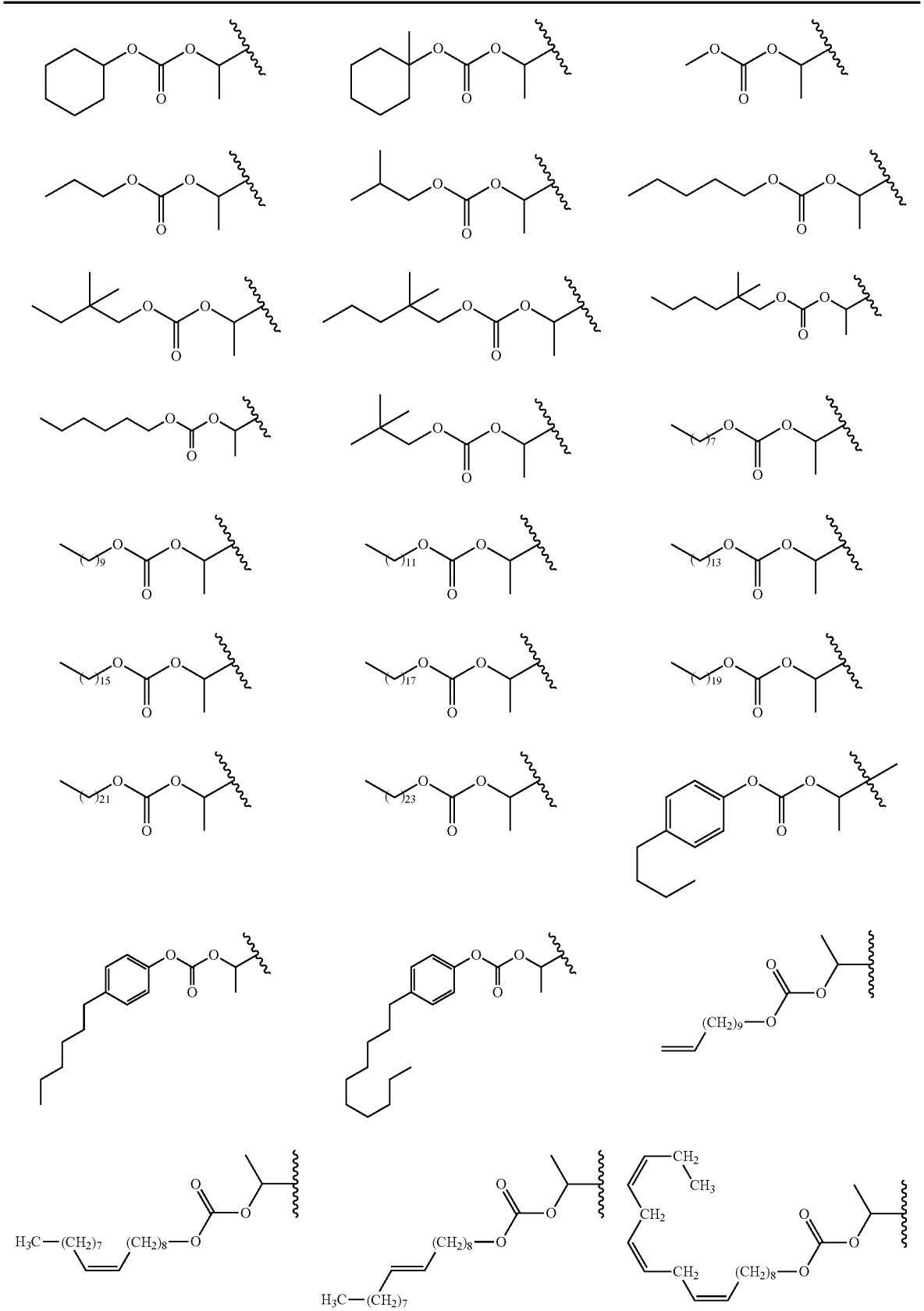

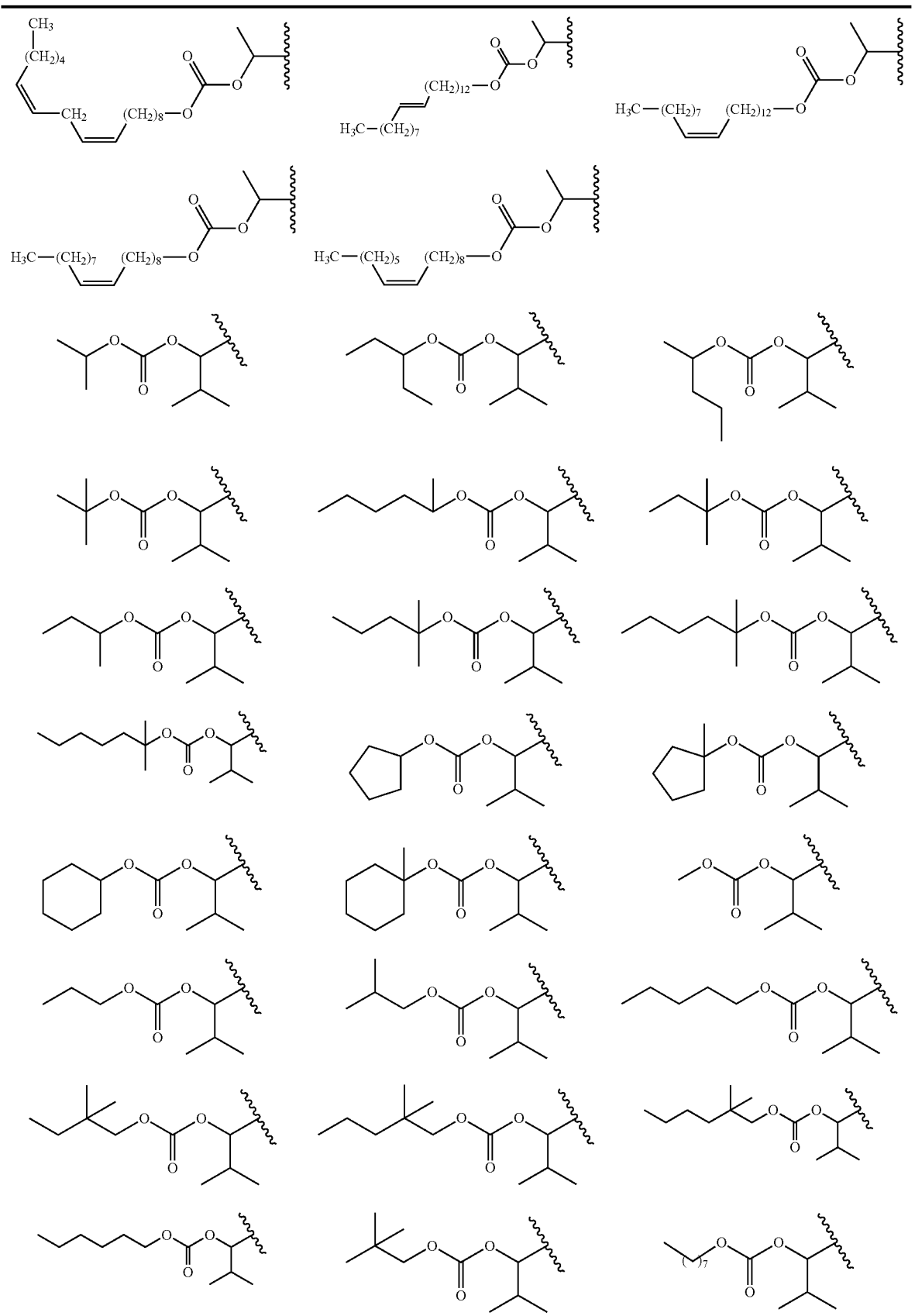

TABLE 1-continued
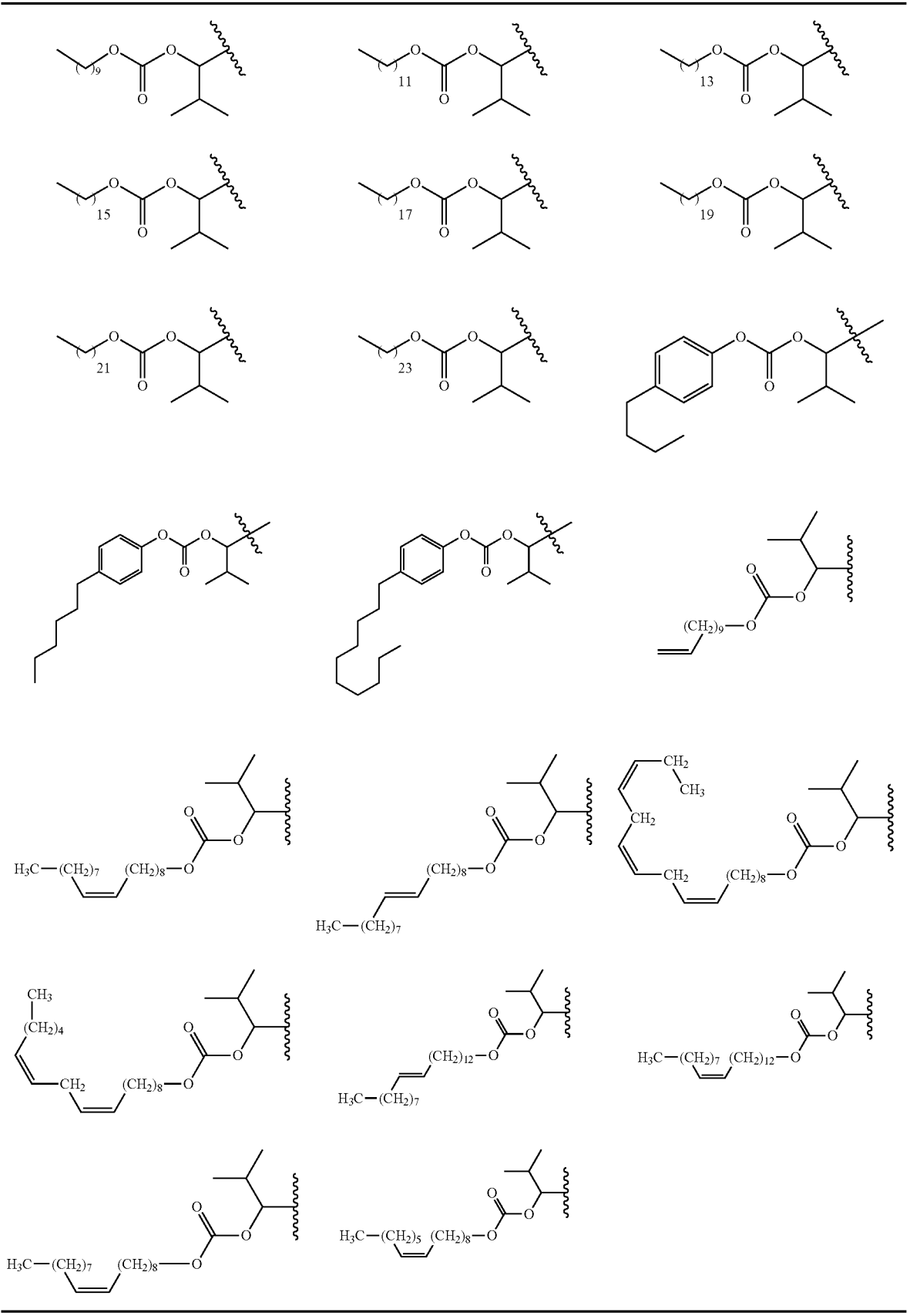

TABLE 2
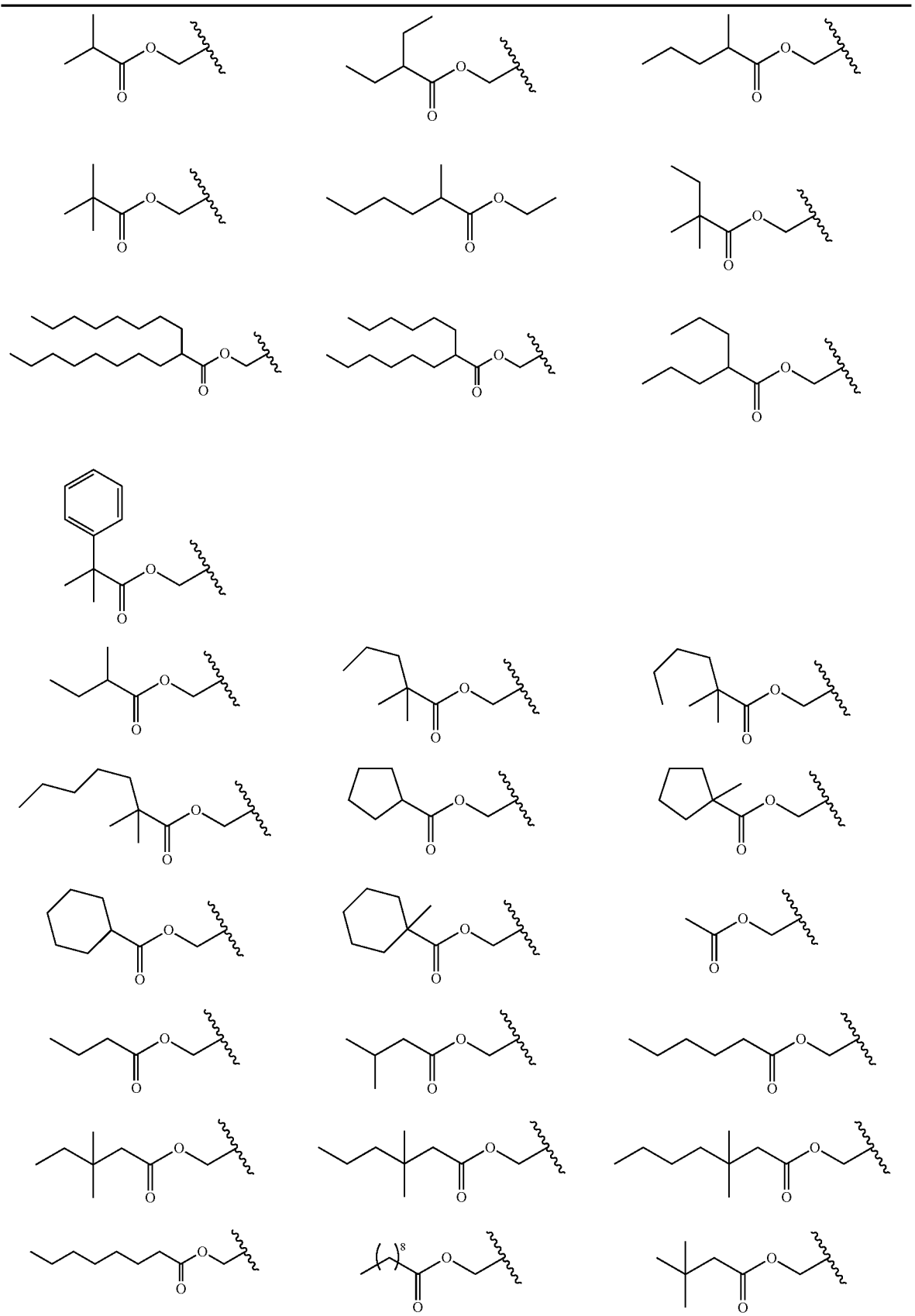

TABLE 2-continued
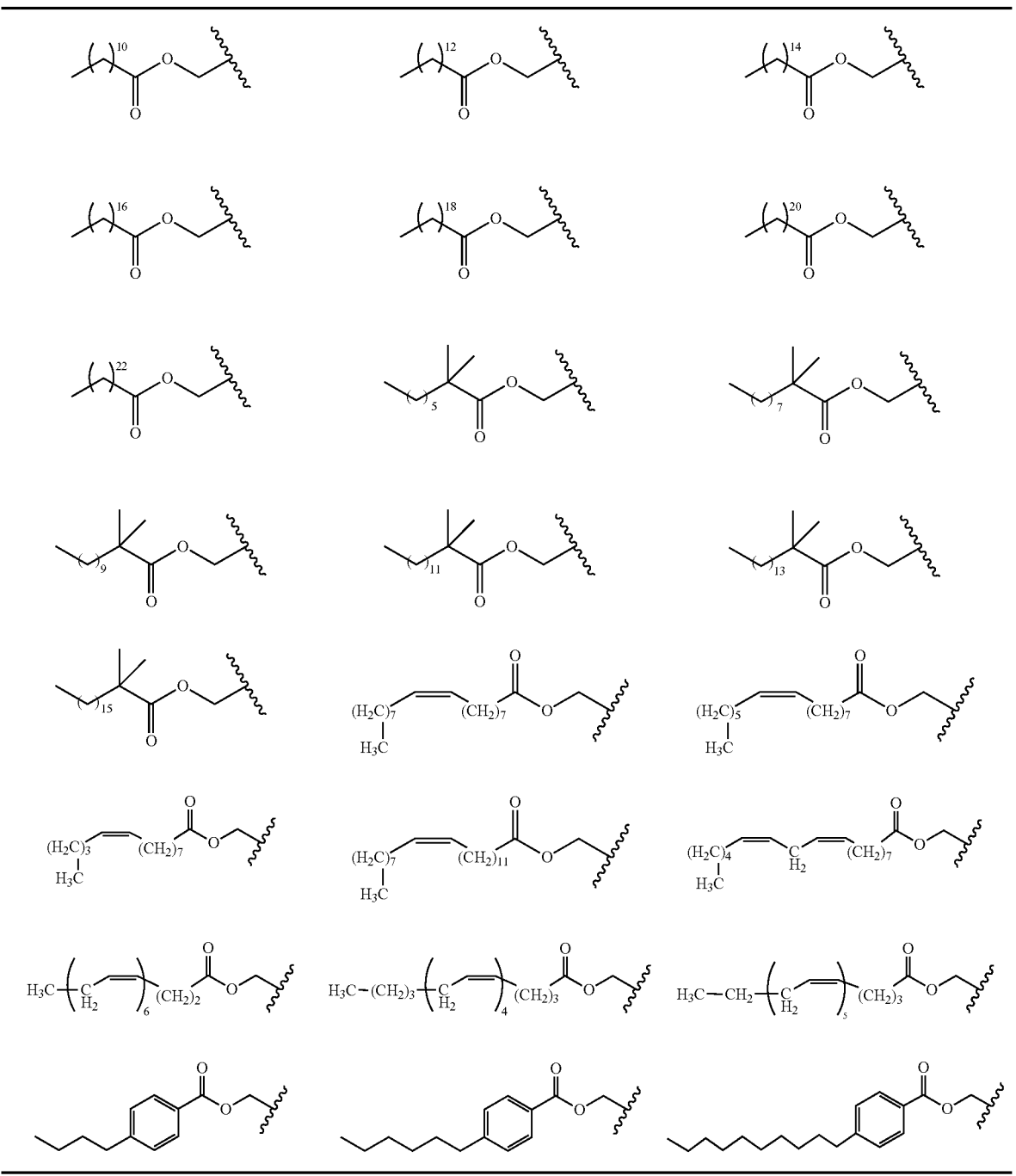
TABLE 3

TABLE 3-continued
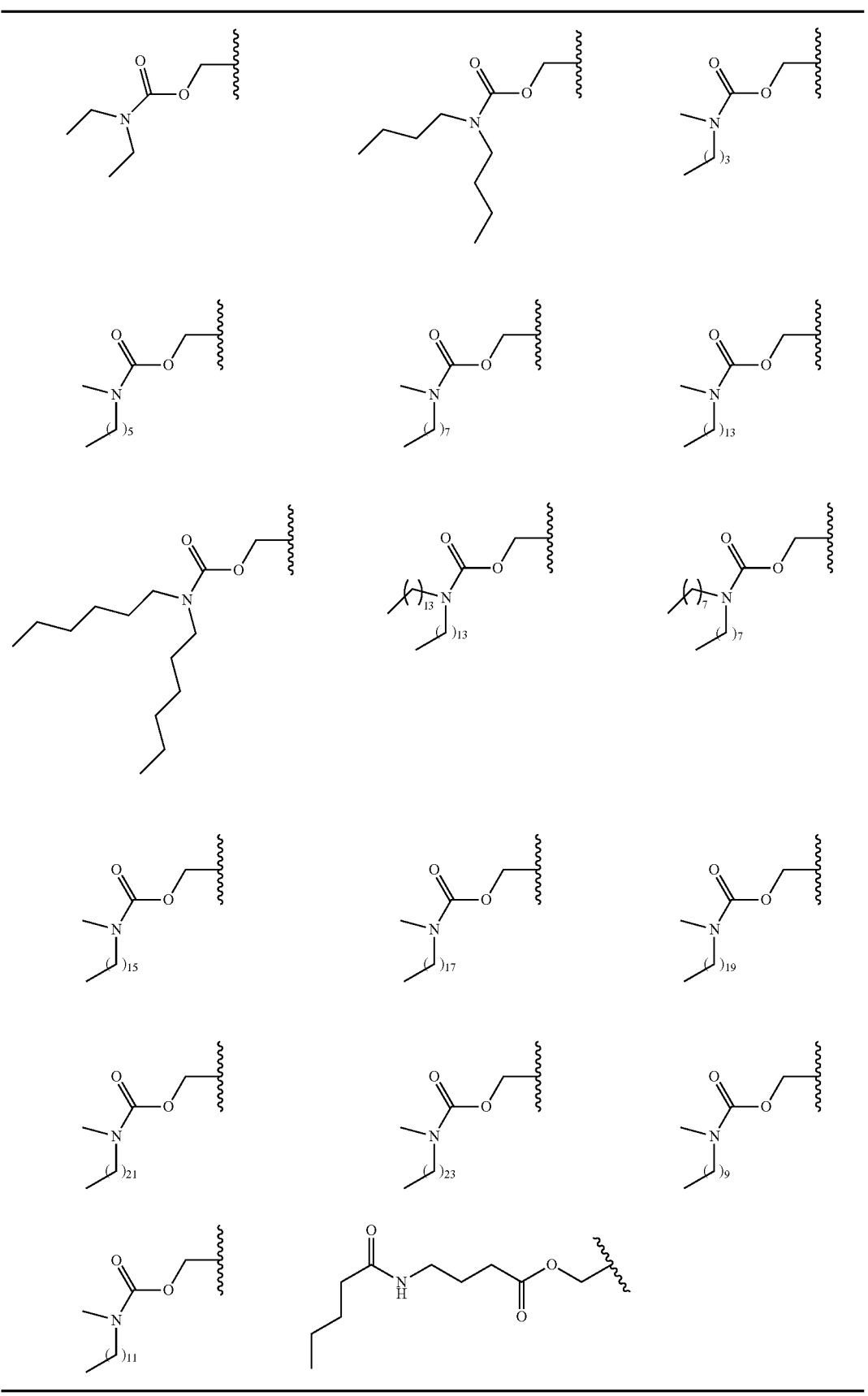

TABLE 4
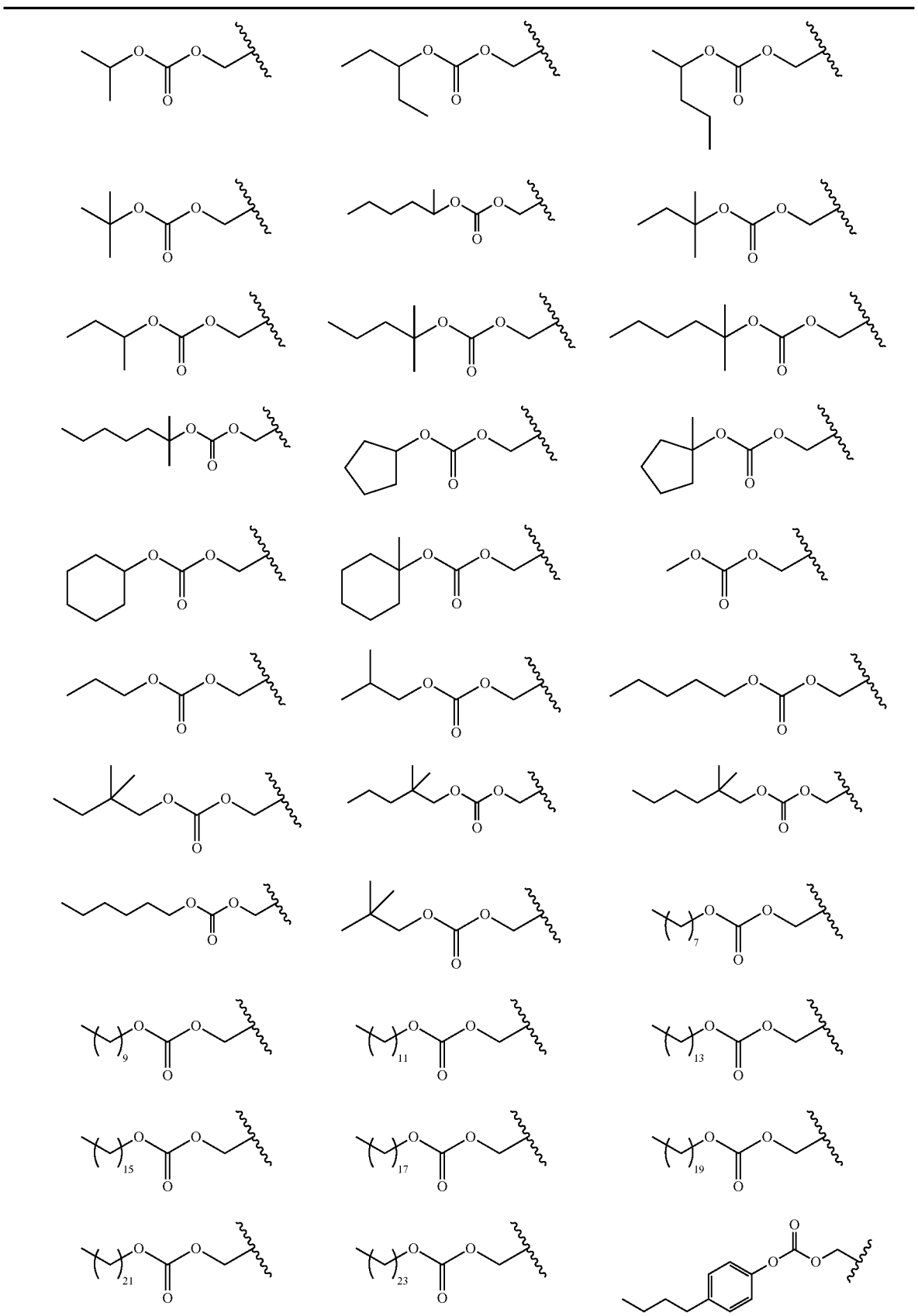

TABLE 4-continued

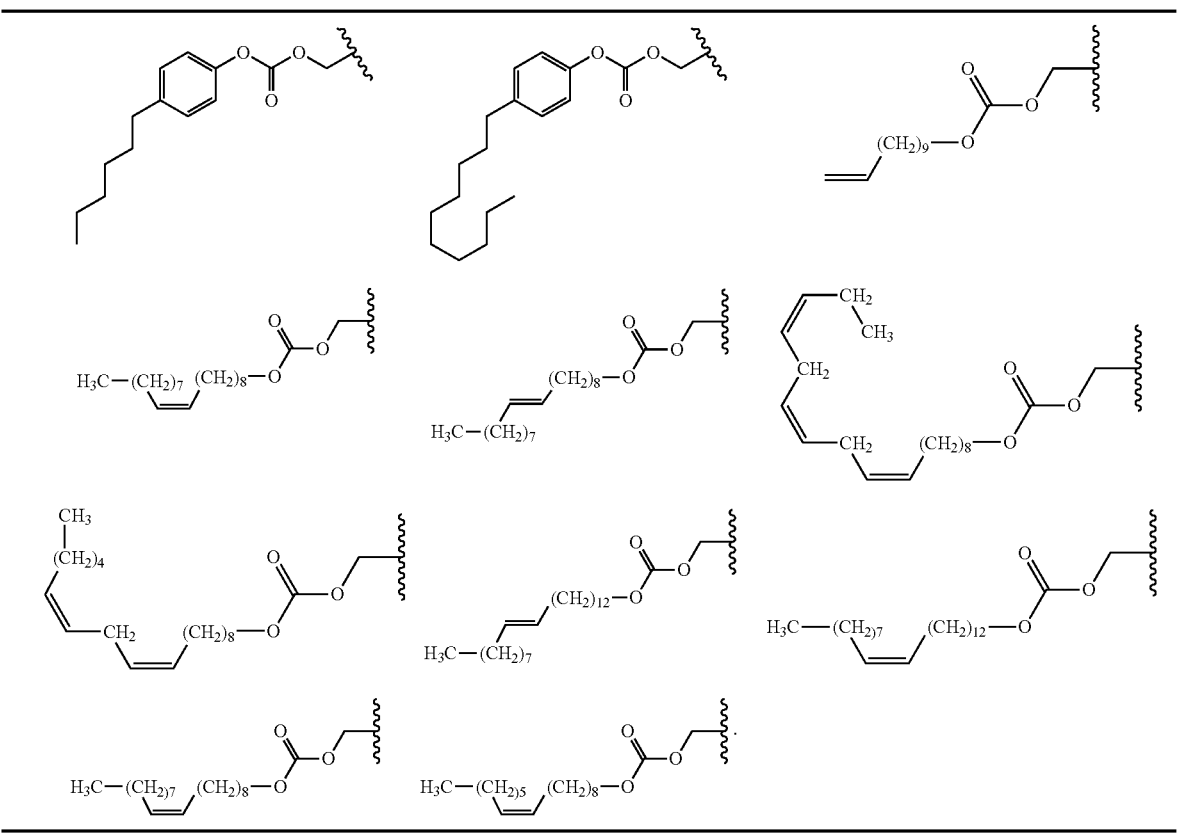

4. The method according to claim 1, wherein said compound of Formula II is selected from 3,4-dichloro-5,6-dicyano-1,4-benzoquinone, 3,4,5,6-tetrachloro-1,2-benzquinone, ortho-benzoquinone and para-benzoquinone.

5. The method according to claim 1, wherein said acid is selected from trifluoroacetic acid, p-toluenesulfonic acid, trifluoromethanesulfonic acid, chlorosulfonic acid, dichloroacetic acid, trichloroacetic acid, acetic acid, propionic acid, sulfuric acid, phosphoric acid, nitric acid, camphorsulfonic acid, hydrochloric acid, oxalic acid, formic acid, propanoic acid, butanoic acid, pentanoic acid, benzoic acid, pyruvic acid, malonic acid, succinic acid, glutaric acid, fumaric acid, citric acid, ascorbic acid, tartaric acid, maleic acid, hydrobromic acid, and mixtures thereof.

6. The method according to claim 1, wherein the reaction is conducted in a solvent selected from tetrahydrofuran, tert-butylmethylether, dimethoxy-ethane, dioxane, benzene, toluene, xylene, dimethylformamide, acetone, acetonitrile, chloroform, dichloromethane, 1,2-dichloroethane, ethyl acetate, n-propyl acetate, isopropyl acetate, methyl-t-butyl ether, methyl butyl ketone and combinations thereof.

7. The method according to claim 1, wherein said pKa range of primary, secondary or tertiary amine is between about 6 to about 30.

* * * * *

UNITED STATES PATENT AND TRADEMARK OFFICE
CERTIFICATE OF CORRECTION

PATENT NO. : 8,536,328 B2  
APPLICATION NO. : 13/100515  
DATED : September 17, 2013  
INVENTOR(S) : Julius F. Remenar, Laura Cook Blumberg and Tarek A. Zeidan Page 1 of 1

It is certified that error appears in the above-identified patent and that said Letters Patent is hereby corrected as shown below:

In the Claims

Column 118, line 10, Claim 2, please delete "$OR_2O$" and insert -- $OR_{20}$ --

Columns 117 and 118, Table 1, line 2, Claim 3, therein, delete " 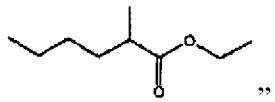 "

Columns 117 and 118, Table 1, line 3, Claim 3, delete " 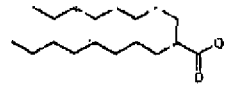  "

and insert -- 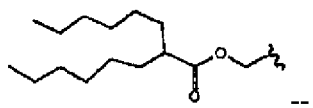 --

Columns 125 and 126, Table 1, line 1, Claim 3, delete " 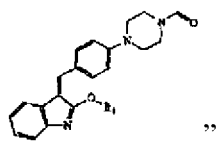 "

Signed and Sealed this  
Eighteenth Day of November, 2014

Michelle K. Lee  
*Deputy Director of the United States Patent and Trademark Office*